(12) United States Patent
Shelton, IV et al.

(10) Patent No.: US 10,932,808 B2
(45) Date of Patent: Mar. 2, 2021

(54) METHODS, SYSTEMS, AND DEVICES FOR CONTROLLING ELECTROSURGICAL TOOLS

(71) Applicant: Ethicon LLC, Guaynabo, PR (US)

(72) Inventors: Frederick E. Shelton, IV, Hillsboro, OH (US); Jason L. Harris, Lebanon, OH (US); David C. Yates, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 600 days.

(21) Appl. No.: 15/689,072

(22) Filed: Aug. 29, 2017

(65) Prior Publication Data

US 2019/0059929 A1 Feb. 28, 2019

(51) Int. Cl.
*A61B 18/14* (2006.01)
*A61B 17/32* (2006.01)
(Continued)

(52) U.S. Cl.
CPC .. *A61B 17/320092* (2013.01); *A61B 18/1445* (2013.01); *A61B 34/30* (2016.02); *A61B 90/03* (2016.02); *A61B 2017/00017* (2013.01); *A61B 2017/00026* (2013.01); *A61B 2017/00137* (2013.01); *A61B 2017/00398* (2013.01);
(Continued)

(58) Field of Classification Search
CPC ............ A61B 18/1442; A61B 18/1445; A61B 2018/1452; A61B 2018/1455; A61B 2018/00994; A61B 2018/00607; A61B 2018/00875; A61B 2018/00958; A61B 2018/00636; A61B 2018/00666; A61B 17/320092; A61B 17/320068; A61B 34/30; A61B 2017/00026; A61B 2017/00398; A61B 2017/00137; A61B 2017/00017; A61B 2017/2927; A61B 2017/320094; A61B 2017/320095
USPC ............... 606/34, 37, 38, 41, 42, 48, 50–52; 607/98, 99, 101, 113, 115, 116
See application file for complete search history.

(56) References Cited

U.S. PATENT DOCUMENTS 5,322,055 A 6/1994 Davison et al.
5,472,443 A 12/1995 Cordis et al.
(Continued)

FOREIGN PATENT DOCUMENTS

WO WO-2014151621 A1 9/2014
WO WO-2014151952 A1 9/2014
WO WO-2016100682 A1 6/2016

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Thomas A Giuliani
(74) *Attorney, Agent, or Firm* — Mintz Levin Cohn Ferris Glovsky and Popeo, P.C.

(57) ABSTRACT

Various exemplary methods, systems, and devices for controlling electrosurgical tools are provided. In general, an electrosurgical tool is configured to apply energy to tissue, such as via an end effector of the surgical tool. The energy can include one or more types of energy, such as electrical energy, ultrasonic energy, and heat energy. The electrical energy can be a high frequency alternating current such as radiofrequency (RP) energy, or can be another type of electrical energy.

20 Claims, 27 Drawing Sheets

(51) Int. Cl.
*A61B 34/30* (2016.01)
*A61B 17/00* (2006.01)
*A61B 18/00* (2006.01)
*A61B 17/29* (2006.01)
*A61B 90/00* (2016.01)

(52) U.S. Cl.
CPC .......... *A61B 2017/2927* (2013.01); *A61B 2017/2929* (2013.01); *A61B 2017/320074* (2017.08); *A61B 2017/320094* (2017.08); *A61B 2017/320095* (2017.08); *A61B 2018/00589* (2013.01); *A61B 2018/00601* (2013.01); *A61B 2018/00607* (2013.01); *A61B 2018/00666* (2013.01); *A61B 2018/00875* (2013.01); *A61B 2018/00994* (2013.01); *A61B 2018/1455* (2013.01); *A61B 2090/031* (2016.02); *A61B 2090/066* (2016.02)

(56) References Cited

U.S. PATENT DOCUMENTS

| | | |
|---|---|---|
| 5,558,671 A | 9/1996 | Yates |
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,132,368 A | 10/2000 | Cooper |
| 6,168,605 B1 | 1/2001 | Measamer et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 | 6/2013 | Holcomb et al. |
| 8,602,286 B2 | 12/2013 | Crainich et al. |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 | 7/2015 | Shelton, IV et al. |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 9,713,507 B2 | 7/2017 | Stulen et al. |
| 9,808,246 B2 | 11/2017 | Shelton, IV et al. |
| 2003/0114851 A1 | 6/2003 | Truckai et al. |
| 2004/0030328 A1 | 2/2004 | Eggers et al. |
| 2005/0222560 A1 | 10/2005 | Kimura et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2009/0138006 A1 | 5/2009 | Bales et al. |
| 2009/0157071 A1 | 6/2009 | Wham et al. |
| 2010/0191282 A1 | 7/2010 | Harris et al. |
| 2010/0198248 A1 | 8/2010 | Vakharia |
| 2010/0228264 A1* | 9/2010 | Robinson .............. A61B 34/76 606/130 |
| 2011/0015631 A1 | 1/2011 | Wiener et al. |
| 2011/0015632 A1* | 1/2011 | Artale .............. A61B 18/1445 606/51 |
| 2011/0087218 A1 | 4/2011 | Boudreaux et al. |
| 2011/0087256 A1 | 4/2011 | Wiener et al. |
| 2011/0290855 A1 | 12/2011 | Moore et al. |
| 2012/0022517 A1 | 1/2012 | Stuebe |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0292367 A1 | 11/2012 | Morgan et al. |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0261648 A1 | 10/2013 | Laurent et al. |
| 2013/0325034 A1 | 12/2013 | Schena et al. |
| 2014/0005718 A1 | 1/2014 | Shelton, IV et al. |
| 2014/0114327 A1 | 4/2014 | Boudreaux et al. |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0263541 A1 | 9/2014 | Leimbach et al. |
| 2014/0276931 A1 | 9/2014 | Parihar et al. |
| 2015/0209059 A1 | 7/2015 | Trees et al. |
| 2015/0209573 A1 | 7/2015 | Hibner et al. |
| 2015/0265347 A1 | 9/2015 | Yates et al. |
| 2015/0272575 A1 | 10/2015 | Leimbach et al. |
| 2015/0282825 A1 | 10/2015 | Trees et al. |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089175 A1 | 3/2016 | Hibner et al. |
| 2016/0089533 A1 | 3/2016 | Turner et al. |
| 2016/0175036 A1 | 6/2016 | Horner et al. |
| 2016/0175060 A1 | 6/2016 | Park |
| 2016/0287252 A1 | 10/2016 | Parihar |
| 2016/0367243 A1 | 12/2016 | Martin et al. |
| 2017/0000541 A1* | 1/2017 | Yates .............. A61B 18/1445 |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2019/0059972 A1 | 2/2019 | Shelton, IV et al. |
| 2019/0059985 A1 | 2/2019 | Shelton, IV et al. |
| 2019/0059986 A1 | 2/2019 | Shelton, IV et al. |
| 2019/0059987 A1 | 2/2019 | Shelton, IV et al. |

OTHER PUBLICATIONS

U.S. Appl. No. 15/237,653 entitled "Methods, Systems, and Devices for Controlling a Motor of a Robotic Surgical System" filed Aug. 16, 2016.
U.S. Appl. No. 15/422,767 entitled "Robotic Surgical System and Methods for Articulation Calibration" filed Feb. 2, 2017.
U.S. Appl. No. 15/634,620 entitled "Surgical Stapler with Independently Actuated Drivers to Provide Varying Staple Heights" filed Jun. 27, 2017.
U.S. Appl. No. 15/674,075 entitled "Clip Retention for Surgical Clip Applier" filed Aug. 10, 2017.

(56) References Cited

OTHER PUBLICATIONS

U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 29/613,511 entitled "Clip Applier Rotation Knob" filed Aug. 10, 2017.
International Search Report and Written Opinion for Intl. App. No. PCT/IB2018/056364 dated Feb. 14, 2019 (21 pages).

\* cited by examiner

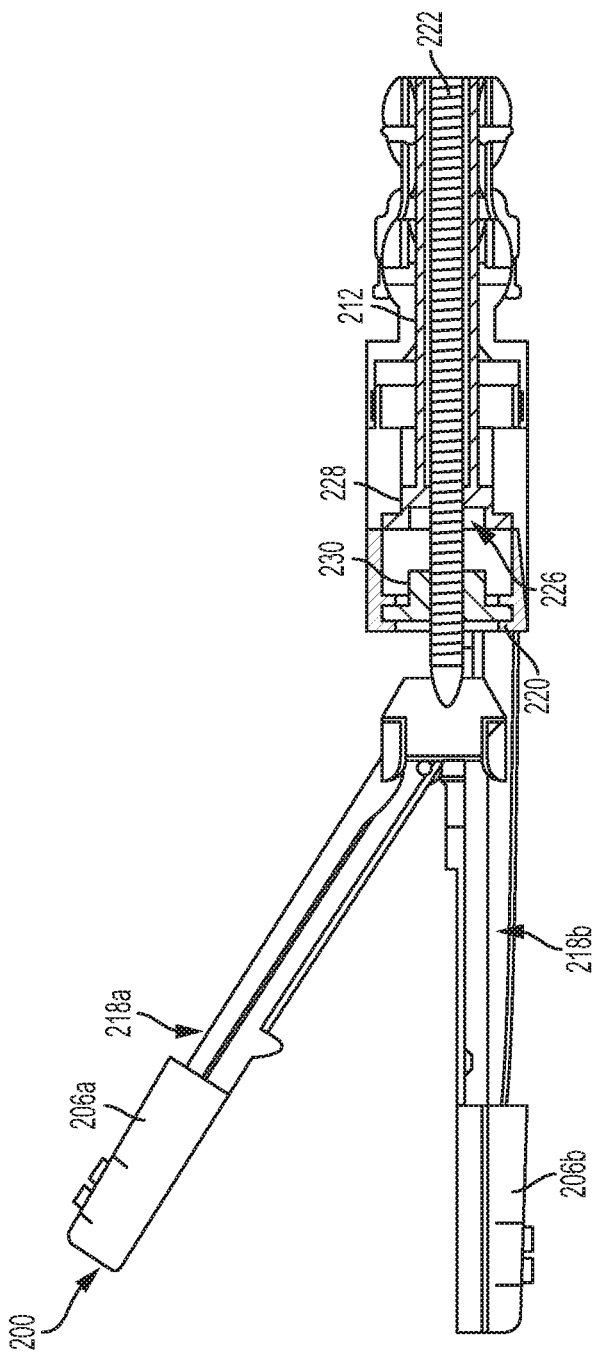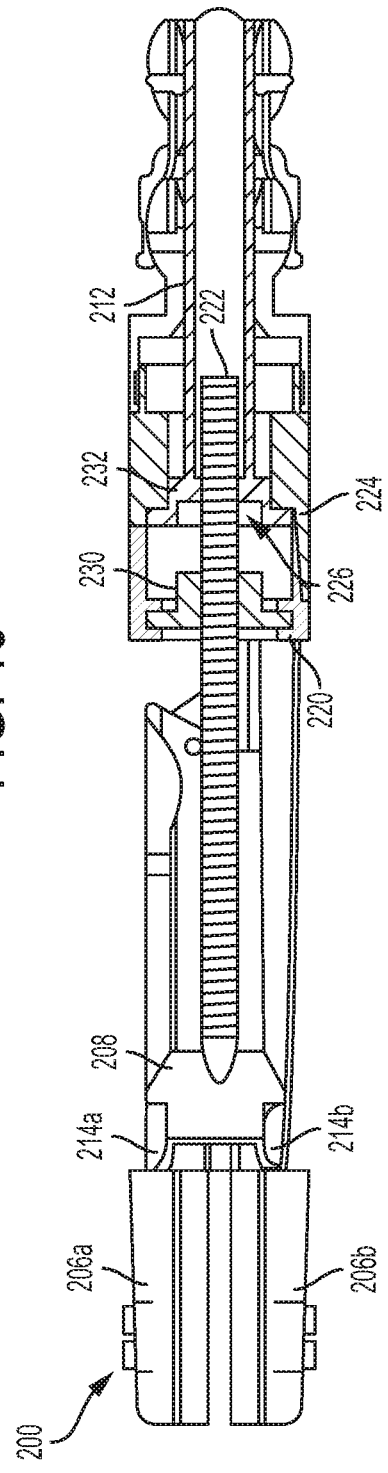

|  | TISSUE MANIPULATION | ENERGY TRIGGER | CLAMP | SEAL | CUT |
|---|---|---|---|---|---|
| KNIFE CUT | O | O | O | O | I |
| ARTICULATION | I | O | O | O | O |
| SHAFT ROTATION | I | O | O | O | O |
| GRASP/CLAMP | I | I | O | O | O |
| SEAL | O | I | I | I | I |

O = LOCKED OUT
I = POSSIBLE

FIG. 26

| $S_A$ | $S_B$ | $Z_{ESU}$ |
|---|---|---|
| OPEN | OPEN | $Z_{TISSUE} \| \|$ |
| CLOSED | OPEN | $Z_{TISSUE} \| \| R_A$ |
| OPEN | CLOSED | $Z_{TISSUE} \| \| R_B$ |
| CLOSED | CLOSED | $Z_{TISSUE} \| \| R_A \| \| R_B$ |

METHODS, SYSTEMS, AND DEVICES FOR CONTROLLING ELECTROSURGICAL TOOLS

FIELD

The present disclosure relates generally to methods, systems, and devices for controlling electrosurgical tools.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

In general, methods, systems, and devices for controlling electrosurgical tools are provided.

In one aspect, a surgical system is provided that in one embodiment includes an electrosurgical tool including an elongate shaft, an end effector at a distal end of the elongate shaft, a cutting element configured to translate along the end effector to cut tissue grasped by the end effector, and a housing at a proximal end of the elongate shaft. The surgical system also includes a sensor configured to sense an impedance of the tissue grasped by the end effector, and a motor configured to drive the translation of the cutting element along the end effector at a speed based on the sensed impedance and based on a current of the motor during the translation of the cutting element along the end effector.

The surgical system can vary in any number of ways. For example, the speed of the translation can be reduced in response to the sensed impedance being below a predetermined threshold impedance and the current of the motor being below a predetermined threshold current. The speed of the translation can be increased in response to the sensed impedance being above the predetermined threshold impedance and the current of the motor being above a second predetermined threshold current that is lower than the first predetermined threshold current. In at least some embodiments, the speed of the translation can be reduced in response to the current of the motor reaching the predetermined threshold current, and the speed of the translation can be increased in response to the current of the motor reaching the second predetermined threshold current.

For another example, the speed can also be based on a distance of the cutting element from a start position of the cutting element before the cutting element begins to translate. For yet another example, the speed of the translation can be reduced in response to the current of the motor reaching a first predetermined threshold current, and the speed of the translation can be increased in response to the current of the motor reaching a second predetermined threshold current that is lower than the first predetermined threshold current. For still another example, the surgical system can include a tool driver configured to be operatively connected to the housing, and the tool driver can include the motor.

For yet another example, the surgical system can include a control system configured to configured to actuate the motor to drive the translation of the cutting element. The control system can be configured to control the motor to constrain the current of the motor between a first predetermined non-zero threshold current and a second predetermined non-zero threshold current that is lower than the first predetermined non-zero threshold current. The control system can include a processor. In at least some embodiments, a surgical robotic system can include the control system, and the surgical robotic system can includes a tool driver that includes the motor and that is configured to operatively connect to the housing.

For another example, the electrosurgical tool can include at least two electrodes configured to apply energy to the tissue grasped by the end effector. For yet another example, the cutting element can be a blade on an I-beam configured to translate along the end effector. For still another example, the end effector can include a pair of jaws that grasp the tissue therebetween.

In another embodiment, a surgical system includes an electrosurgical tool including an elongate shaft, an end effector at a distal end of the elongate shaft, a cutting element configured to translate along the end effector to cut tissue grasped by the end effector, and a housing at a proximal end of the elongate shaft. The surgical system also includes a motor configured to drive the translation of the cutting element along the end effector at a speed, and a control system configured to control the motor to drive the translation based on a distance of the cutting element from a start position of the cutting element before the cutting element begins to translate and based on a current of the motor during the translation of the cutting element along the end effector.

The surgical system can have any number of variations. For example, the control system can be configured to control the motor to prevent the translation until the distance of the cutting element from the start position increases to a predetermined threshold distance, and the control system can be configured to control the motor to constrain the current of the motor between a first non-zero threshold current and a second non-zero threshold current that is lower than the first predetermined threshold current. For another example, the surgical system can include a sensor configured to sense an impedance of the tissue grasped by the end effector, and the control system can be configured to control the motor to drive the translation also based on the sensed impedance. For yet another example, the surgical system can include a tool driver configured to be operatively connected to the housing, the tool driver can include the motor, and the tool driver and the control system can be components of a robotic surgical system. For another example, the electrosurgical tool can include at least two electrodes configured to apply energy to the tissue grasped by the end effector. For still another example, the control system can include a processor. For yet another example, the end effector can include a pair of jaws that grasp the tissue therebetween.

In another embodiment, a surgical system includes a treatment tool shaft assembly having a pair of jaws at a distal end thereof and having a clamping assembly configured to move the pair of jaws from an open position to a closed position. The clamping assembly includes an I-beam that includes a tissue-cutting blade. The surgical system also includes a drive assembly operably coupled to the clamping assembly and configured to drive the clamping assembly to move the pair of jaws from an open position to a closed position and to drive the blade through tissue, a motor operably coupled to the drive assembly, and a control system configured to monitor a load on the motor as the blade passes through tissue and to decrease a speed of the blade when the motor load reaches a predetermined upper motor load threshold and to increase the speed of the blade when the motor load reaches a predetermined lower motor load threshold.

The surgical system can vary in any number of ways. For example, the predetermined upper motor load threshold can correspond to a first current of the motor and the predetermined lower motor load threshold can correspond to a second current of the motor that is less than that first current of the motor such that the control system is configured to decrease the speed of the blade when the current of the motor reaches the first current and to increase the speed of the blade when the current of the motor reaches the second current. For another example, the control system can also be configured to control the blade based on at least one of an impedance of the tissue and a longitudinal distance that the blade has moved from an initial position thereof. For yet another example, the control system can include a processor. For still another example, each of the pair of jaws can include at least one electrode thereon that is configured to apply energy to tissue.

In another embodiment, a surgical system includes a surgical tool including an elongate shaft, first and second jaws at a distal end of the elongate shaft, a housing at a proximal end of the elongate shaft, a closure assembly disposed at least partially in the housing and configured to be actuated to move the jaws from an open position to a closed position, and at least one electrode configured to apply energy to tissue clamped between the jaws. The surgical system also includes a control system configured to actuate the closure assembly such that the jaws clamp the tissue with a first clamping force when the at least one electrode is not applying the energy to the tissue and such that the jaws clamp the tissue with a second clamping force when the at least one electrode is applying the energy to the tissue. The second clamping force is higher than the first clamping force.

The surgical system can vary in any number of ways. For example, the surgical system can include a tool driver operatively coupled to the control system and configured to be removably and replaceably operatively coupled to the housing of the surgical tool. The tool driver can include at least one motor, and the control system can be configured to cause the at least one motor to drive the closure assembly. In at least some embodiments, the control system and the tool driver can be components of a robotic surgical system.

For another example, the control system can be configured to cause energy to be delivered to the at least one electrode such that the at least one electrode can apply energy to the tissue clamped between the jaws. For yet another example, the control system can be a component of a robotic surgical system, and the control system can be configured to actuate the closure assembly in response to a user input to the robotic surgical system. For another example, the control system can include a processor. For yet another example, the control system can be configured to actuate the closure assembly such that the jaws move toward the closed position at a speed that varies based on a position of the closure assembly relative to the jaws and based on the clamping force that the jaws clamp the tissue. For another example, the control system can be configured to actuate the closure assembly such that the jaws move toward the closed position at a speed that varies based on an angle of the jaws relative to one another, and the speed can have an inverse relationship with the angle of the jaws. For still another example, the at least one electrode can include at least one electrode on the first jaw and at least one electrode on the second jaw, and, in response to the at least one electrode on the first jaw contacting the at least one electrode on the second jaw, the control system can be configured to cause tissue-facing surfaces of the jaws to be at a predetermined non-zero distance relative to one another. For yet another example, the at least one electrode can include at least one electrode on the first jaw and at least one electrode on the second jaw, the control system can be configured to cause a short between the at least one electrode on the first jaw and the at least one electrode on the second jaw, and, in response to the short, the control system can be configured to cause the jaws to be at a predetermined angle relative to one another.

In another embodiment, a surgical system includes a drive system configured to be removably and replaceably operatively coupled to a surgical tool configured to apply energy to tissue clamped by the surgical tool. The drive system is configured to drive the application of energy. The surgical system also includes an electrosurgical generator; and a control system configured to be operatively coupled to the drive system. The control system is configured to receive energy from the generator, deliver the received energy from the generator to the drive system to drive the application of energy, receive first data via the drive system related to the application of the energy from the surgical tool to the tissue, manipulate the first data to create second data that is modified from the first data, and transmit the second data to the generator to cause the generator to deliver energy to the control system within predefined power parameters of the generator that define a maximum amount of energy the generator can deliver to the control system. Transmitting the first data to the generator would prevent the generator from delivering energy to the control system as being outside the predefined power parameters of the generator.

The surgical system can have any number of variations. For example, the first data can include impedance of the tissue clamped by the surgical tool. In at least some embodiments, the manipulation of the impedance data can include processing with a processor the impedance data through a pair of transformers in parallel.

For another example, the drive system can include at least one motor configured to drive the surgical tool removably and replaceably operatively coupled to the drive system to drive the application of energy. For yet another example, a robotic surgical system can include the drive system and the control system. For still another example, the surgical tool can include first and second jaws configured to clamp the tissue, and each of the first and second jaws can have at least one electrode thereon that is configured to apply the energy to the clamped tissue. For yet another example, the energy can be radiofrequency energy.

In another embodiment, a surgical system includes an electrosurgical generator having predefined power parameters that define a maximum amount of energy the generator can deliver therefrom, and a control system configured to be operatively coupled to a surgical tool configured to apply energy to tissue clamped by the surgical tool. The control system is configured to receive data that is indicative of an impedance of tissue that is clamped by the surgical tool, transform the received data, transmit the transformed data to the generator so as to spoof the generator into delivering energy to the control system because transmission of the untransformed data to the generator prevent the generator from delivering energy to the control system as being outside of the predefined power parameters of the generator, and, after transmitting the transformed data, receive energy from the generator. The control system is also configured to deliver the received energy to the surgical tool to allow the surgical tool to apply energy to the clamped tissue.

The surgical system can vary in any number of ways. For example, transforming the data can include processing with a processor the data through a pair of transformers in parallel.

For another example, the surgical method can include a drive system configured to drive the application of energy in response to control from the control system. The drive system can be configured to operatively couple to the surgical tool, and the drive system can include at least one motor configured to drive the surgical tool removably and replaceably operatively coupled to the drive system to drive the application of energy. In at least some embodiments, a robotic surgical system can include the drive system and the control system.

For yet another example, the surgical tool can include first and second jaws configured to clamp the tissue, and each of the first and second jaws can have at least one electrode thereon that is configured to apply the energy to the clamped tissue. For still another example, the energy can be radiofrequency energy.

In another embodiment, a surgical system includes a surgical tool including an elongate shaft, first and second jaws at a distal end of the elongate shaft, a housing at a proximal end of the elongate shaft, a closure assembly disposed at least partially in the housing and configured to be actuated to move the jaws between an open position and a closed position, and at least two electrodes configured to apply energy to tissue clamped between the jaws. The surgical system also includes a control system configured to actuate the closure assembly to move the jaws between the open position and the closed position, and, when the jaws are in the closed position, determine whether an electrical parameter associated with the surgical tool is at or below a predetermined threshold value. The control system is also configured to, in response to the electrical parameter associated with the surgical tool being determined to be at or below the predetermined threshold value, actuate the closure assembly to cause the jaws to move from the closed positon toward the open position. The control system is also configured to determine if during the movement of the jaws from the closed position toward the open position the electrical parameter changed or remained substantially constant, receive an instruction to deliver energy to the at least two electrodes, and, in response to the received instruction, allow energy to be delivered to the at least two electrodes if it was determined that the electrical parameter remained substantially constant during the movement of the jaws from the closed position toward the open position, and prevent energy from being delivered to the at least two electrodes if it was determined that the electrical parameter changed during the movement of the jaws from the closed position toward the open position.

The surgical system can have any number of variations. For example, the surgical system can include a tool driver operatively coupled to the control system and configured to be removably and replaceably operatively connected to the housing of the surgical tool. The tool driver can include at least one motor, and the control system can be configured to cause the at least one motor to drive the closure assembly. In at least some embodiments, the control system and the tool driver can be components of a robotic surgical system.

For another example, the control system can be a component of a robotic surgical system, and the control system can be configured to actuate the closure assembly in response to a user input to the robotic surgical system. For yet another example, the control system can include a processor. For still another example, the electrical parameter being determined to have remained substantially constant can be indicative of the first and second jaws having tissue clamped therebetween, and the electrical parameter being determined to have changed can be indicative of a short of the at least two electrodes.

In another embodiment, a surgical system includes a surgical tool including an elongate shaft, an end effector at a distal end of the elongate shaft, and a housing at a proximal end of the elongate shaft. The end effector is configured to selectively deliver radiofrequency energy and ultrasound energy to tissue engaged by the end effector. The surgical system also includes a control system configured to cause the end effector to selectively deliver the radiofrequency energy and the ultrasound energy to the tissue, and vary a force applied by the end effector to the tissue engaged by the end effector based on whether the surgical tool is operating in a first mode in which radiofrequency energy but not ultrasound energy is being delivered to the tissue, is operating in a second mode in which both radiofrequency energy and ultrasound energy are being applied to the tissue, and is operating in a third mode in which ultrasound energy but not radiofrequency energy is being applied to the tissue.

The surgical system can vary in any number of ways. For example, the force applied by the end effector to the tissue can be greater in the first and third modes than in the second mode.

For another example, the surgical system can include a sensor configured to sense impedance of the tissue engaged by the end effector, and the control system can be configured to vary the force also based on the sensed impedance. In at least some embodiments, when the surgical tool is operating in the first mode, the control system can be configured to reduce the force in response to the sensed impedance decreasing and to increase the force in response to the sensed impedance increasing.

For yet another example, the end effector can be configured to clamp tissue, and the force can be a compressive force on the clamped tissue. In at least some embodiments, the surgical tool can include a closure assembly disposed at least partially in the housing and configured to be actuated to move the end effector between an open position and a closed position, and the control system can be configured to vary the force by opening or closing the end effector.

For still another example, in the second mode more ultrasound energy than radiofrequency energy can be being applied to the tissue, the surgical tool can be configured to operate in a fourth mode in which both radiofrequency energy and ultrasound energy are being applied to the tissue and more radiofrequency energy than ultrasound energy is being applied to the tissue, and the control system can be configured to vary the force also based on whether the surgical tool is operating in the fourth mode. For another example, the surgical tool operating in the first mode can cause coagulation of the tissue engaged by the end effector, the surgical tool operating in the second mode can enhance the coagulation, and the surgical tool operating in the third mode can cause cutting of the tissue engaged by the end effector. For still another example, the control system can include a processor.

For yet another example, the surgical system can include a tool driver of a robotic surgical system configured to operatively connect to the housing, and the control system can be a component of the robotic surgical system. In at least some embodiments, the tool driver can include at least one motor configured to drive the delivery of the radiofrequency energy, configured to drive the delivery of the ultrasound energy, and configured to vary the force applied by the end effector.

In another embodiment, a surgical system includes a surgical tool including an elongate shaft, an end effector at a distal end of the elongate shaft, a housing at a proximal end of the elongate shaft, and a closure assembly disposed at least partially in the housing and configured to be actuated to move the end effector between an open position and a closed position. The end effector is configured to selectively deliver radiofrequency energy and ultrasound energy to tissue clamped by the end effector. The surgical system also includes a sensor configured to sense impedance of the tissue engaged by the end effector, a motor configured to drive the closure assembly, and a control system configured to control the motor to drive the actuation of the closure assembly such that the end effector applies a variable compressive force to the tissue clamped thereby based on the sensed impedance and based on whether both radiofrequency energy and ultrasound energy are currently being applied to the tissue clamped by the end effector or only one of radiofrequency energy and ultrasound energy is currently being applied to the tissue clamped by the end effector.

The surgical system can have any number of variations. For example, the compressive force can be less when both radiofrequency energy and ultrasound energy are currently being applied than when only one of radiofrequency energy and ultrasound energy is currently being applied. In at least some embodiments, when both radiofrequency energy and ultrasound energy are currently being applied, the compressive force can be less when more ultrasound energy than radiofrequency energy is currently being applied than when more radiofrequency energy than ultrasound energy is currently being applied.

For another example, the sensed impedance can be indicative of whether both radiofrequency energy and ultrasound energy are currently being applied or only one of radiofrequency energy and ultrasound energy is currently being applied. For yet another example, when only one of radiofrequency energy and ultrasound energy is currently being applied, the control system can be configured to reduce the compressive force in response to the sensed impedance decreasing and is configured to increase the compressive force in response to the sensed impedance increasing. For still another example, the surgical system can include a tool driver assembly configured to be operatively connected to the housing, the tool driver assembly can include the motor, and the tool driver assembly and the control system can be components of a robotic surgical system. For yet another example, the surgical tool can include at least two electrodes configured to apply the radiofrequency energy to the tissue. For another example, the control system can include a processor.

In another aspect, a surgical method is provided that in on embodiment includes actuating a drive system of a robotic surgical system to cause a pair of jaws of a surgical tool to clamp tissue therebetween with a clamping force. The surgical tool is removably and replaceably operatively connected to the drive system. The surgical method also includes actuating the drive system to cause energy to be delivered to the tissue clamped between the jaws, and, in response to the actuation of the drive system to cause the energy to be delivered, causing the pair of jaws to clamp the tissue therebetween with an increased clamping force.

The surgical method can vary in any number of ways. For example, the robotic surgical system can include a control system configured to receive a first input from a user requesting that the pair of jaws clamp the tissue. The control system can be configured to receive a second input from a user requesting that the energy be delivered to the tissue clamped between the jaws. The surgical method can further include, in response to receiving the first input, the control system actuates the drive system to cause the pair of jaws to clamp the tissue therebetween with the clamping force. The surgical method can further include, in response to receiving the second input, the control system actuates the drive system to cause the energy to be delivered and cause the pair of jaws to clamp the tissue therebetween with the increased clamping force. The control system can include a processor.

For another example, the drive system can include at least one motor that drives the clamping of the pair of jaws and that drives the application of the energy.

For yet another example, the energy can be delivered to the tissue by at least one electrode on one of the jaws and at least one electrode on the other of the jaws. In at least some embodiments, the surgical method can include, in response to the at least one electrode on the first jaw contacting the at least one electrode on the second jaw, causing tissue-facing surfaces of the jaws to be at a predetermined non-zero distance relative to one another. In at least some embodiments, the surgical method can include causing a short between the at least one electrode on the first jaw and the at least one electrode on the second jaw, and, in response to the short, causing the jaws to be at a predetermined angle relative to one another.

For still another example, actuating the drive system to cause the pair of jaws to clamp the tissue therebetween can include moving the jaws at a speed from an open position toward a closed position, and the speed can vary based on a position of a closure assembly of the surgical tool relative to the jaws and based on the clamping force. For another example, actuating the drive system to cause the pair of jaws to clamp the tissue therebetween can include moving the jaws at a speed from an open position toward a closed position, the speed can vary based on an angle of the jaws relative to one another, and the speed can have an inverse relationship with the angle of the jaws.

In another embodiment, a surgical method includes actuating a drive system of a robotic surgical system to cause a pair of jaws of a surgical tool to clamp tissue therebetween with a clamping force that does not exceed a predetermined maximum force. The surgical tool is removably and replaceably operatively connected to the drive system. The surgical method also includes actuating the drive system to cause energy to be delivered to the tissue clamped between the jaws, and, in response to the actuation of the drive system to cause the energy to be delivered, increasing the clamping force above the predetermined maximum force such that a distance between tissue-facing surfaces of the jaws is reduced. The surgical method can have any number of variations.

In another embodiment, a surgical method includes receiving at a control system of a robotic surgical system data indicative of an impedance of tissue that is clamped by a surgical tool operatively coupled to the control system, transforming the received data at the control system, transmitting the transformed data from the control system to an electrosurgical generator operatively coupled to the control system, and receiving energy at the control system from the electrosurgical generator. The generator is configured such that the generator can deliver energy to the control system based on the transformed data and such that operating parameters of the generator prevent from delivering energy to the control system based on the untransformed data. The surgical method also includes delivering the received energy from the control system to the surgical tool such that the surgical tool applies the energy to the clamped tissue.

The surgical method can have any number of variations. For example, transforming the received data at the control system can include processing with a processor the received data through a pair of transformers in parallel. For another example, the control system can receive the data via a drive system of the robotic surgical system, and the drive system can be controlled by the control system and can include at least one motor that drives the application of the energy to the clamped tissue. For still another example, the surgical tool can include first and second jaws configured to clamp the tissue, and each of the first and second jaws can have at least one electrode thereon that applies the energy to the clamped tissue. For another example, the energy can be radiofrequency energy.

In another embodiment, a surgical method includes monitoring with a control system of a robotic surgical system an electrical parameter associated with a surgical tool that has first and second jaws thereof in a clamped position. The robotic surgical system includes a tool driver that is operatively coupled to the surgical tool, the first jaw has a first electrode thereon, and the second jaw has a second electrode thereon. The surgical method also includes, in response to the electrical parameter being at or below a predetermined threshold value, causing the tool driver to drive the surgical tool such that a gap between facing surfaces of the first and second jaws increases. The surgical method also includes, during the increasing of the gap, determining with the control system whether the electrical parameter is changing or is remaining substantially constant. The surgical method also includes, in response to the electrical parameter being determined to be remaining substantially constant, allowing energy to be delivered to the first and second electrodes. The surgical method also includes, in response to the electrical parameter being determined to be changing, preventing energy from being delivered to the first and second electrodes.

The surgical method can vary in any number of ways. For example, the electrical parameter can include impedance, and the monitoring can include sensing the impedance using a sensor. For another example, the electrical parameter can include current of a motor of the tool driver, and the motor can have driven the surgical tool to the clamped position. For yet another example, the electrical parameter being determined to be remaining substantially constant can be indicative of the first and second jaws having tissue clamped therebetween, and the electrical parameter being determined to be changing can be indicative of a short of the first and second electrodes. For another example, the tool driver can drive the surgical tool such that the gap between facing surfaces of the first and second jaws increases to a predetermined maximum gap.

For still another example, the surgical method can include, after the increasing of the gap, causing the tool driver to drive the surgical tool such that the gap between facing surfaces of the first and second jaws decreases. In at least some embodiments, causing the tool driver to drive the surgical tool such that the gap between facing surfaces of the first and second jaws decreases can occur prior to either allowing energy to be delivered to the first and second electrodes or preventing energy from being delivered to the first and second electrodes.

For another example, the control system can be configured to cause the tool driver to drive the delivery of the energy to the first and second electrodes. For yet another example, the control system can cause at least one motor of the tool driver to drive the surgical tool such that the gap increases. For still another example, the control system can include a processor.

In another embodiment, a surgical method includes actuating a surgical tool to cause first and second jaws of the surgical tool to move from an open position toward a closed position. The first jaw has a first electrode thereon, and the second jaw has a second electrode thereon. The surgical method also includes, during the movement of the jaws, monitoring an electrical parameter associated with the surgical tool. The surgical method also includes, in response to the electrical parameter dropping to a predetermined threshold value, actuating the surgical tool again to cause the first and second jaws to move toward the open position, determining if during the movement of the first and second jaws toward the open position the electrical parameter remains substantially constant. In response to determining that the electrical parameter remains substantially constant, energy is allowed to be delivered to the first and second electrodes. In response to determining that the electrical parameter does not remain substantially constant, energy is prevented from being delivered to the first and second electrodes.

The surgical method can have any number of variations. For example, the electrical parameter can include impedance, and the monitoring can include sensing the impedance using a sensor. For another example, the electrical parameter can include current of a motor of the tool driver, and the motor can drive the surgical tool to move the first and second jaws from the open position toward the closed position. For yet another example, the electrical parameter being determined to be remaining substantially constant can be indicative of the first and second jaws having tissue clamped therebetween, and the electrical parameter being determined to be changing can be indicative of a short of the first and second electrodes.

For another example, actuating the surgical tool can include a control system of a robotic surgical system causing a tool driver of the robotic surgical system to drive the first and second jaws to move from the open position toward the closed position, and the tool driver can be removably and replaceably coupled to a housing of the surgical tool. In at least some embodiments, the control system can determine if during the movement of the first and second jaws toward the open position the electrical parameter remains substantially constant, and the control system, in response to determining that the electrical parameter remains substantially constant, can allow energy to be delivered to the first and second electrodes, and the control system, in response to determining that the electrical parameter does not remain substantially constant, can prevent energy from being delivered to the first and second electrodes. In at least some embodiments, the surgical method can include, after the determining, receiving at the control system an instruction to deliver energy to the first and second electrodes, and, in response to determining that the electrical parameter remains substantially constant, the control system can allow the energy to be delivered to the first and second electrodes, and, in response to determining that the electrical parameter does not remain substantially constant, the control system can prevent the energy from being delivered to the first and second electrodes. In at least some embodiments, at least one motor of the tool driver can drive the first and second jaws to move from the open position toward the closed position. In at least some embodiments, the control system can include a processor.

In another embodiment, a surgical method includes actuating a tool driver of a robotic surgical system with a control system of the robotic surgical system to cause an end effector of a surgical tool to grasp tissue such that the end effector applies a force to the tissue. The surgical tool is operatively connected to the tool driver. The surgical method also includes actuating the tool driver with the control system to cause the surgical tool to apply energy to the grasped tissue such that radiofrequency energy, but not ultrasound energy, is applied to the grasped tissue and then both radiofrequency energy and ultrasound energy are applied to the grasped tissue. The surgical method also includes causing with the control system the force applied to the tissue to decrease in response to both radiofrequency energy and ultrasound energy being applied to the grasped tissue.

The surgical method can have any number of variations. For example, actuating the tool driver can also cause ultrasound energy, but not radiofrequency energy, to be applied to the grasped tissue after the radiofrequency energy and ultrasound energy are both applied to the grasped tissue, and the surgical method can also include causing with the control system the force applied to the tissue to increase in response to ultrasound energy, but not radiofrequency energy, being applied to the grasped tissue. For another example, the application of radiofrequency energy without the application of ultrasound energy can cause coagulation of the grasped tissue, the application of both radiofrequency energy and ultrasound energy can enhance the coagulation, and the application of ultrasound energy without the application of radiofrequency energy can cut the grasped tissue.

BRIEF DESCRIPTION OF DRAWINGS

This invention will be more fully understood from the following detailed description taken in conjunction with the accompanying drawings, in which:

FIG. 10 is a side cross-sectional view of a distal portion of the tool of FIG. 8 with an end effector thereof open;

FIG. 11 is a side cross-sectional view of a distal portion of the tool of FIG. 8 with an end effector thereof closed;

FIG. 26 is a table illustrating electrosurgical tool functions in various stages of operation illustrated in FIG. 25;

DETAILED DESCRIPTION

Figure 1:
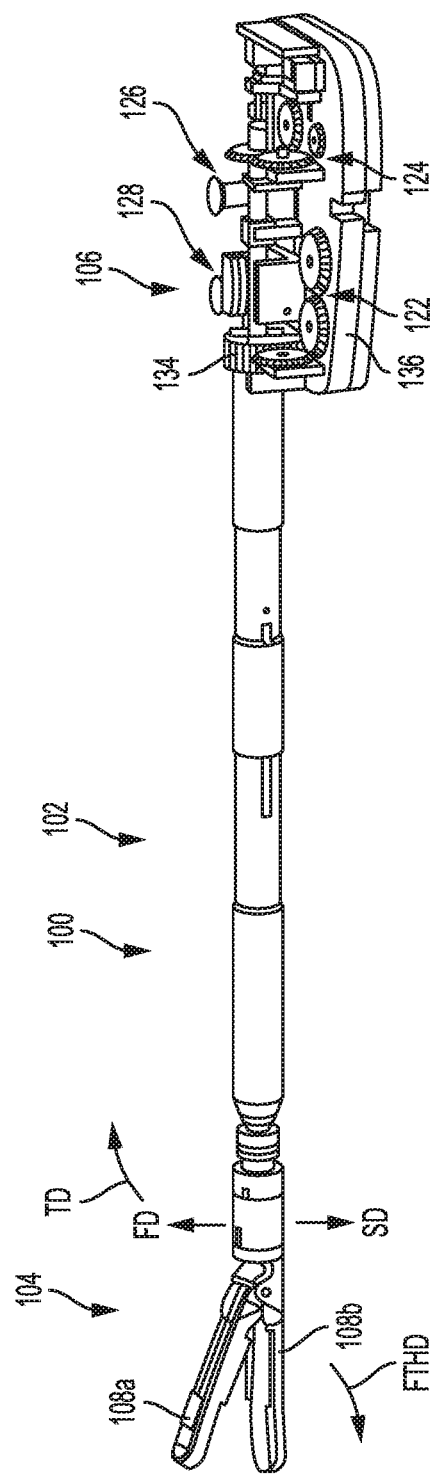
FIG. 1 is a perspective view of a portion of one embodiment of an electrosurgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary methods, systems, and devices for controlling electrosurgical tools are provided. In general, an electrosurgical tool is configured to apply energy to tissue, such as via an end effector of the surgical tool. The energy can include one or more types of energy, such as electrical energy, ultrasonic energy, and heat energy. The electrical energy can be a high frequency alternating current such as radiofrequency (RF) energy, or can be another type of electrical energy.

An exemplary electrosurgical tool can include a variety of features to facilitate application of energy as described herein. However, a person skilled in the art will appreciate that the electrosurgical tools can include only some of these features and/or can include a variety of other features known in the art. The electrosurgical tools described herein are merely intended to represent certain exemplary embodiments. Further, a person skilled in the art will appreciate that the electrosurgical tools described herein have application in conventional minimally-invasive and open surgical instrumentation as well as application in robotic-assisted surgery.

In an exemplary embodiment, an electrosurgical tool includes an elongate shaft, an end effector at a distal end of the elongate shaft, and a housing at a proximal end of the elongate shaft. The housing includes a drive system configured to operably couple to at least one motor for driving the drive system to cause performance of various functions of the surgical tool. The housing can be configured to be handheld and manually actuated by a user to actuate the drive system, or the housing can be configured to be operatively couple to a robotic surgical system configured to actuate the drive system. The at least one motor can be included as part of the electrosurgical tool, such as by being located in the housing, or the at least one motor can be separate and independent of the electrosurgical tool, such as the at least one motor being included in a tool housing of a robotic surgical system. The drive system is configured to operably couple to a control system configured to operably couple to the at least one motor. The control system can be included as part of the electrosurgical tool, such as by being located in the housing, or the control system can be separate and independent of the electrosurgical tool, such as the control system being included in a robotic surgical system. The control system is configured to actuate the at last one motor to thereby control actuation of the drive system.

Figure 2:
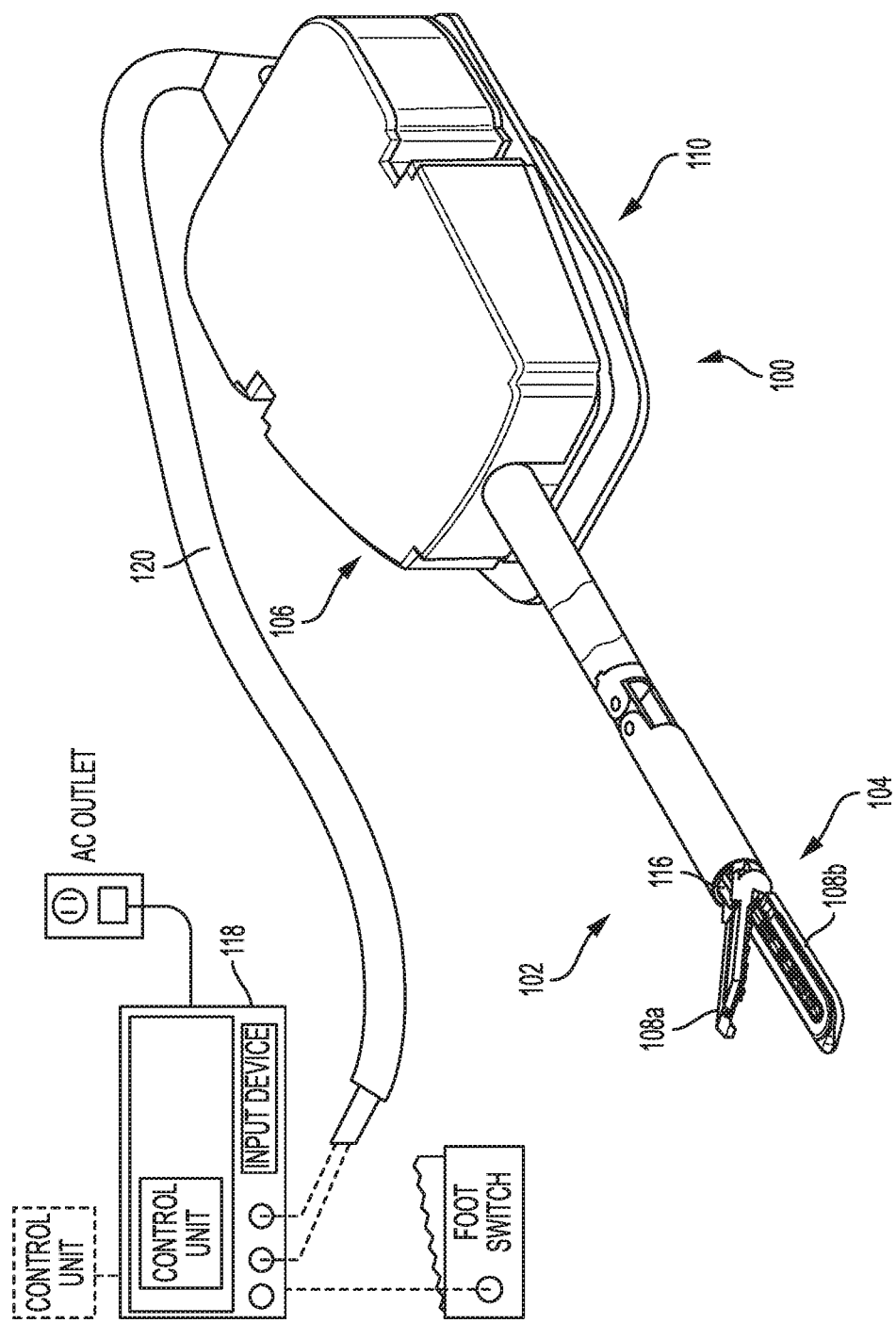
FIG. 2 is a perspective view of the tool of FIG. 1 coupled to a generator.

FIGS. 1 and 2 illustrate one embodiment of an electrosurgical tool 100. The tool 100 includes an elongate shaft 102, an end effector 104 coupled to a distal end of the shaft 102, and a proximal housing portion 106 including a housing 110 coupled to a proximal end of the shaft 102. For clarity of illustration, a portion of the housing 110 is omitted in FIG. 1. The end effector 104 in this illustrated embodiment includes first and second jaw members 108a, 108b, also referred to herein as "jaws," and is configured to move between an open position and a closed position. The end effector 104 is shown in the open position in FIGS. 1 and 2. The first and second jaw members 108a, 108b are straight, but in other embodiments the jaws can be curved. The jaw members 108a, 108b are configured to close to thereby capture or engage tissue so as to clamp or grasp the tissue therebetween. The first and second jaw members 108a, 108b can apply compression to the clamped tissue.

Figure 3:
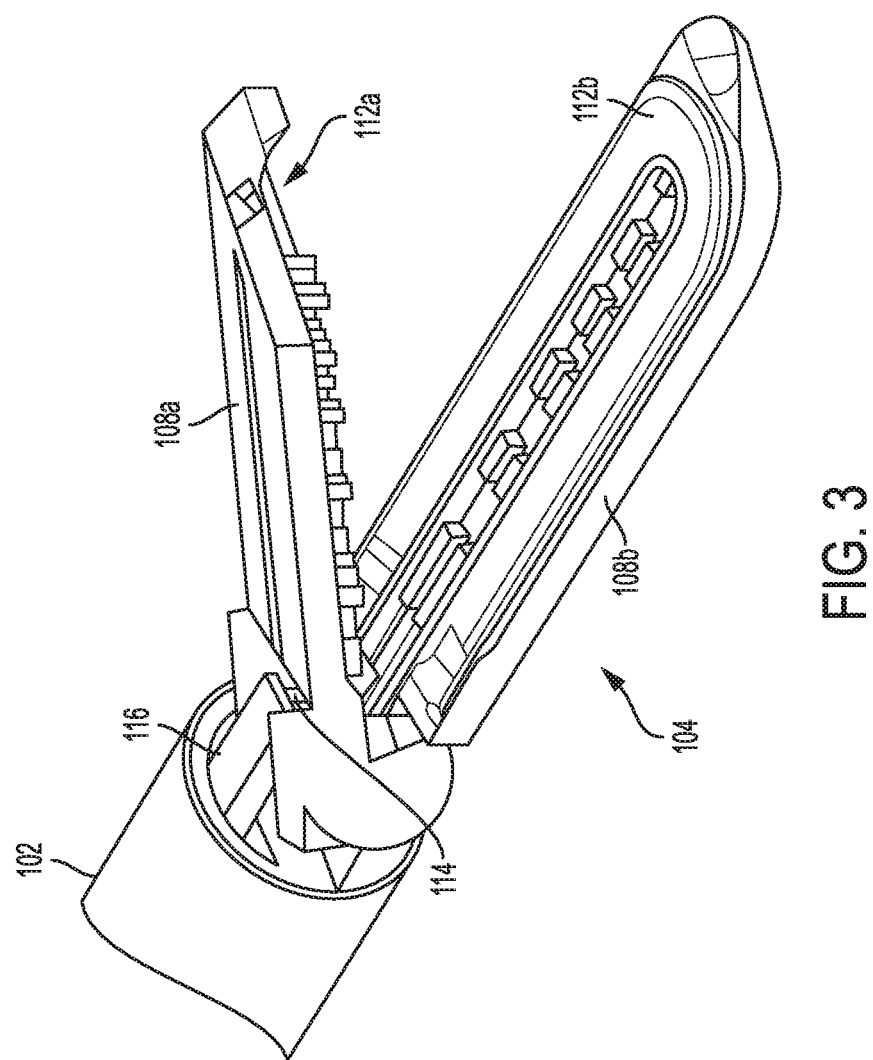
FIG. 3 is a perspective view of a distal portion of the tool of FIG. 1 with an end effector thereof open.

One or both of the jaw members 108a, 108b includes an electrode for providing electrosurgical energy to tissue. In an exemplary embodiment, each of the jaws 108a, 108b includes at least one electrode, e.g., the tool 100 is bipolar, such that electrical current can flow between the electrodes in the opposing jaw members 108a, 108b and through tissue positioned therebetween. In this illustrated embodiment, as shown in FIG. 3, the first jaw 108a has an electrode 112a on a tissue-facing surface thereof and the second jaw 108b has an electrode 112b on a tissue-facing surface thereof. The electrodes 112a, 112b are configured to be positioned against and/or positioned relative to tissue such that electrical current can flow through the tissue. The electrical current may generate heat in the tissue that, in turn, causes one or more hemostatic seals to form within the tissue and/or between tissues. For example, tissue heating caused by the electrical current may at least partially denature proteins within the tissue. Such proteins, such as collagen, may be denatured into a proteinaceous amalgam that intermixes and fuses, or "coagulates" or "welds," together as the proteins renature. As the treated region heals over time, this biological "weld" may be reabsorbed by the body's wound healing process. As mentioned above, the energy applied can include high frequency alternating current such as RF energy. When applied to tissue, RF energy may cause ionic agitation or friction, increasing the temperature of the tissue. Various embodiments of applying RF energy are described further in U.S. Patent Publication No. 2012/0078139 entitled "Surgical Generator For Ultrasonic And Electrosurgical Devices" filed Oct. 3, 2011, U.S. Patent Publication No. 2012/0116379 entitled "Motor Driven Electrosurgical Device With Mechanical And Electrical Feedback" filed Jun. 2, 2011, and U.S. Patent Publication No. 2015/0209573 entitled "Surgical Devices Having Controlled Tissue Cutting And Sealing" filed Jan. 28, 2014, which are hereby incorporated by reference in their entireties.

Figure 4:
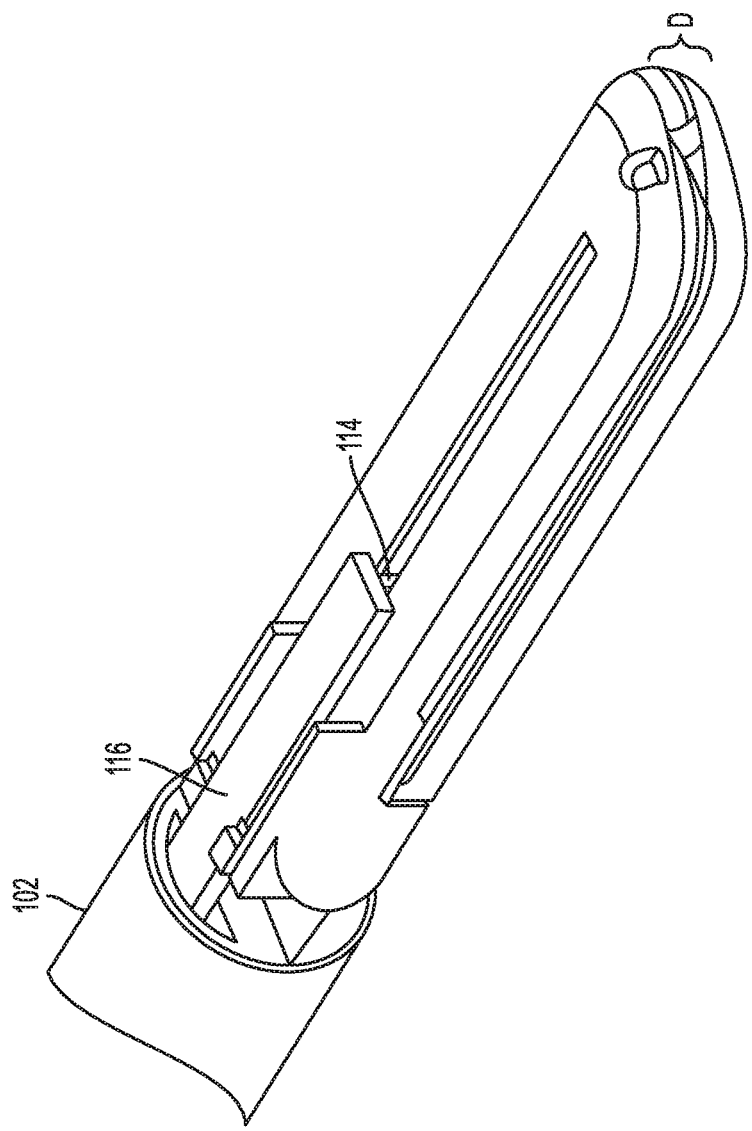
FIG. 4 is a perspective view of a distal portion of the tool of FIG. 1 with the end effector thereof closed.

As in this illustrated embodiment, as shown in FIG. 3, the tool 100 can include a cutting element 114, which is a knife on an I-beam 116 in this illustrated embodiment. The cutting element 114 is configured to translate along the end effector 104 and to cut or transect tissue positioned between the jaws 108a, 108b. The cutting can occur during or after the application of electrosurgical energy. The cutting element 114 is shown in FIG. 3 in a start position, e.g., a proximal-most position of the cutting element 114, before the cutting element 114 has begun to translate along the end effector 104. FIG. 4 shows the cutting element 114 advanced a distance distally along the end effector 104, which is shown in the closed position. In the closed position, the jaws 108a, 108b define a gap or dimension D between the tissue-facing surfaces thereof. In various embodiments, the dimension D can be in a range from about 0.0005" to about 0.040", for example, and in some embodiments, in a range of about 0.001" to about 0.010", for example.

Distal and proximal translation of the I-beam 116 along the end effector 114 is configured to open and close the jaw members 108a, 108b and thus when translating distally to cut, with the cutting element 114, tissue held between the jaw members 108a, 108b. In general, the I-beam 116 is a beam having an "I" cross-sectional shape.

The tool 100 is configured to operatively couple with a generator 118, as shown in FIG. 2 in which the tool 100 is operatively coupled with the generator 118. The tool 100 is connected to the generator 118 with a cable 120 in this illustrated embodiment but can connect thereto in other ways, as will be appreciated by a person skilled in the art. The generator 118 is configured as an energy source, e.g., an RF source, an ultrasonic source, a direct current source, etc., to deliver energy to the tool 100 to allow the electrodes 112, 112b to apply energy to tissue. As in this illustrated embodiment, the generator 118 can be coupled to a controller, such as a control unit. The control unit can be formed integrally with the generator 118 or can be provided as a separate and independent device electrically coupled to the generator 118 (shown in phantom in FIG. 2 to illustrate this option). The control unit is configured to regulate the energy delivered by generator 118 which in turn delivers energy to the first and second electrodes 112a, 112b. The energy delivery may be initiated in any suitable manner. In one embodiment, the electrosurgical tool 100 can be energized by the generator 118 via actuation of a foot switch. When actuated, the foot switch (or other actuated actuator) triggers the generator 118 to deliver energy to the end effector 104. The control unit can be configured to regulate the power generated by the generator 118, as discussed for example further below. As also discussed further below, the control unit as a separate and independent device from the generator 118 can be part of a robotic surgical system.

The generator 118 is shown separate and independent from the tool 100 in this illustrated embodiment, but in other embodiments the generator 118 (and/or the control unit) can be formed integrally with the tool 100 to form a unitary electrosurgical system. For example, a generator or equivalent circuit can be present at the proximal housing portion 106 within the housing 110.

Various configurations of electrodes and various configurations for coupling electrodes to the generator 118 are possible. As in this illustrated embodiment, the first and second electrodes 112a, 112b can be configured to be in electrical communication with the generator 118. The first electrode 112a on the first jaw member 108 can be configured to provide a return path for energy. In the illustrated embodiment and in functionally similar embodiments, other conductive parts of the tool 100 including, for example the jaw members 108a, 108b, the shaft 102, etc. may form all or a part of the return path. Also, it will be appreciated by a person skilled in the art that the supply electrode can be provided on the second jaw member 108b as shown or can be provided on the first jaw member 108a with the return electrode on the second jaw member 108b.

Figure 5:
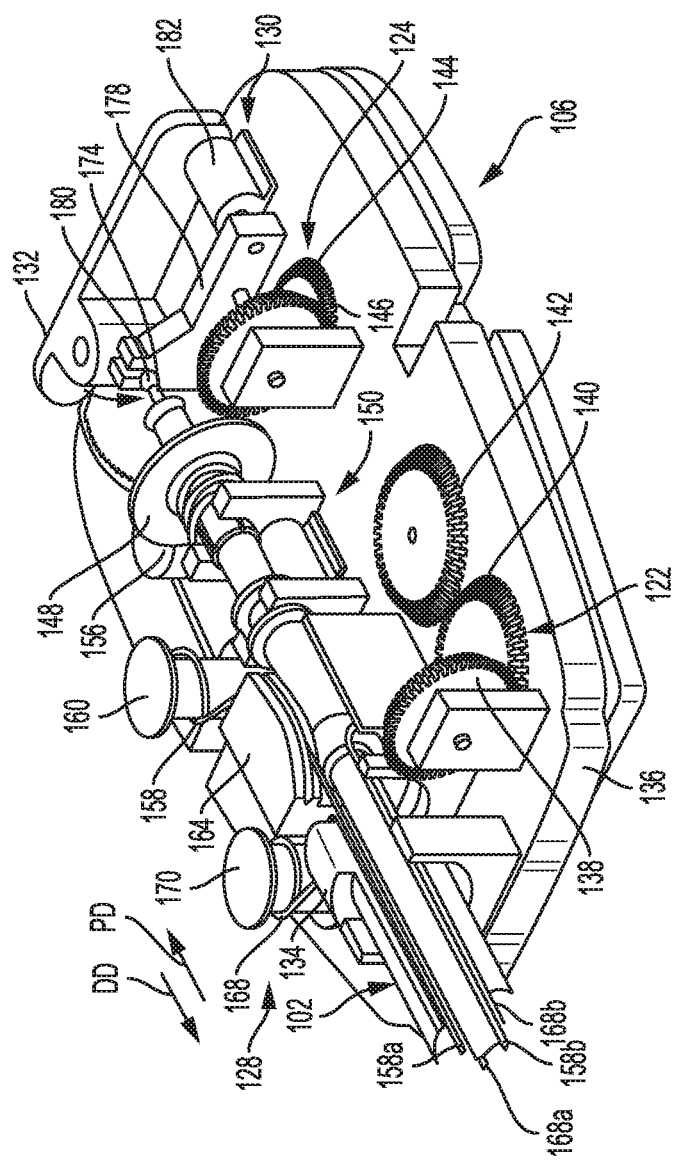
FIG. 5 is a perspective view of a proximal portion of the tool of FIG. 1.
Figure 6:
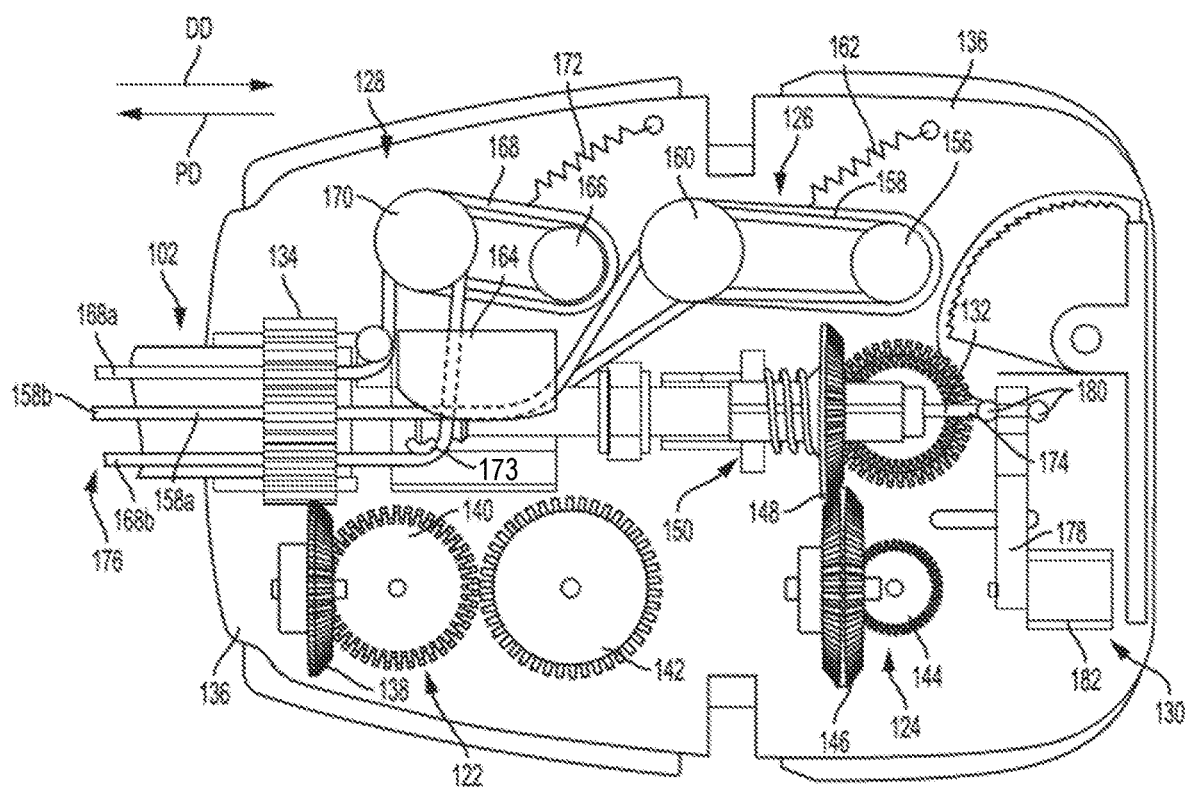
FIG. 6 is a top view of a proximal portion of the tool of FIG. 1.

The proximal housing portion 106, e.g., within the housing 110, includes a drive system configured to operably couple to at least one motor for driving the drive system to cause performance of various functions of the tool 100, such as closing of the jaws 108a, 108b, opening of the jaws 108a, 108b, articulating the end effector 104 relative to the shaft 102, rotating the shaft 102 about a longitudinal axis thereof, movement of the cutting element 114 along the end effector 104, and application of energy. As shown in FIGS. 1, 5, and 6, the tool 100 includes a drive system that includes a first drive system 122 configured to drive rotation of the shaft 102 (and thus also the end effector 104 at the shaft's distal end) about the shaft's longitudinal axis relative to the proximal housing portion 106, a second drive system 124 configured to drive rotation of the end effector 104 about the shaft's longitudinal axis relative to the shaft 102 and the proximal housing portion 106, a third drive system 126 configured to drive articulation of the end effector 104 in opposed first and second directions FD, SD relative to the shaft's longitudinal axis, a fourth drive system 128 configured to drive articulation of the end effector 104 in opposed third and fourth directions TD, FTHD relative to the shaft's longitudinal axis, and a fifth drive system 130 configured to drive a closure assembly to selectively cause opening and closing of the end effector 104. The third and fourth drive systems 126, 128 together define an articulation drive system. In an exemplary embodiment, each of the drive systems 122, 124, 126, 128, 130 is configured to have one motor operatively coupled thereto such that a rotary output motion from its associated motor drives the drive system.

The first drive system 122 is configured to receive a rotary output motion from a motor, e.g., a motor of a tool driver of a robotic surgical system when the tool driver is operatively coupled to the tool 100 via the proximal housing portion 106, and convert the rotary output motion to a rotary control motion to be applied to cause the rotation of the shaft 102 (and the end effector 104). The first drive system 122 includes a first rotation gear 134 formed on or attached to the shaft 102 that has a proximal end thereof rotatably support of a tool mounting plate 136 at the proximal housing portion 106, a second rotation gear 138 operatively engaged with the first rotation gear 134, a third rotation gear 140 operatively engaged with the second rotation gear 138, and a fourth rotation gear 142 operatively engaged with the third rotation gear 140. The fourth rotation gear 142 is operatively coupled to the motor such that the rotary output motion from the motor causes rotation of the fourth rotation gear 142 and, through the other three rotations gears 134, 138, 140, ultimately of the shaft 102 (and end effector 104).

The second drive system 124 is configured to receive a rotary output motion from a motor, e.g., a motor of a tool driver of a robotic surgical system when the tool driver is operatively coupled to the tool 100 via the proximal housing portion 106, and convert the rotary output motion to a rotary control motion to be applied to the end effector 104 to cause the rotation of the end effector 104. The second drive system 124 includes a first rotary gear 144, a second rotary gear 146 that is operatively engaged with the first rotary gear 144 and is rotatably supported on the tool mounting plate 136, a third rotary gear 148 that is selectively operatively engageable with the second rotary gear 146 via a shifting mechanism 150. The first rotary gear 144 is operatively coupled to the motor such that the rotary output motion from the motor causes rotation of the first rotary gear 144 and, through the other two rotary gears 146, 148 when operatively engaged with one another, ultimately of the end effector 104.

Figure 7:
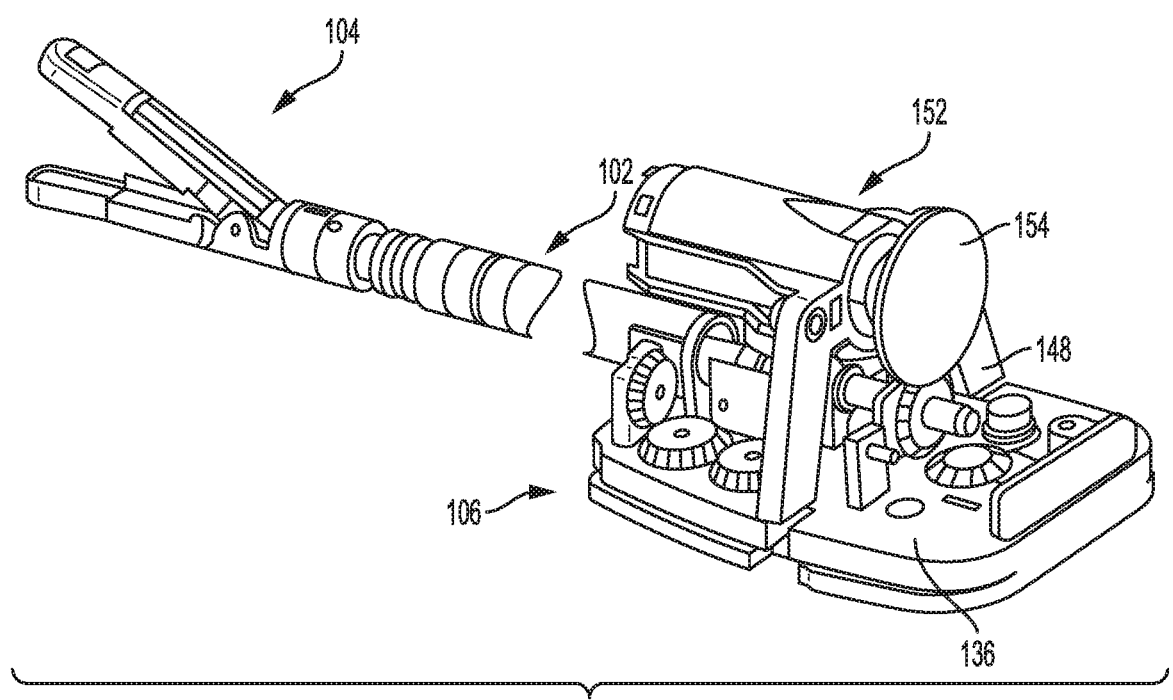
FIG. 7 is a perspective view of a portion of another embodiment of an electrosurgical tool.

FIG. 7 illustrates another embodiment of a second drive system configured to receive a rotary output motion from a motor 152 on board the tool 100 (e.g., within the housing 110) and convert the rotary output motion to a rotary control motion to be applied to the end effector 104 to cause the rotation of the end effector 104. Such arrangement can generate higher rotary output motions and torque, which may be advantageous when different forms of end effectors are employed. In this illustrated embodiment, the motor 152 is attached to the tool mounting plate 136 by a support structure 154 such that a driver gear (obscured by the support structure 154 in FIG. 7) that is coupled to the motor 152 is operatively engaged with the third rotary gear 148. As illustrated, the motor 152 is battery powered. In such an arrangement, the motor 152 is configured to be operatively coupled to a control system of a robotic surgical system 10 that controls the activation of the motor 152. In other embodiments, the motor 152 can be configured to be manually actuatable by an on/off switch (not shown) mounted on the motor 152 itself or on the proximal housing portion 106. In still other embodiments, the motor 152 can be configured to receive power and control signals from the robotic surgical system.

Referring again to FIGS. 1, 5, and 6, the third drive system 126 is configured to receive a rotary output motion from a motor, e.g., a motor of a tool driver of a robotic surgical system when the tool driver is operatively coupled to the tool 100 via the proximal housing portion 106, and convert the rotary output motion to a rotary control motion to be applied to the end effector 104 to selectively cause the articulation of the end effector 104 in the first and second directions FD, SD. The third drive system 126 includes a drive pulley 156 operatively engaged with a drive cable 158 that extends around a drive spindle assembly 160 that is pivotally mounted to the tool mounting plate 136. A tension spring 162 is attached between the drive spindle assembly 160 and the tool mounting plate 136 to maintain a desired amount of tension in the drive cable 158. A first end portion 158a of the drive cable 158 extends around an upper portion of a pulley block 164 that is attached to the tool mounting plate 136, and a second end portion 158b of the drive cable 158 extends around a sheave pulley or standoff on the pulley block 164. Application of a rotary output motion from the motor in a first direction will result in the rotation of the drive pulley 156 in a first direction and cause the cable end portions 158a, 158b to move in opposite directions to apply control motions to the end effector 104 or elongate shaft 102. That is, when the drive pulley 156 is rotated in a first rotary direction, the first cable end portion 158a moves in a distal direction DD and the second cable end portion 158b moves in a proximal direction PD. Rotation of the drive pulley 156 in an opposite rotary direction in response to a rotary output motion from the motor in a second direction (which is opposite to the first direction) results in the first cable end portion 158a moving in the proximal direction PD and the second cable end portion 158b moving in the distal direction DD. The end effector 104 can thus be selectively articulated in the opposed first and second directions FD, SD based on the direction of the motor's rotary output motion.

The fourth drive system 128 is configured to receive a rotary output motion from a motor, e.g., a motor of a tool driver of a robotic surgical system when the tool driver is operatively coupled to the tool 100 via the proximal housing portion 106, and convert the rotary output motion to a rotary control motion to be applied to the end effector 104 to cause the articulation of the end effector 104 in the third direction TD. The fourth drive system 128 includes a drive pulley 166 operatively engaged with a drive cable 168 that extends around a drive spindle assembly 170 that is pivotally mounted to the tool mounting plate 136. A tension spring 172 is attached between the drive spindle assembly 170 and the tool mounting plate 136 to maintain a desired amount of tension in the drive cable 168. A first cable end portion 168a of the drive cable 168 extends around a bottom portion of the pulley block 164, and a second cable end portion 168b extends around a sheave pulley or standoff 173 on the pulley block 164. Application of a rotary output motion from the motor in one direction will result in the rotation of the drive pulley 166 in one direction and cause the cable end portions 168a, 168b to move in opposite directions to apply control motions to the end effector 104 or elongate shaft 102. That is, when the drive pulley 166 is rotated in a first rotary direction, the first cable end portion 168a moves in the distal direction DD and the second cable end portion 168b moves in the proximal direction PD. Rotation of the drive pulley 166 in an opposite rotary direction result in the first cable end portion 168a moving in the proximal direction PD and the second cable end portion 168b to move in the distal direction DD. The end effector 104 can thus be selectively articulated in the opposed third and fourth directions TD, FTHD based on the direction of the motor's rotary output motion.

The fifth drive system 130 is configured to axially displace the closure assembly. The closure assembly includes a proximal drive rod segment 174 that extends through a proximal drive shaft segment 132 and a drive shaft assembly 176. A distal end of the proximal drive rod segment 174 is operatively coupled to a proximal end of the I-beam 116, either through direct connection or through indirect connection via one or more intermediate drive rod segments. A movable drive yoke 178 is slidably supported on the tool mounting plate 136. The proximal drive rod segment 174 is supported in the drive yoke 178 and has a pair of retainer balls 180 thereon such that shifting of the drive yoke 178 on the tool mounting plate 136 results in the axial movement of the proximal drive rod segment 174. A drive solenoid 182 operably couples with the drive yoke 178 and is configured to receive control power from the control system. Actuation of the drive solenoid 182 in a first direction will cause the closure assembly, e.g., the I-beam 116 and the proximal drive rod segment 174, to move in the distal direction DD and actuation of the drive solenoid 182 in a second direction will cause the closure assembly, e.g., the I-beam 116 and the proximal drive rod segment 174 to move in the proximal direction PD. The end effector 104 can thus be selectively opened (movement of the proximal drive rod segment 174 in one direction) and closed (movement of the proximal drive rod segment in the opposite direction).

FIGS. 8-11 illustrate another embodiment of an electrosurgical tool 200. The tool 200 is generally configured and used similar to the tool 100 of FIG. 1 and includes an elongate shaft 202, an end effector 204 coupled to a distal end of the shaft 202 and including first and second jaws 206a, 206b, at least one electrode at the end effector 204, a proximal housing portion (not shown) including a drive system and including a housing coupled to a proximal end of the shaft 202, an I-beam 208, and a cutting element 210. Similar to the proximal housing portion 106 of FIG. 1 discussed above, the proximal housing portion of the tool 200 can be configured to operably couple to a tool driver of a robotic surgical system, or the proximal housing portion can be configured to be handheld and operated manually. It will be appreciated by a person skilled in the art that the tool 200 can contain and/or can be configured to operatively connect to a generator for generating an electrosurgical drive signal to drive the tool's drive system, which as discussed above can include multiple drive systems.

The tool 200 also has a closure assembly configured and used similar to the closure assembly of the tool 100 of FIG. 1. In this illustrated embodiment, the closure assembly includes the I-beam 208, a rotary drive member 222 that extends proximally from the I-beam 208, and a rotary drive shaft 212 movably disposed in the elongate shaft 202 and operatively coupled to the rotary drive member 222. The rotary drive shaft 212 is operatively coupled to a drive system of the tool that is configured to drive the closure assembly, e.g., by a motor operatively coupled to the drive system providing rotational and axial translational motion to the rotary drive shaft 212.

Figure 8:
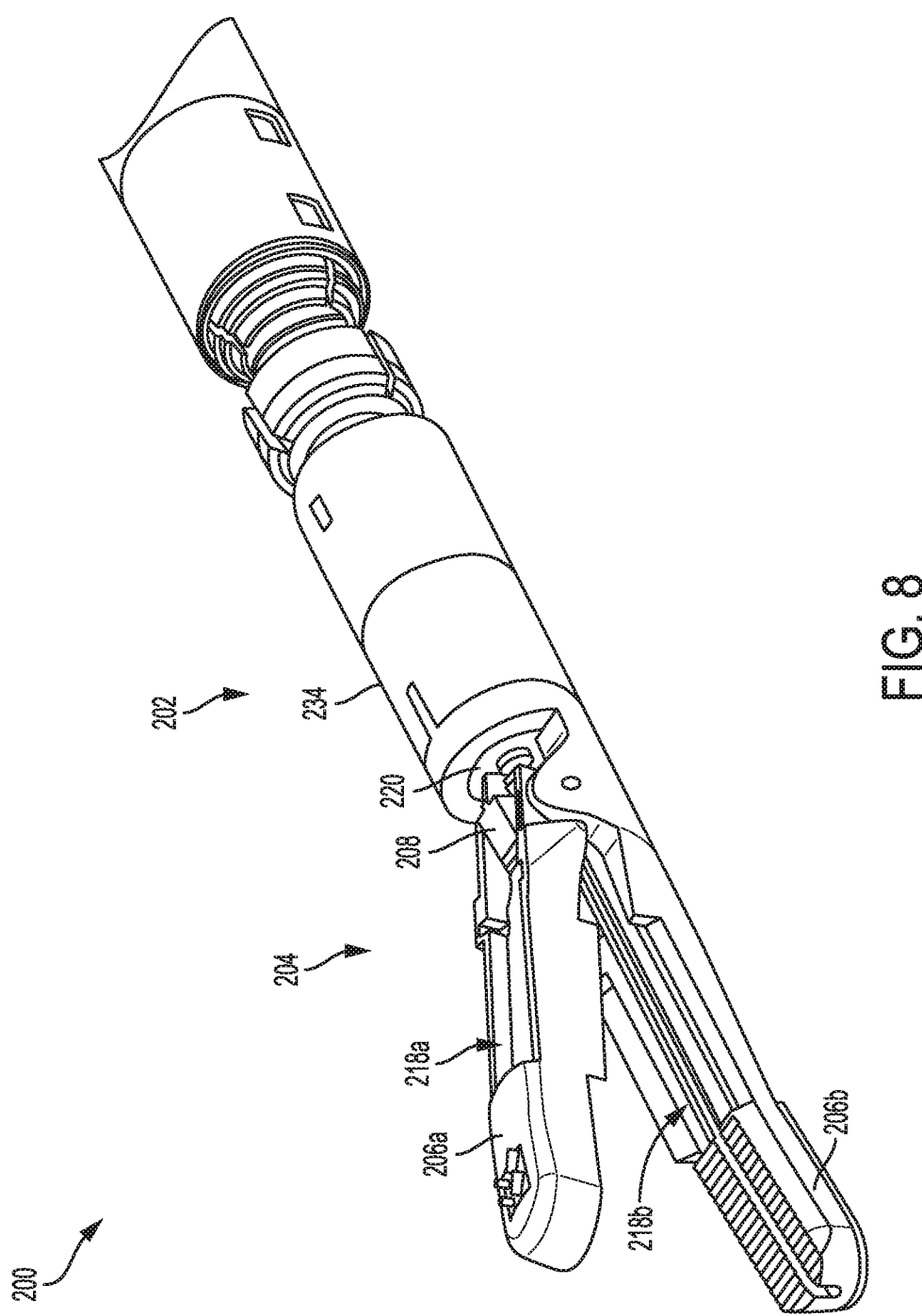
FIG. 8 is a perspective view of a distal portion of another embodiment of an electrosurgical tool.

The I-beam 208 has a first I-beam flange 214a and a second I-beam flange 214b that are connected with an intermediate portion 216. The cutting element 210 is a distal-facing sharp edge or blade on the intermediate portion 216 of the I-beam 208 in this illustrated embodiment. The I-beam 208 is configured to translate within a first channel 218a in the first jaw member 206a, e.g., with the first flange 214a moving within the first channel 218a, and within a second channel 218b in the second jaw member 206b, e.g., with the second flange 214b moving within the second channel 218b. As the I-beam 208 is advanced distally, the first jaw 206a is moved toward the second jaw 206b to move the end effector 204 to the closed position. FIGS. 8 and 10 show the end effector 204 in the open position and show the I-beam 208 and cutting element 210 in their start or proximal-most positions. FIG. 11 shows the end effector 204 in the closed position and show the I-beam 208 and cutting element 210 in their end or distal-most positions. After a distal translation stroke, the I-beam 208 and the cutting element 210 can be proximally refracted back to their start positions, which will move the end effector 204 from the closed position to the open position.

Figure 9:
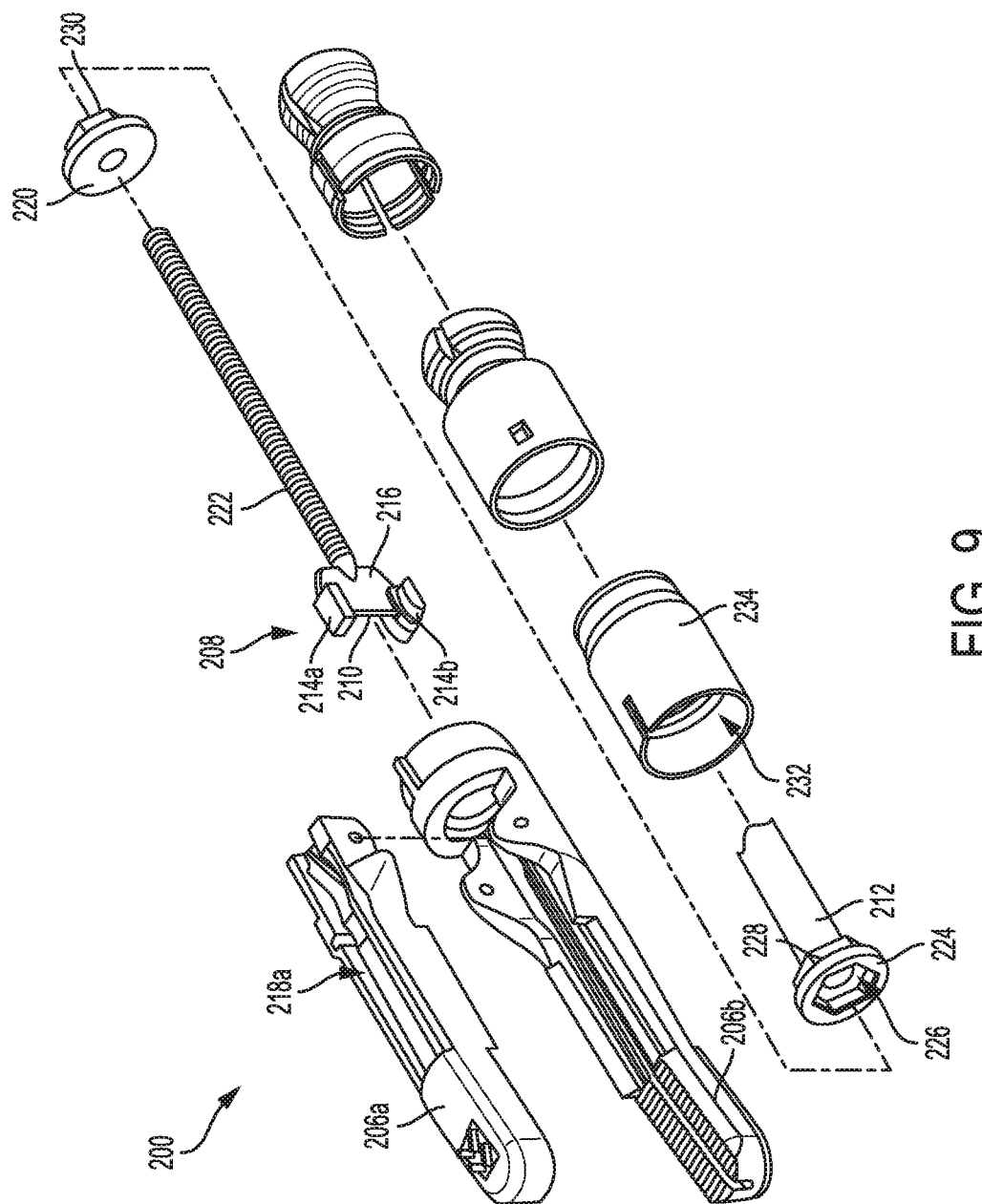
FIG. 9 is an exploded view of a distal portion of the tool of FIG. 8.

As shown in FIGS. 9-11, a threaded rotary drive nut 220 is threaded onto the rotary drive member 222. The threaded rotary drive nut 220 is seated in the second jaw 206b. The threaded rotary drive nut 220 is mechanically constrained from translation in any direction, but the threaded rotary drive nut 220 is rotatable within the second jaw 206b. Therefore, given the threaded engagement of the rotary drive nut 220 and the threaded rotary drive member 222, rotational motion of the rotary drive nut 220 is transformed into translational motion of the threaded rotary drive member 222 in the longitudinal direction and, in turn, into translational motion of the I-beam 208, and hence the cutting element 210, in the longitudinal direction.

The threaded rotary drive member 222 is threaded through the rotary drive nut 220 and is located inside a lumen of the rotary drive shaft 212. The threaded rotary drive member 222 is not attached or connected to the rotary drive shaft 212. The threaded rotary drive member 222 is freely movable within the lumen of the rotary drive shaft 212 and is configured to translate within the lumen of the rotary drive shaft 212 when driven by rotation of the rotary drive nut 220.

The rotary drive shaft 212 a rotary drive head 224. The rotary drive head 224 has a female hex coupling portion 226 on a distal side of the rotary drive head 224, and the rotary drive head 224 has a male hex coupling portion 228 on a proximal side of the rotary drive head 224. The distal female hex coupling portion 226 of the rotary drive head 224 is configured to mechanically engage with a male hex coupling portion 230 of the rotary drive nut 220 located on a proximal side of the rotary drive nut 220. The proximal male hex coupling portion 228 of the rotary drive head 224 is configured to mechanically engage with a female hex shaft coupling portion 232 of an end effector drive housing 234 at a proximal end of the end effector 204.

When the rotary drive shaft 212 is in a distal-most position, the female hex coupling portion 226 of the rotary drive head 224 is mechanically engaged with the male hex coupling portion 230 of the rotary drive nut 220. In this configuration, rotation of the rotary drive shaft 212 actuates rotation of the rotary drive nut 220, which actuates translation of the threaded rotary drive member 222, which actuates translation of the I-beam 208 and cutting element 210. The orientation of the threading of the threaded rotary drive member 222 and the rotary drive nut 220 may be established so that either clockwise or counterclockwise rotation of the rotary drive shaft 212 will actuate distal or proximal translation of the threaded rotary drive member 222, I-beam 208, and cutting element 210. In this manner, the direction, speed, and duration of rotation of the rotary drive shaft 212 can be controlled in order to control the direction, speed, and magnitude of the longitudinal translation of the I-beam 208 and cutting element 210 and, therefore, the closing and opening of the end effector 204 and the transection stroke of the I-beam 208 along the first and second channels 218a, 218b, as described above. In this illustrated embodiment, rotation of the rotary drive shaft 212 in a clockwise direction (as viewed from a proximal-to-distal vantage point) actuates clockwise rotation of the rotary drive nut 220, which actuates distal translation of the threaded rotary drive member 222, which actuates distal translation of the I-beam 208 and cutting element 210, which actuates closure of the end effector 204 and a distal transection stroke of the I-beam 208 and cutting element 210. Rotation of the rotary drive shaft 212 in a counterclockwise direction provides the opposite effect, with the I-beam 208 and cutting element 210 translating proximally.

FIGS. 10 and 11 show the rotary drive shaft 212 in a proximal-most position in which the male hex coupling portion 228 of the rotary drive head 224 is mechanically engaged with the female hex shaft coupling portion 232 of the end effector drive housing 234. In this configuration, rotation of the rotary drive shaft 212 actuates rotation of the end effector 204 relative to the shaft 202. Thus, the rotary drive shaft 212 may be used to independently actuate the opening and closing of the end effector 204, the proximal-distal transection stroke of the I-beam 208 and cutting element 210, and the rotation of end effector 204.

FIGS. 12-15 illustrate another embodiment of an electrosurgical tool 300. The tool 300 is generally configured and used similar to the tool 100 of FIG. 1 and includes an elongate shaft 302, an end effector 304 coupled to a distal end of the shaft 302 and including first and second jaws 306a, 306b, and a proximal housing portion 330 (see FIGS. 16 and 17) including a drive system and including a housing coupled to a proximal end of the shaft 302. Similar to the proximal housing portion 106 of FIG. 1 discussed above, the proximal housing portion of the tool 300 can be configured to operably couple to a tool driver of a robotic surgical system, or the proximal housing portion can be configured to be handheld and operated manually. It will be appreciated by a person skilled in the art that the tool 300 can contain and/or can be configured to operatively connect to a generator for generating an electrosurgical drive signal to drive the tool's drive system, which as discussed above can include multiple drive systems. In this illustrated embodiment, tissue-facing surfaces of each of the jaws 306a, 306b are conductive and are configured to apply energy to tissue engaged thereby.

The tool 300 includes cables 308, 310, 312, 314 that are configured to be actuated to selectively cause opening of the end effector 304, closing of the end effector 304, and articulation of the end effector 304 relative to the shaft 302. The cables 308, 310, 312, 314 are attached to the end effector 304, extend along solid surfaces of guide channels in the end effector 304, a distal clevis 316, and a proximal clevis 318, and from there extend back through the shaft 302 to a the proximal housing portion.

The distal clevis 316 is configured to rotate 322 about a pin 324 that defines a pitch axis, e.g., the distal clevis is configured to rotate about the pitch axis in response to cable actuation. For clockwise rotation about the pitch axis, a drive system in response to control thereof, e.g., in response to motor force delivered thereto, pulls in identical lengths of the third and fourth cables 312, 314 while releasing the same lengths of the first and second cables 308, 310. The third and fourth cables 312, 314 apply forces to the distal clevis 316 at moment arms defined by guide channels of the third and fourth cables 312, 314 through the distal clevis 316. Similarly, for counterclockwise rotation of the distal clevis 316 about the pitch axis, the drive system in response to control thereof pulls in identical lengths of the first and second cables 308, 310 while releasing the same lengths of the third and fourth cables 312, 314.

A pin 320 in distal clevis 316 is perpendicular to the pin 324 and defines a pivot or yaw axis, about which the end effector 304 is configured to rotate 326 and about which the jaws 306a, 306b are configured to individually rotate 328 to open and close in response to cable actuation. The first and second cables 308, 310 attach to the first jaw 306a, and the third and fourth cables 312, 314 attach to the second jaw 306b. The attachment of the first and second cables 308, 310 to jaw 242 is such that pulling in a length of one cable 308 or 310 while releasing the same length of the other cable 308 or 310 causes the first jaw 306a to rotate about the pin 320. Similarly, the attachment of the third and fourth cables 312, 314 to the second jaw 306b is such that pulling in a length of one cable 312 or 314 while releasing the same length of the other cable 312 or 314 causes the second jaw 306b to rotate about the pin 320. A closure assembly of the tool 300 thus includes the cables 308, 310, 312, 314.

Figure 15:
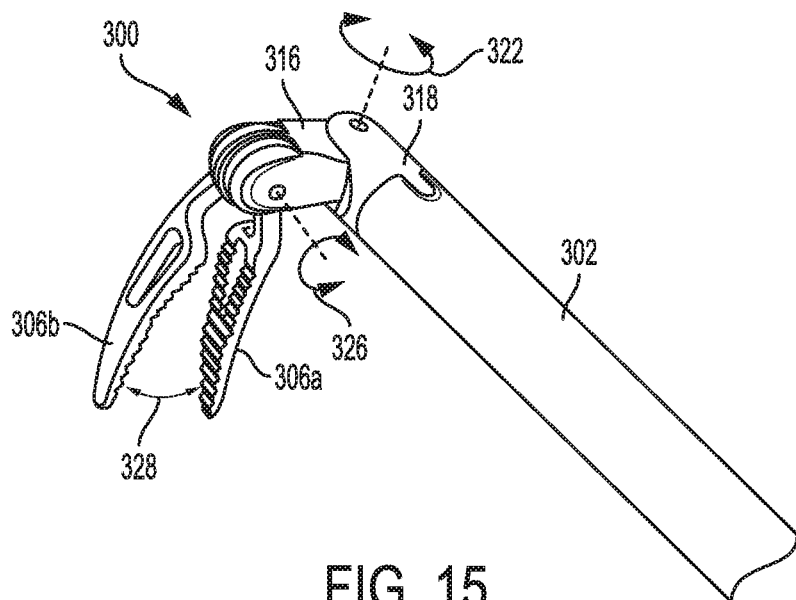
FIG. 15 is yet another perspective view of a distal portion of the tool of FIG. 12.

Yaw rotations, i.e., rotations 326 in FIG. 15, correspond to both rotating the jaws 306a, 306b in the same direction and through the same angle. In particular, the drive system pulling in a length of the second cable 310 and releasing an equal length of the first cable 308 will cause the first jaw 306a to rotate in a clockwise direction about the axis of pin 320. For this rotation, a guide channel in the first jaw 306a defines the moment arm at which the second cable 310 applies a force to the first jaw 306a, and the resulting torque causes the first jaw 306a to rotate clockwise and the first and second cables 308, 310 to slide on the solid surface of guide channels in distal clevis 316. If at the same time the drive system pulls in a length of the fourth cable 314 and releases the same length of the third cable 312, the second jaw 306b will rotate clockwise through an angle that is the same as the angle through which the first jaw 306a rotates. Accordingly, the jaws 306a, 306b maintain their positions relative to each other and rotate as a unit through a yaw angle. Counter-clockwise rotation of the effector 304 including the jaws 306a, 306b is similarly accomplished when the drive system pulls in equal lengths of the first and third cables 308, 312 while releasing the same lengths of the second and fourth cables 310, 314.

Opening/closing of the end effector 304, i.e., rotations 328 in FIG. 15, are achieved by rotating the jaws 306a, 306b in opposite directions by the same amount. To open the grip of the jaws 306a, 306b, the drive system pulls in equal lengths of the first and fourth cables 308, 314 while releasing the same lengths of the second and third cables 310, 312, causing the jaws 306a, 306b to rotate in opposite directions away from each other. To close the grip of the jaws 306a, 306b, the drive system pulls in equal lengths of the second and third cables 310, 312 while releasing the same lengths of the first and fourth cables 310, 312, causing the jaws 306a, 306b to rotate in opposite directions toward each other. When the tissue-facing surfaces of the jaws 306a, 306b come into contact or are clamped on tissue, the tension in the second and third cables 252 and 253 can be kept greater than the tension in the first and fourth cables 308, 314 in order to maintain gripping forces.

Figure 16:
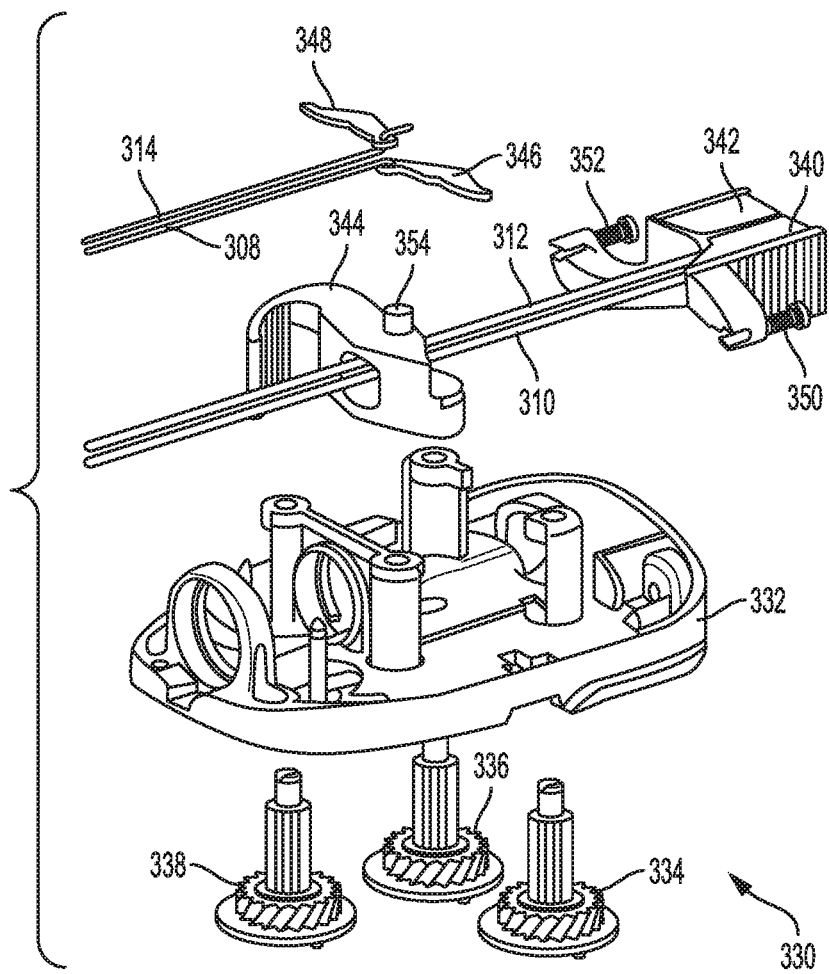
FIG. 16 is an exploded view of a proximal portion of the tool of FIG. 12.
Figure 17:
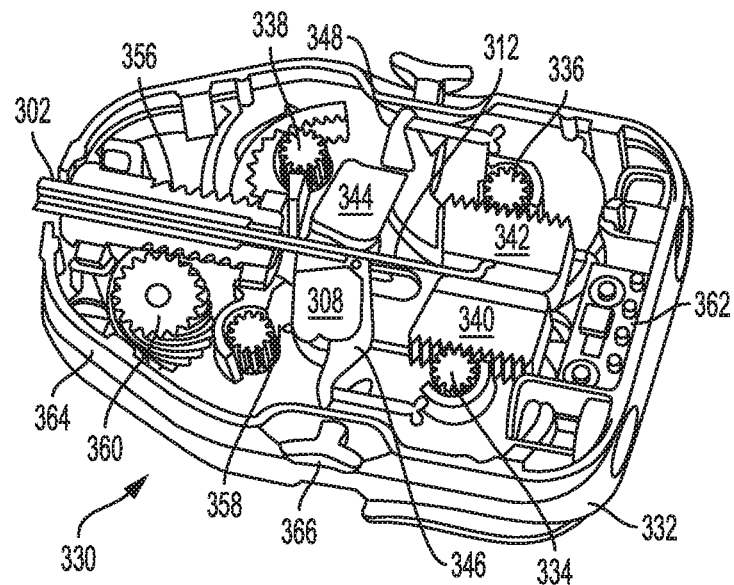
FIG. 17 is a perspective view of a proximal portion of the tool of FIG. 12.

FIGS. 16 and 17 illustrate portions of the proximal housing portion 330 of the tool 300. The proximal housing portion 330 includes a housing or chassis 332, three drive shafts 334, 336, 338, three toothed components 340, 342, 344, and two levers 346, 348, and the proximal housing portion 330 couples to the four cables 308, 310, 312, 314. The drive shafts 334, 336, 338 are configured to operatively connect to motors of a control system that drive the drive shafts 334, 336, 338.

The first drive shaft 334 acts as a pinion that engages a rack portion of the first toothed component 340. The first toothed component 340 is attached to the second cable 310 and moves in a straight line to pull in or release a length of second cable 310 as the drive shaft 334 turns. The first toothed component 340 also includes an arm containing an adjustment screw 350 that contacts the first lever 346. In particular, the adjustment screw 350 contacts the first lever 346 at an end opposite to where the first cable 308 attaches to the first lever 346. A pivot point or fulcrum for the first lever 346 is on the third toothed component 344 that acts as a rocker arm as described further below. In operation, as the first toothed component 340 moves, the adjustment screw 350 causes or permits rotation of the first lever 346 about the pivot point so that the lever 346 can pull in or release the first cable 308. The connection of the first cable 308 to the first lever 346 and the contact point of the adjustment screw 350 on the first lever 346 can be made equidistant from the pivot point of the first lever 346, so that when the first toothed component 346 pulls in (or releases) a length of the second cable 310, the first lever 346 releases (or pulls in) the same length of the first cable 308. The first adjustment screw 350 permits adjustment of the tension in the first and second cables 308, 310 by controlling the orientation of the first lever 346 relative to the position of the first toothed component 340.

The second drive shaft 336 similarly acts as a pinion that engages a rack portion of the second toothed component 342. The second toothed component 340 is attached to the third drive cable 310 and moves in a straight line to pull in or release a length of the third cable 310 as the second drive shaft 336 turns. The first toothed component 340 also includes an arm containing a second adjustment screw 352 that contacts the second lever 348 at an end opposite to where the fourth cable 314 attaches to the second lever 348. A pivot point or fulcrum for the second lever 348 is on the third toothed component 344, and the distance of the connection of the fourth cable 314 from the pivot point of the second lever 348 can be made the same as the distance from the pivot point of the second lever 348 to the contact point of the second adjustment screw 352 on the second lever 348. As a result, when the second toothed component 342 pulls in (or releases) a length of the third cable 312, the second lever 348 releases (or pulls in) the same length of the fourth cable 314. The second adjustment screw 352 permits adjustment of the tension in the third and fourth cables 312, 314 by controlling the orientation of the second lever 348 relative to the position of the second toothed component 342.

The first and second drive shafts 334, 336 can be operated to change the yaw angle or the grip of a wrist mechanism using the processes described above. For example, turning the first and second drive shafts 334, 336 at the same speed in the same direction or in opposite directions will change the grip or yaw.

The third drive shaft 338 engages an internal sector gear portion of the third toothed component 344. The third toothed component 334 has a pivot attached to the chassis 332, so that as the third drive shaft 338 turns, the third toothed component 344 rotates about pivot pin 354. The third toothed component 344 also includes protrusions (not visible in FIG. 16) that act as pivot points for the levers 346, 348. If the first and second toothed components 340, 342 are moved at the appropriate speeds and directions to maintain the orientations of the levers 346, 348, rotation of the third toothed component 344 will pull in (or release) equal lengths of the first and second cables 308, 310 and release (or pull in) the same lengths of the third and fourth cables 312, 314.

As shown in FIG. 16, the shaft 302 is attached in the proximal housing portion 330 to a helical gear 356, which is coupled to a drive shaft 358 through an intervening helical gear 360. When a control system rotates the drive shaft 358, the helical gears 356, 360 rotate the shaft 302 and thereby change the roll angle of the end effector 304 at the distal end of the shaft 302.

The proximal housing portion 330 also includes a circuit board 362 configured for electrical connection to a control system of a robotic surgical system. The circuit board 362 can include memory or other circuitry that sends an identification signal to the control system to indicate which instrument is connected to the control system and/or to provide key parameters that the control system may need for proper operation of the instrument. Connection to electrical components of the end effector 304, e.g., to energize a cauterizing instrument or to relay sensor measurements, can be in the circuit board 362. However, a separate electrical connection may be desired for energizing the end effector 304, particularly when high voltages are required.

The proximal housing portion 330 also includes a cover 364 that encloses mechanical and electrical components of the proximal housing portion 330. Two levers 366 can be used to disengage the proximal housing portion 330 from the control system.

Figure 18:
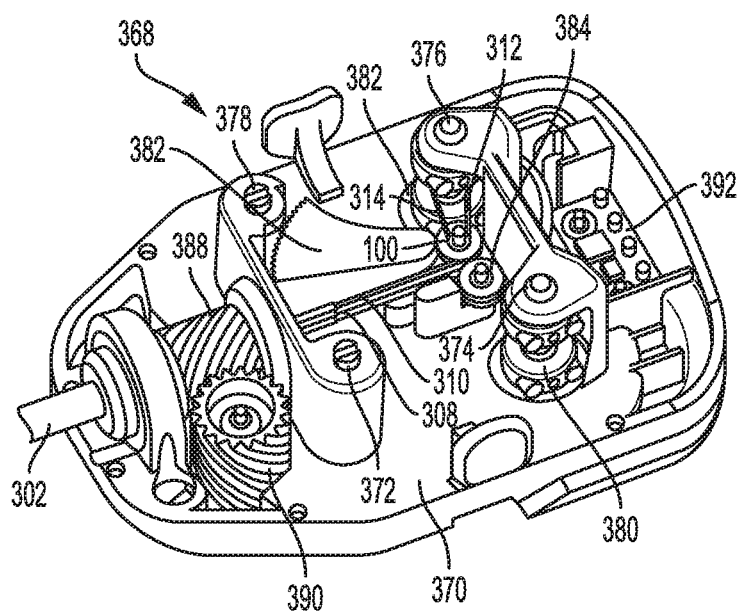
FIG. 18 is a perspective view of another embodiment of a proximal portion of an electrosurgical tool.

Pulleys and capstans can be used in place of some toothed components of FIGS. 16 and 17. FIG. 18 illustrates another embodiment of a proximal housing portion 368 that includes pulleys and capstans but is otherwise generally configured and used similar to the proximal housing portion 330 of FIGS. 16 and 17. The proximal housing portion 368 includes a housing or chassis 370, four drive shafts 372, 374, 376, 378, a pair of capstans 380, 382, a rocker arm 382 on which a first pair of pulleys 384 and a second pair of pulleys 386 are mounted, helical gears 388, 390, and a circuit board 392. The four cables 308, 310, 312, 314 extend through the shaft 302 into the proximal housing portion 368.

The first and second cables 308, 310 pass from the shaft 302, wind around one or more first pulleys 384, and wrap around the first capstan 380. The wrapping of the first and second cables 308, 310 around the capstan 380 is such that when the first capstan 380 turns, a length of one cable 308, 310 is pulled in and an equal length of the other the cable 308, 310 fed out. Similarly, the third and fourth cables 312, 314 pass from the shaft 302, wind around one or more second pulleys 386, and are wrapped around the second capstan 382, so that when the second capstan 382 turns a length of one cable 312, 314 is pulled in and an equal length of the other cable 312, 314 is fed out. The second and third drive shafts 374, 376 are respectively coupled to turn the capstans 380, 382. A control system can thus turn the second and third drive shafts 374, 376 to change the yaw angle or the grip using the processes described above.

As mentioned above, the pulleys 384, 386 are mounted on the rocker arm 382. The rocker arm 382 has a sector gear portion that engages the fourth drive shaft 378 and is coupled to the chassis 370 to rotate or rock about a pivot axis when the fourth drive shaft 378 turns. The sector gear portion and pivot of the rocker arm 382 are designed so that rotation of the rocker arm 382 primarily causes one set of pulleys 384 or 386 to move toward its associated capstan 380 or 382 and the other set of pulleys 384 or 386 to move away from its associated capstan 380 or 382. This effectively pulls in lengths of one pair of cables 308, 310 or 312, 314 and releases an equal length of the other pair of cables 314, 312 or 308, 310. Rotation of the fourth drive shaft 378 can thus change the pitch.

Using the first drive shaft 372 to turn the helical gears 388, 390 can control roll angle as described above.

The circuit board 392 provides an interface to a control system as described above. High voltage connections are generally made through separate electrical connections and wires that may be run through the proximal housing portion 368 and run through the shaft 302 to the end effector 304.

For example, in one embodiment of the invention, the tool 300 is a bipolar cautery instrument and electrical wires or other electrical conductors (not shown) connect to a generator through connectors (not shown) on the proximal housing portion 368 and from there run with the cables 308, 310, 312, 314 through the shaft 302. Electrical energy for cautery can be delivered through contacts, which engage the jaws 306a, 306b similar to brushes in a motor.

Embodiments of electrosurgical tools are further described in U.S. Pat. No. 9,119,657 entitled "Rotary Actuatable Closure Arrangement For Surgical End Effector" filed Jun. 28, 2012 and U.S. Pat. No. 8,771,270 entitled "Bipolar Cautery Instrument" filed Jul. 16, 2008, which are hereby incorporated by reference in their entireties.

As mentioned above, the electrosurgical tools discussed herein can be manually operated or electrically operated. More and more surgical procedures are being performed using electrically-powered surgical devices that are either hand-held or that are coupled to a surgical robotic system.

In general, one or more motors can be used to drive various electrosurgical device functions. The device functions can vary based on the particular type of electrosurgical device, but in general an electrosurgical device can include one or more drive systems that can be configured to cause a particular action or motion to occur, such as shaft and/or end effector rotation, end effector articulation, jaw opening and/or closing, energy delivery, etc. Each drive system can include various components, as discussed above, such as one or more gears that receive a rotational force from the motor(s) and that transfer the rotational force to one or more drive shafts to cause rotary or linear motion of the drive shaft(s). The motor(s) can be located within the electrosurgical device itself or, in the alternative, coupled to the electrosurgical device such as via a robotic surgical system. Each motor can include a rotary motor shaft that is configured to couple to the one or more drive systems of the electrosurgical device so that the motor can actuate the drive system(s) to cause a variety of movements and actions of the electrosurgical device.

It should be noted that any number of motors can be used for driving any one or more drive systems on a surgical device. For example, one motor can be used to actuate two different drive systems for causing different motions. Moreover, in certain embodiments, the drive system can include a shift assembly for shifting the drive system between different modes for causing different actions. A single motor can in other aspects be coupled to a single drive assembly. An electrosurgical device can include any number of drive systems and any number of motors for actuating the various drive systems. The motor(s) can be powered using various techniques, such as by a battery on the electrosurgical device or by a power source connected directly to the electrosurgical device or connected through a robotic surgical system.

Additional components, such as one or more sensors or one or more meter devices, can be coupled to the motor(s) in order to determine and/or monitor at least one of displacement of a drive system coupled to the motor or a force on the motor during actuation of the drive system. For example, an electrosurgical tool can include one or more sensors or one or more meter devices and can include a control unit (e.g., a circuit board or computer system including a processor) configured to transmit sensed/metered data to a control system that controls the motor. Embodiments of surgical device control units configured to transmit sensed/metered data are further described in previously mentioned U.S. Pat. No. 8,771,270 entitled "Bipolar Cautery Instrument" filed Jul. 16, 2008. Embodiments of position sensors (e.g., a Hall Effect sensor) to determine cutting element position along an end effector, embodiments of firing sensors (e.g., a rheostat or variable resistor) to determine when a firing trigger or other firing actuator has been actuated to start a motor to drive firing, embodiments of closure sensors (e.g., a digital sensor or an analog sensor) to determine when a closure trigger or other closure actuator has been actuated to start a motor to drive closure, embodiments of load sensors (e.g., a pressure sensor) to determine closure pressure force exerted by an end effector, embodiments of force sensors to determine user-applied force to the device's actuator to adjust an amount of power provided by a motor based on an amount of the user-applied force, embodiments of sensors (e.g., a position switch, a Hall Effect sensor, or an optical sensor) to determine an angle of the end effector's closure, and embodiments of impedance sensors to measure impedance of clamped tissue are variously described in U.S. Patent Publication No. 2012/0292367 entitled "Robotically-Controlled End Effector" filed Feb. 13, 2012, U.S. Patent Publication No. 2015/0209059 entitled "Methods And Devices For Controlling Motorized Surgical Devices" filed Jan. 28, 2014, U.S. Pat. No. 5,558,671 entitled "Impedance Feedback Monitor For Electrosurgical Instrument" filed Sep. 24, 1996, and U.S. Patent Publication No. 2015/0209573 entitled "Surgical Devices Having Controlled Tissue Cutting And Sealing," which are hereby incorporated by reference in their entireties.

In certain embodiments, when the at least one motor is activated, its corresponding rotary motor shaft drives the rotation of at least one corresponding gear assembly located within a drive system of an electrosurgical tool. The corresponding gear assembly can be coupled to at least one corresponding drive shaft, thereby causing linear and/or rotational movement of the at least corresponding drive shaft. While movement of two or more drive shafts can overlap during different stages of operation of the drive system, each motor can be activated independently from each other such that movement of each corresponding drive shaft does not necessarily occur at the same time or during the same stage of operation.

When the at least one drive shaft is being driven by its corresponding motor, a rotary encoder, used, can determine the rotational position of the motor, thereby indicating linear or rotational displacement of the at least one drive shaft. The rotary encoder can be coupled to the motor to monitor the rotational position of the motor, thereby monitoring a rotational or linear movement of a respective drive system coupled to the motor. Additionally or in the alternative, when the corresponding motor is activated, a torque sensor, if used, can determine the force on the motor during linear or rotary movement of the at least one actuation shaft. The torque sensor can be coupled to the motor to determine or monitor an amount of force being applied to the motor during device operation. It is also contemplated that other ways to determine or monitor force on the motor can include (i) measuring current though the motor by using a sensor or a meter device; or (ii) measuring differences between actual velocity of the motor or components, which may include a combination of a distance travelled and an expired time, and the commanded velocity.

Various embodiments of motors of control systems and various embodiments of tool drivers that house such motors therein are further described in International Patent Publication No. WO 2014/151952 entitled "Compact Robotic Wrist" filed Mar. 13, 2014, International Patent Publication No. WO 2014/151621 entitled "Hyperdexterous Surgical System" filed Mar. 13, 2014, patent application Ser. No.

15/200,283 entitled "Methods, Systems, And Devices For Initializing A Surgical Tool" filed Jul. 1, 2016, and in U.S. patent application Ser. No. 15/237,653 entitled "Methods, Systems, And Devices For Controlling A Motor Of A Robotic Surgical System" filed Aug. 16, 2016, which are hereby incorporated by reference in their entireties.

As mentioned above, one or more motors as well as the control system associated therewith can be disposed within an electrosurgical tool, e.g., with a housing of a proximal housing portion thereof, or can be located outside of the electrosurgical tool, such as part of a surgical robotic system that operatively couples to the electrosurgical tool. As will be appreciated by a person skilled in the art, electronic communication between various components of a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 19:
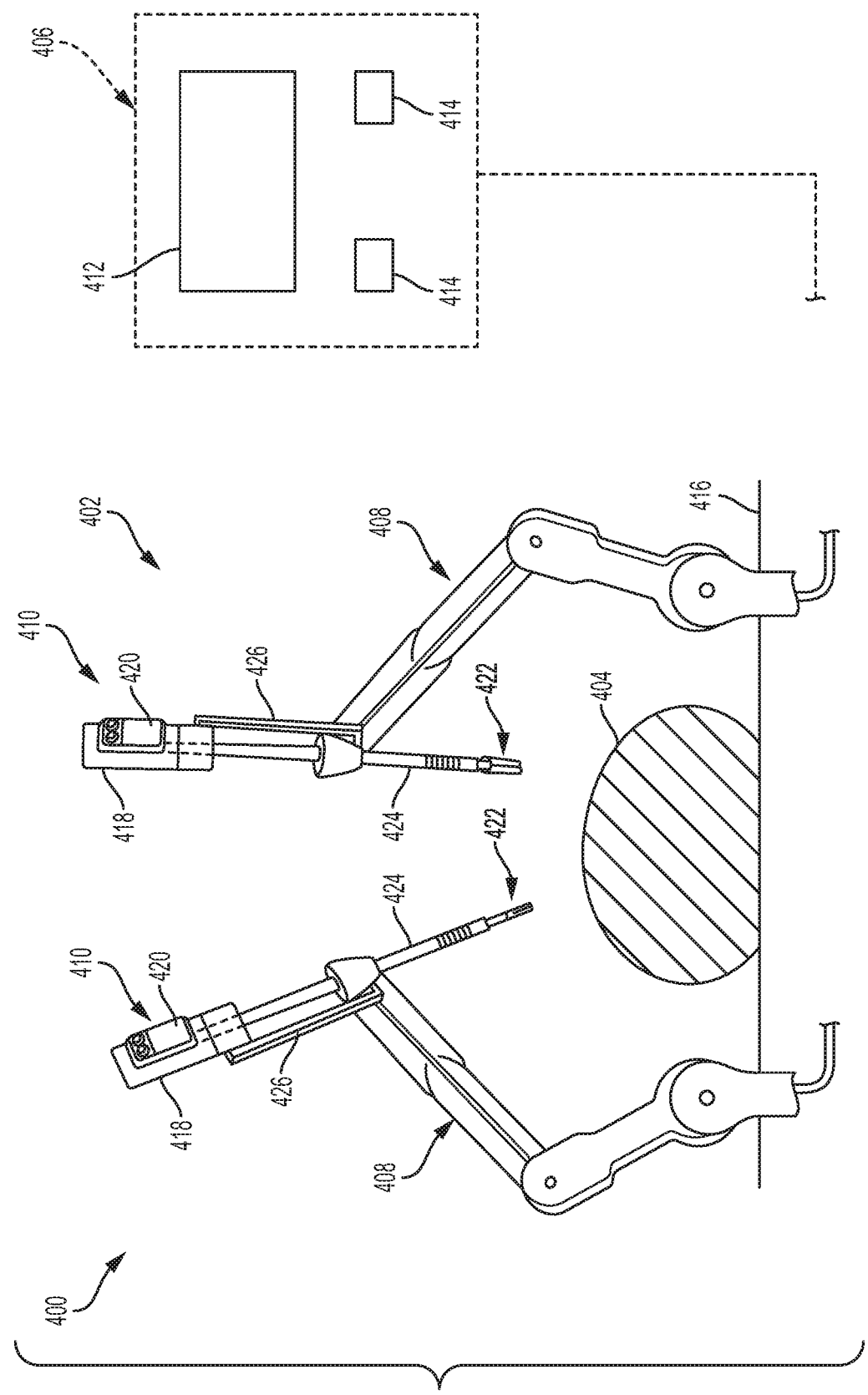
FIG. 19 is a schematic view of one embodiment of a robotic surgical system.

FIG. 19 illustrates one embodiment of a robotic surgical system 400 that includes a patient-side portion 402 that is positioned adjacent to a patient 404, and a user-side portion 406 that is located a distance from the patient, either in the same room and/or in a remote location. The patient-side portion 402 generally includes one or more robotic arms 408 and one or more tool assemblies 410 that are configured to releasably couple to a robotic arm 408. The user-side portion 406 generally includes a vision system 412 for viewing the patient 404 and/or surgical site, and a control system 414 for controlling the movement of the robotic arms 408 and each tool assembly 410 during a surgical procedure.

The control system 414 can have a variety of configurations and can be located adjacent the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 414 can include various components, such as components that enable a user to view a surgical site of the patient 404 being operated on by the patient-side portion 402 and/or to control one or more parts of the patient-side portion 402 (e.g., to perform a surgical procedure at the surgical site). In at least some embodiments, the control system 414 can also include one or more manually-operated input devices, such as a joystick, exoskeletal glove, a powered and gravity-compensated manipulator, or the like. The one or more input devices can control motors which, in turn, control the movement of the surgical system, including the robotic arms 408 and tool assemblies 410.

The patient-side portion 402 can have a variety of configurations. As illustrated in FIG. 19, the patient-side portion 402 can couple to an operating table 416. However, in other embodiments, the patient-side portion 402 can be mounted to a wall, to the ceiling, to the floor, or to other operating room equipment. Further, while the patient-side portion 402 is shown as including two robotic arms 408, more or fewer robotic arms 408 may be included. Furthermore, the patient-side portion 402 can include separate robotic arms 408 mounted in various positions, such as relative to the surgical table 416 (as shown in FIG. 19). Alternatively, the patient-side portion 402 can include a single assembly that includes one or more robotic arms 408 extending therefrom.

One or more motors (not shown) are disposed within a motor housing 418 that is coupled to an end of the arm 408. A tool or drive system housing 420 on a surgical tool can house a drive system (not shown) and can be mounted to the motor housing 418 to thereby operably couple the motor(s) to the drive system, e.g., the housing 110 of the tool 100 can be mounted to the motor housing 418, the housing 332 of the tool 300 can be mounted to the motor housing 41, etc. As a result, when the motors are activated by the control system, the motor(s) can actuate the drive system. As shown in FIG. 19, an end effector 422 including a pair of jaws extends from each tool housing 420. During surgery, the end effector 422 can be placed within and extend through a trocar 424 that is mounted on the bottom of a carrier 426 extending between the motor housing 418 and a trocar support. The carrier 426 allows the tool to be translated into and out of the trocar 424.

Generally, as discussed above, a control system can control movement and actuation of a surgical device such as an electrosurgical tool. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and the processor can be configured for receiving sensed information, aggregating the sensed information, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

In certain embodiments of methods, systems, and devices provided herein, a control system can be configured to control power of a motor that drives translation of a cutting element of an electrosurgical tool to control a speed of the cutting element. Such motor control may allow the cutting element to translate at a speed to efficiently cut tissue of different thicknesses, e.g., translate faster while cutting thinner tissue than while cutting thicker tissue, such motor control may help prevent cutting element and/or end effector breakage to by preventing the cutting element from moving too quickly, such motor control may compensate for cutting element translation when the end effector is at different articulation angles since the more the end effector is articulated the shorter the translation in embodiments in which the cutting element is formed of laminate bands that flex when articulated, and/or such motor control may allow the cutting element to translate slower at a start of a translation stroke than subsequently in the stroke to account for the cutting element possibly not encountering tissue to cut until the cutting element has already translated a distance from its start position due to the tissue's positioning within the electrosurgical tool's end effector. The power of the motor can be controlled based on an impedance of the tissue engaged by the end effector, and/or based on a longitudinal position of the cutting element along the end effector. In an exemplary embodiment, the power of the motor is based on at least two factors, which may provide a more accurate indication of the tissue's thickness and whether the cutting element is translating through tissue (as opposed to, e.g., translating along empty space between tissue-facing surfaces of an end effector's closed jaws). For example, the power of the motor can be controlled based on an impedance of tissue engaged by the end effector and based on a current of the motor, which is a parameter indicative of impedance. For another example, the power of the motor can be controlled based on current of the motor and based on a distance of the cutting element from its start position before beginning translation along the end effector.

In at least some embodiments, the power of the motor can be controlled to be constrained between upper and lower predetermined motor current thresholds, which correspond to upper and lower predetermined cutting element speeds. The cutting element can thus be guaranteed to translate between a certain predetermined minimum speed and a certain predetermined maximum speed, which may help ensure that the cutting element continually moves to cut tissue and/or may help ensure that the motor does not overexert (e.g., run at a power above a safe level).

Figure 20:
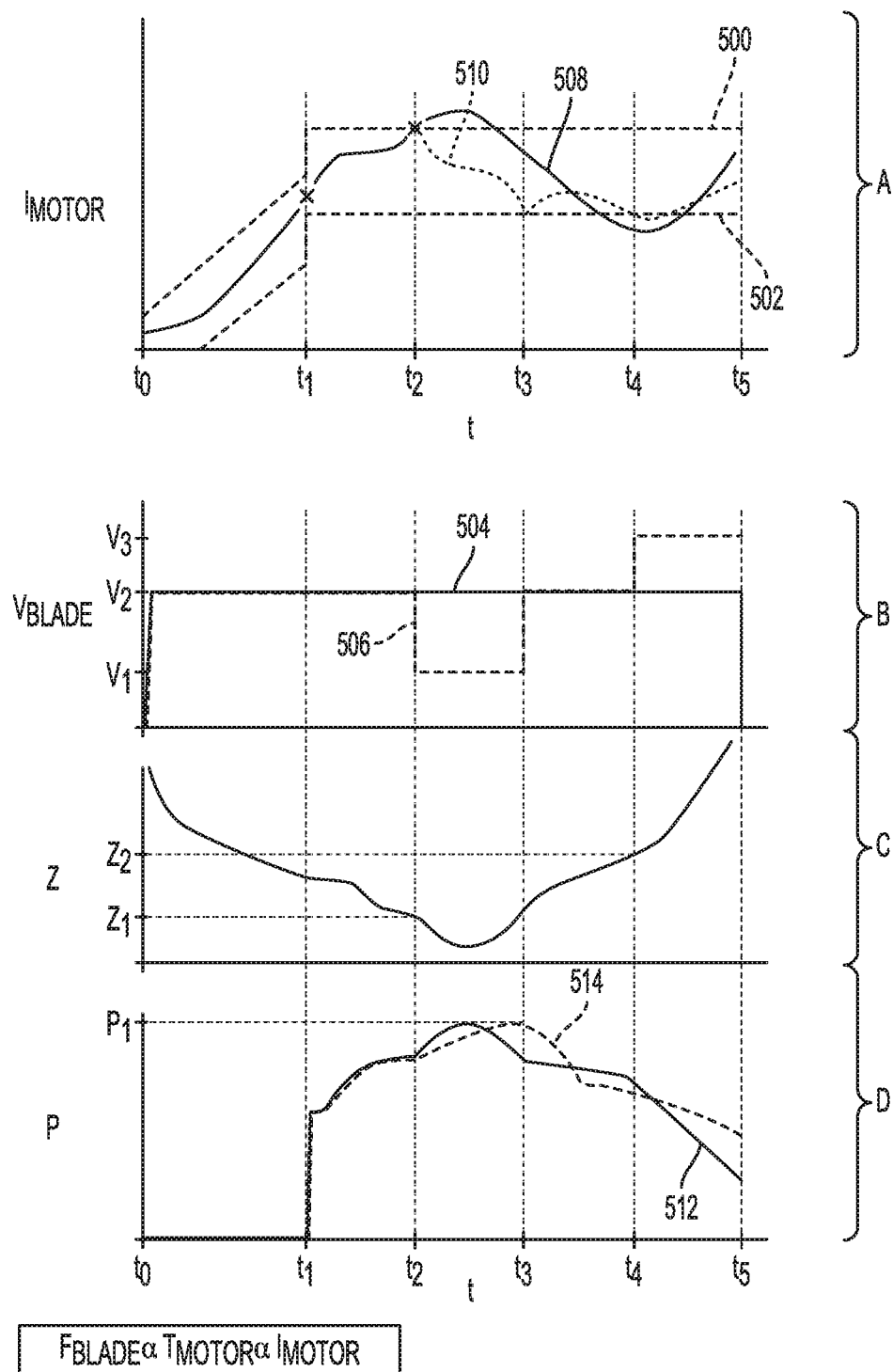
FIG. 20 is a graph illustrating motor current, cutting element velocity, impedance, and power versus time.

FIG. 20 illustrates one embodiment of operation of a control system to control power of a motor that drives translation of a cutting element of an electrosurgical tool to control a speed of the cutting element. The control system is operatively coupled to the electrosurgical tool that includes the cutting element, such as by the electrosurgical tool being removably and replaceably coupled to a tool driver that is operatively coupled to the control system. Section A of FIG. 20 illustrates current I of the motor over time, section B of FIG. 20 illustrates speed v of the cutting element over time, section C of FIG. 20 illustrates impedance Z of tissue over time, and section D of FIG. 20 illustrates power P (or torque τ) of the motor over time. The current I of the motor corresponds to a load or force experienced by the motor, which corresponds to a force of compression exerted by the electrosurgical tool, e.g., force applied to tissue grasped between jaws of the electrosurgical tool.

As shown in section A of FIG. 20, the control system is configured to constrain the current I of the motor between an upper current threshold 500 and a lower current threshold 502. The upper and lower current thresholds 500, 502 are each predetermined, e.g., are preprogrammed as limits into the control system. The upper and lower current thresholds 500, 502 are each variable when no power P is being applied, e.g., between time $t_0$ and time $t_1$, and are each substantially constant when power P is being applied, e.g., after time $t_1$. A person skilled in the art will appreciate that a value may not be precisely constant but nevertheless considered to be substantially constant due to any number of factors, such as manufacturing tolerances and sensitivity of measurement devices. The upper and lower current thresholds 500, 502 being variable when no power P is being applied reflects closure of the electrosurgical tool's end effector on tissue, e.g., load increasing as tissue is clamped while the end effector moves from an open position to a closed position. The upper and lower current thresholds 500, 502 being substantially constant when power P is being applied reflects that the end effector is closed.

In general, the control system is configured to control the current I of the motor and the speed v of the cutting element but is not able to control the impedance Z of the tissue or the power P of the motor. The control system is configured to receive data indicative of the impedance Z of the tissue, e.g., via an impedance sensor or a voltage and current sensor from which impedance can be measured, and data indicative of the power of the motor, e.g., via a torque sensor coupled to the motor to determine or monitor an amount of force being applied to the motor during device operation. The control system can control the current I, and hence control the speed v, based on one or both of the impedance Z and the power P.

The speed v rises from zero to a first speed $v_2$ shortly after time $t_0$. Section B of FIG. 20 shows in solid line a baseline speed 504 in which the speed v is substantially constant at the first speed v2 until the cutting element stops moving at time $t_5$, e.g., until the speed v drops to zero shortly before time $t_5$. Section A of FIG. 20 shows in solid line a baseline current 508 that corresponds to the baseline speed 504. The baseline current 508 is not bounded between the upper and lower current thresholds 500, 502. The baseline speed 504 and baseline current 508 are shown for reference. Section A of FIG. 20 shows in dotted line a controlled current 510 that is controlled by the control system based on the impedance Z and the power P and that is bounded between the upper and lower current thresholds 500, 502. Section B of FIG. 20 shows in dotted line a varying speed 506 in which the speed v varies over time due to the current I control. Section D of FIG. 20 shows in solid line a baseline power 512 for reference and in dotted line a power 514 that results from the control system's control of the current I and speed v.

During a first stage of operation between time $t_0$ and time $t_1$, no power P is being applied, the current I increases, and the impedance Z decreases. Also in the first stage of operation the speed v rises from zero to the first speed $v_2$ shortly after time $t_0$, as mentioned above, and then remains substantially constant at the first speed $v_2$. At time $t_1$, the end effector has been closed, and power P begins being applied. During a second stage of operation between time $t_1$ and time $t_2$, the current I continues to increase but remains below the upper current threshold 500, the speed v is substantially constant at the first speed $v_2$, and the impedance Z continues to decrease but remains above a predetermined lower threshold $Z_1$ of impedance.

At time $t_2$, the impedance Z falls to the lower threshold $Z_1$ of impedance. The impedance Z being at the lower threshold $Z_1$ of impedance is indicative of the current I being at the upper threshold 500. In response to the impedance Z being at the lower threshold $Z_1$ of impedance, the control system causes the current I to decrease, as shown by the controlled current 510 starting to decrease at time $t_2$ and decreasing throughout a third stage of operation between time $t_2$ and time $t_3$. The speed v thus decreases from the first speed $v_2$ to a second, lower speed $v_1$ and is substantially constant at the lower speed $v_1$ during the third stage of operation. Without the control system's control, the current I would increase above the upper current threshold 500, as shown by the baseline current 508 between time $t_2$ and time $t_3$, and the speed v would remain substantially constant at the speed $v_2$, as shown by the baseline speed 504 between time $t_2$ and time $t_3$. During the third stage of operation the power P increases, as shown by the dotted line power 514 between time $t_2$ and time $t_3$.

At time $t_3$, the power P reaches a predetermined upper threshold $P_1$. The power P being at the upper threshold $P_1$ of power is indicative of the current I being at the lower threshold 502. In response to the power P being at the upper threshold $P_1$, the control system causes the current I to increase, as shown by the controlled current 510 starting to increase at time $t_3$ and remaining above the lower threshold 502 throughout a fourth stage of operation between time $t_3$ and time $t_4$. The speed v thus increases from the lower speed $v_1$ to the higher speed $v_2$ and is substantially constant at the higher speed $v_2$ during the fourth stage of operation. Without the control system's control, the current I would fall below the lower current threshold 502, as shown by the baseline current 508 between time $t_3$ and time $t_4$, and the speed v would remain substantially constant at the speed $v_2$, as shown by the baseline speed 504 between time $t_3$ and time $t_4$. During the fourth stage of operation the impedance Z increases.

At time $t_4$, the impedance Z reaches a predetermined upper threshold $Z_2$ of impedance while power P is being applied. In response to the impedance Z being at the upper threshold $Z_2$ of impedance while power P is being applied, the control system causes the current I to increase, as shown by the controlled current 510 starting to increase at time $t_4$ and remaining above the lower threshold 502 throughout a fifth stage of operation between time $t_4$ and time $t_5$. The speed v thus increases from its current speed $v_2$ to a higher speed $v_3$ and is substantially constant at the higher speed $v_3$ during the fifth stage of operation. Without the control system's control, the current I would fall below the lower current threshold 502, as shown by the baseline current 508 between time $t_4$ and time $t_5$, and the speed v would remain substantially constant at the speed $v_2$, as shown by the baseline speed 504 between time $t_4$ and time $t_5$. During the fourth stage of operation the impedance Z increases. At time $t_5$, the speed v decreases to zero in response to the motor ceasing to drive the cutting element, e.g., in response to the motor ceasing to run.

In certain embodiments, a control system can be configured to control speed of an electrosurgical tool's cutting element, e.g., by controlling motor output, based on an angle at which an end effector of the electrosurgical tool is articulated relative to an elongate shaft of the electrosurgical tool. The control system can be configured to control the speed of the cutting element based on articulation angle alone or in addition to one or more additional factors, e.g., tissue impedance, longitudinal position of the cutting element along the end effector, etc.

Figure 21:
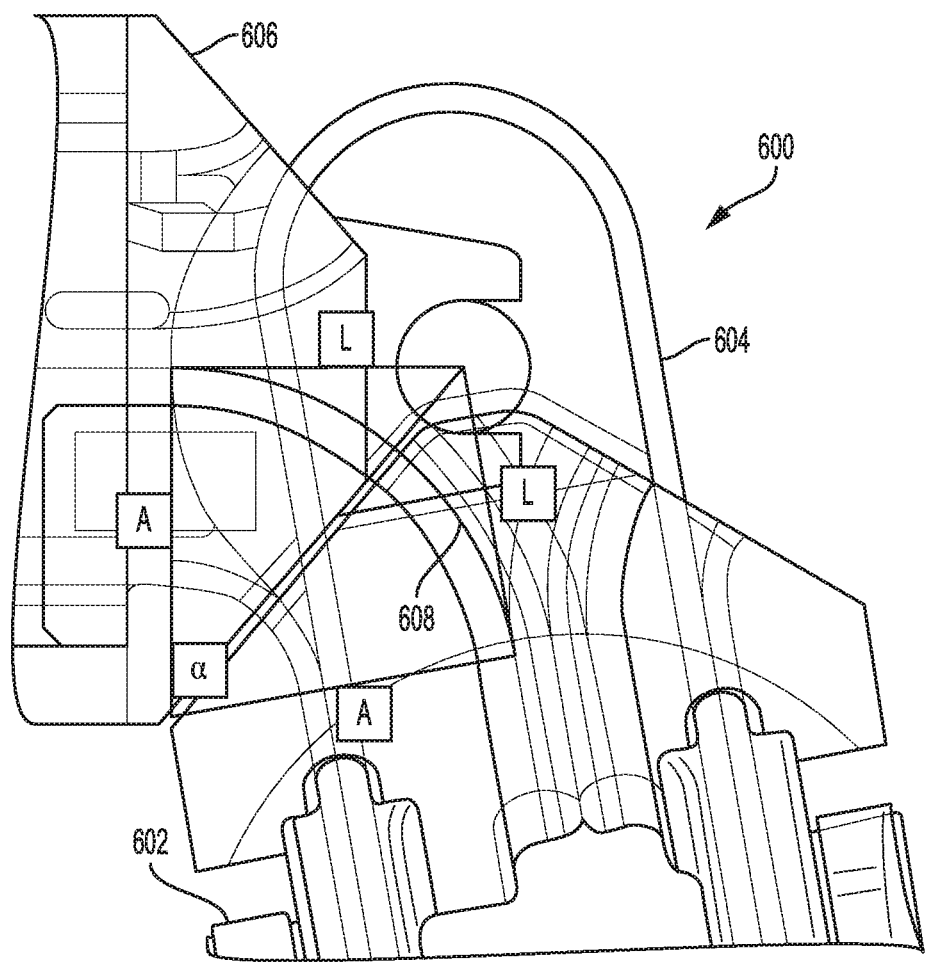
FIG. 21 is a side transparent view of an intermediate portion of another embodiment of an electrosurgical tool.

One embodiment of a control system configured to control speed of an electrosurgical tool's cutting element based on an angle at which an end effector of the electrosurgical tool is articulated relative to an elongate shaft of the electrosurgical tool is described with respect to an electrosurgical tool 600 illustrated in FIG. 21. Although the control is discussed with respect to the tool 600 of FIG. 21, control can be similarly achieved with other electrosurgical tools.

Figure 12:
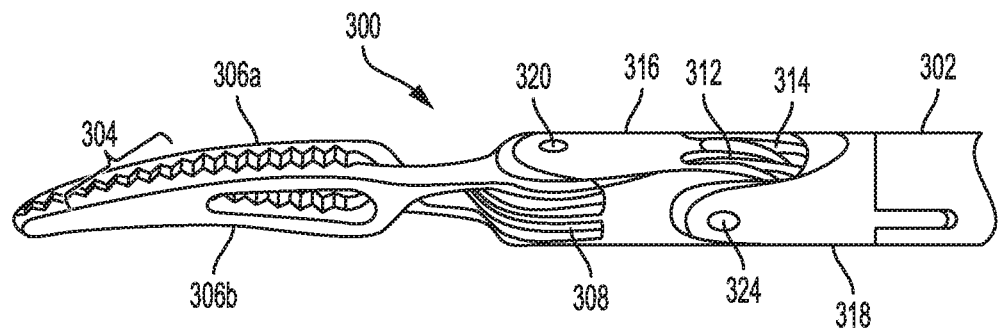
FIG. 12 is a perspective view of a distal portion of another embodiment of an electrosurgical tool.
Figure 13:
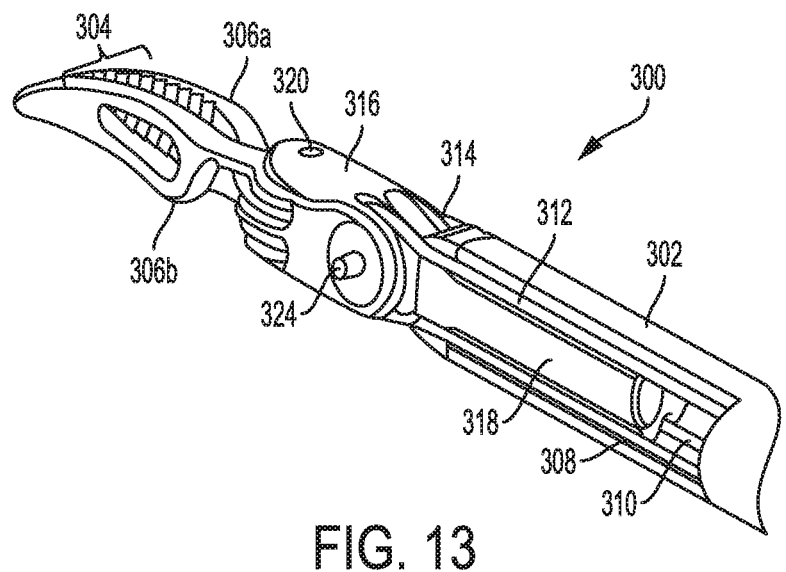
FIG. 13 is another perspective view of a distal portion of the tool of FIG. 12.
Figure 14:
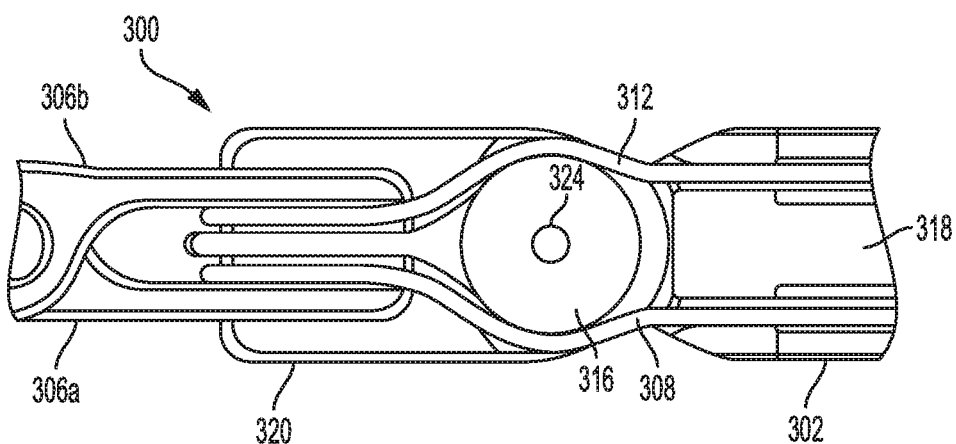
FIG. 14 is a side view of an intermediate portion of the tool of FIG. 12.

The tool 600 is generally configured and used similar to other electrosurgical tools described herein, e.g., the tool 100 of FIG. 1, the tool 200 of FIG. 8, and the tool 300 of FIG. 12. The tool 600 includes a proximal clevis 602, a distal clevis 604 pivotally attached to the proximal clevis 602, and an end effector 606 pivotally attached to the distal clevis 604. The tool 600 includes a plurality of cables (not shown) configured to facilitate end effector opening, end effector closing, and end effector articulation, as discussed herein. FIG. 21 shows a cable path 608 for one of the cables around the pivotal connection between the distal clevis 604 and the end effector 606. The cable path 608 is a circular arc. A length of the cable along the cable path 608 is provided by the following equation, where α is pitch angle of the end effector 606, β is yaw angle of the end effector 606, and Δ is the distance or displacement of the cutting element from its start position before beginning to translate:

$$\text{Cable Length} = 2L + \Delta = \frac{L\alpha}{\tan\left(\frac{\alpha}{2}\right)} + \frac{L\beta}{\tan\left(\frac{\beta}{2}\right)}$$

When the pitch angle α does not equal zero and the yaw angle β does not equal zero, the motor rotation angle θ (in radians) is provided by the following equation, where C is the motor pinion radius:

$$\theta = \left[\frac{L\alpha}{\tan\left(\frac{\alpha}{2}\right)} + \frac{L\beta}{\tan\left(\frac{\beta}{2}\right)} - 4L\right]\frac{1}{C}$$

The pitch angle α and the yaw angle β are known by the control system, as the control system caused the articulation at those angles. The length L of the cable is also known by the control system, as it is a known value of the cable. Thus, the distance Δ traveled by the cutting element can be determined by the control system. The control system can therefore calculate the distance Δ traveled by the cutting element and control the motor based on the distance Δ. For example, in response to the distance Δ reaching a predetermined minimum distance, the control system can be configured to increase the speed of the cutting element's translation, e.g., by controlling the motor's output. The control system can be configured to repeatedly and sequentially calculate the distance Δ during the cutting element's translation to identify when the distance Δ reaches the predetermined minimum distance. Similarly, a position of the motor, e.g., the motor rotation angle θ, can be determined by the control system using the known values of α, β, L, and C.

An electrosurgical tool can include a stop mechanism configured as a backstop for the tool's cutting element. The cutting element can be configured to abut the stop mechanism when in its start position, which may help ensure that the cutting element is in its start position before beginning to translate. For example, the cutting element may distally translate from its start position to cut tissue and then be proximally retracted back before being distally translated again to cut additional tissue. The cutting element should be retracted back to its start position to help ensure that the cutting element's distal translation is accurately controlled during its next distal translation stroke. Retracting the cutting element proximally until the cutting element abuts the stop mechanism may help ensure that the cutting element is in its start position before being distally translated. For another example, the cutting element can be controlled by a control system to abut the stop mechanism during articulation of the tool's end effector, to help ensure that if the cutting element is actuated with the end effector articulated, the cutting element will begin its translation along the end effector from its start position and thus be more accurately controlled by the control system.

Figure 22:
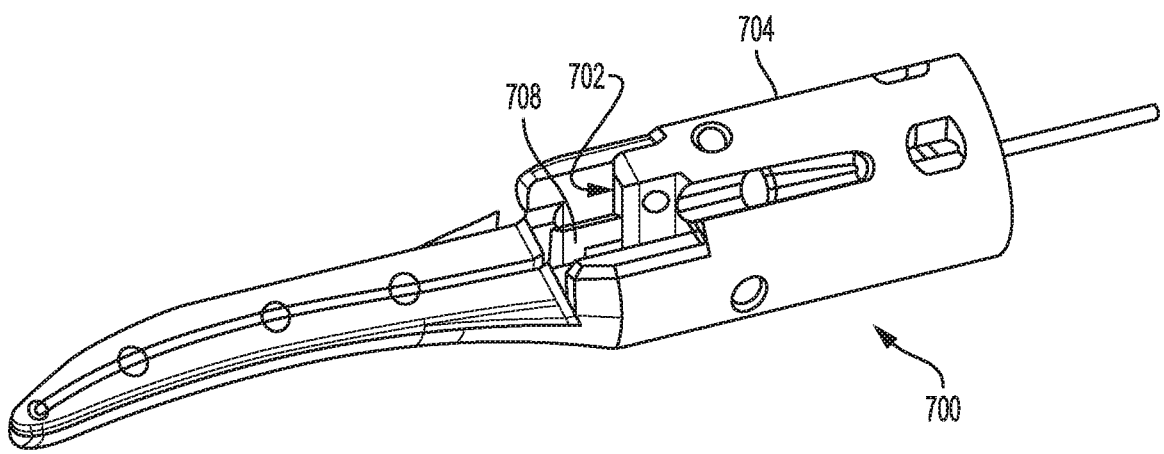
FIG. 22 is a perspective view of a distal portion of another embodiment of an electrosurgical tool.

FIG. 22 illustrates one embodiment of an electrosurgical tool 700 that includes a stop mechanism 702 for a cutting element 708 of the tool 700. In this illustrated embodiment the stop mechanism is a distal-facing surface of a lower jaw 704 of the tool's end effector that is configured to abut a proximal-facing surface of the cutting element 708 when the cutting element 708 is in its start position, as shown in FIG. 22. The tool 700 is generally configured and used similar to other electrosurgical tools described herein, e.g., the tool 100 of FIG. 1, the tool 200 of FIG. 8, and the tool 300 of FIG. 12. A control system operatively coupled to the tool 700 can be configured to cause proximal retraction of the cutting element 708 along the end effector, as discussed herein, until no further proximal movement is possible, thereby indicating that the cutting element 708 has abutted the stop mechanism 702.

Figure 23:
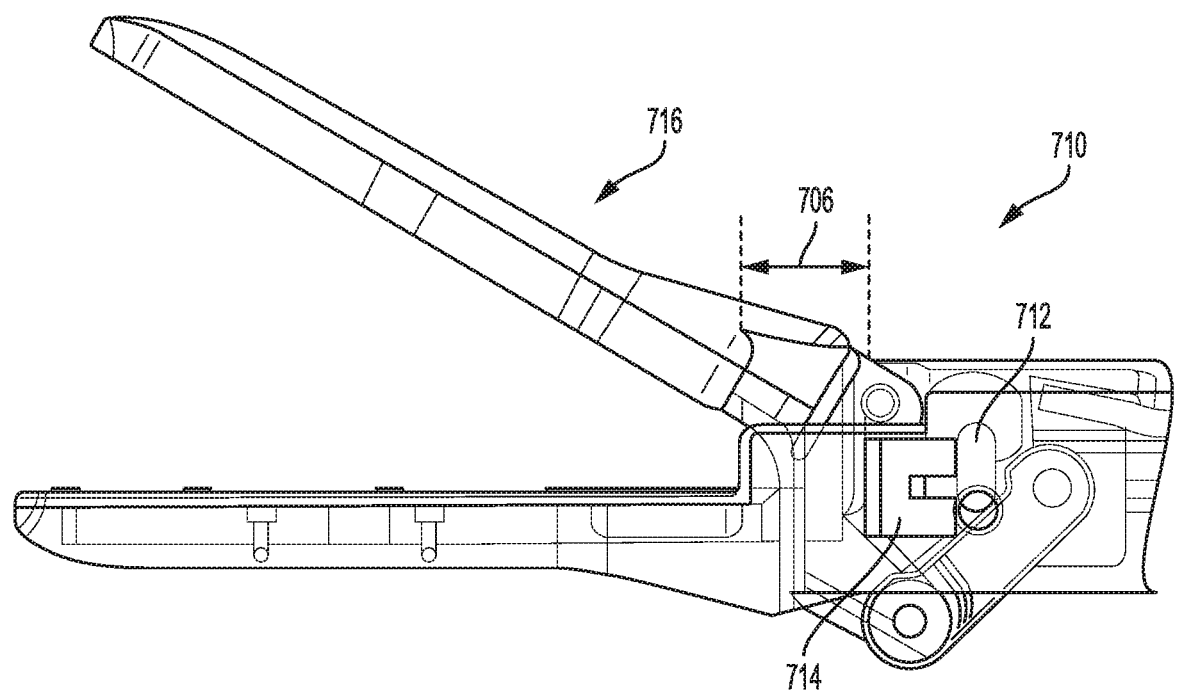
FIG. 23 is a side transparent view of a distal portion of still another embodiment of an electrosurgical tool.

FIG. 23 illustrates another embodiment of an electrosurgical tool 710 that includes a stop mechanism 712 for a cutting element 714 of the tool 710. In this illustrated embodiment the stop mechanism is a rod or bar extending laterally at a proximal end of the tool's end effector 716. The stop mechanism 712, e.g., a distal surface thereof, is configured to abut a proximal-facing surface of the cutting element 714 when the cutting element 714 is in its start position, as shown in FIG. 23. The tool 710 is generally configured and used similar to other electrosurgical tools described herein, e.g., the tool 100 of FIG. 1, the tool 200 of FIG. 8, and the tool 300 of FIG. 12. A control system operatively coupled to the tool 710 can be configured to cause proximal retraction of the cutting element 714 along the end effector 716, as discussed herein, until no further proximal movement is possible, thereby indicating that the cutting element 718 has abutted the stop mechanism 712.

The stop mechanism 702 of FIG. 22 is positioned such that the cutting element 708 in its start position is immediately proximal to tissue-facing surfaces of the end effector's jaws (only the lower jaw 704 is shown, for clarity of illustration of the stop mechanism 702). The cutting element 708 is thus configured to immediately begin cutting tissue grasped by the end effector when the cutting element 708 begins distally translating along the end effector. The stop mechanism 712 of FIG. 23 is positioned a distance 706 proximally beyond a location where the cutting element 714 begins cutting tissue grasped by the end effector 716 when the cutting element 714 begins distally translating along the end effector 716. The distance 706 may help prevent the cutting element 714 from moving into a position where it may accidentally cut tissue during articulation of the end effector 716 and/or may help prevent stroke changes from moving the cutting element 714 a position where it may accidentally cut tissue. In contrast, such distance is substantially zero in the embodiment of FIG. 22. A person skilled in the art will appreciate that a parameter may not be precisely at a value, e.g., the distance may not be precisely zero, but nevertheless considered to be substantially at that value due to any number of factors, such as manufacturing tolerances and sensitivity of measurement devices.

Figure 24:
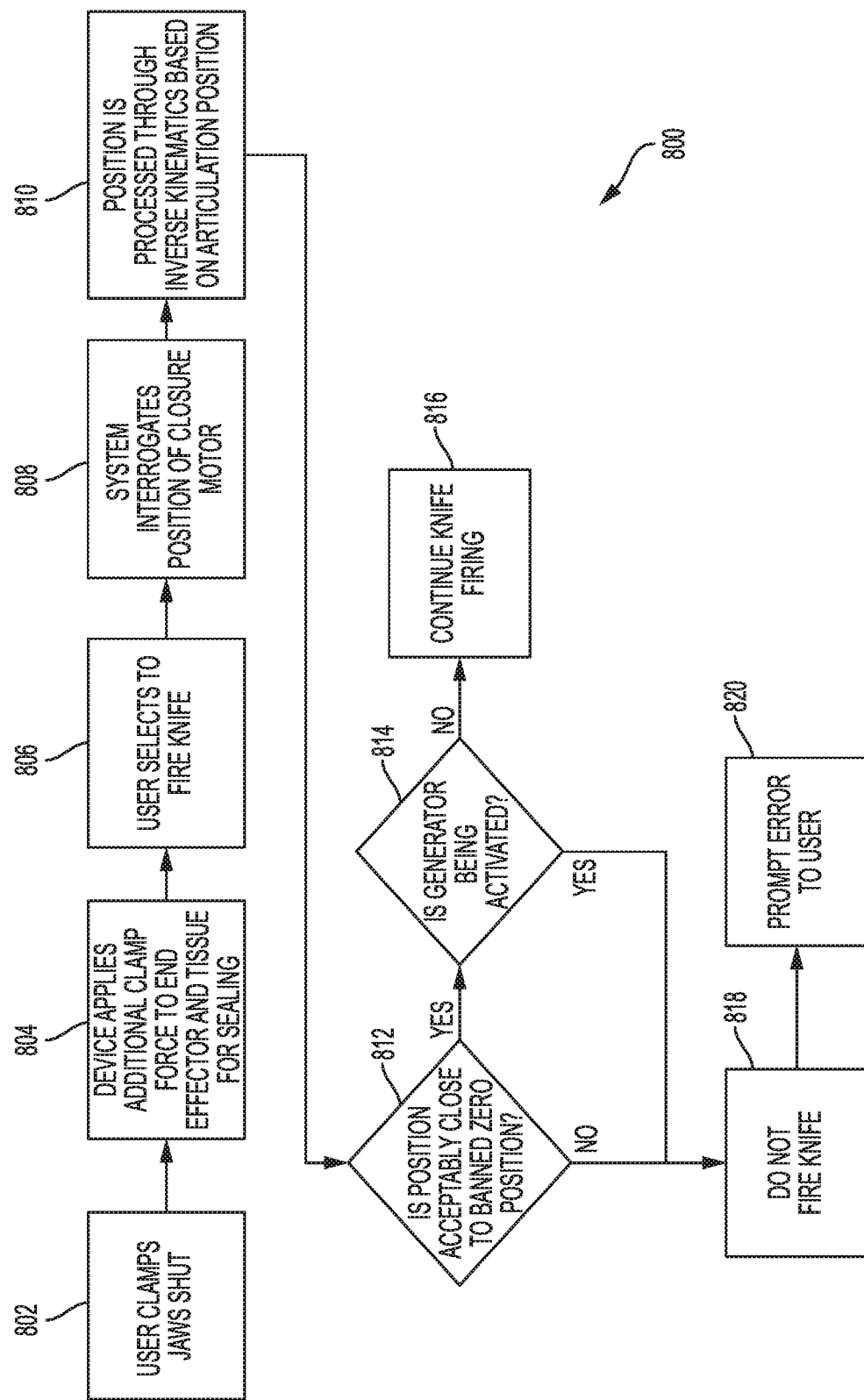
FIG. 24 is a flowchart of one embodiment of a process of controlling speed of an electrosurgical tool's cutting element.

FIG. 24 illustrates one embodiment of a process 800 of controlling speed of an electrosurgical tool's cutting element based on an angle at which an end effector of the electrosurgical tool is articulated relative to an elongate shaft of the electrosurgical and based on the cutting element's distance from its start position. The process 800 is described with respect to the tool 600 of FIG. 21 can be similarly implemented with other electrosurgical tools. In the process 800, the end effector 606 is closed 802, such as by the control system receiving a user input and in response to the user input causing the end effector 606 to move from its open position to its closed position. The tool 600 applies 804 additional clamp force to the end effector 606 and tissue for sealing of the tissue. The control system receives 806 a user input to fire the cutting element. In response to the user input to fire, the control system interrogates 808 a position of the motor that is used for translation of the cutting element, e.g., the motor that is operatively coupled with the drive system for cutting element translation. The interrogation 808 can be, for example, calculation of the motor rotation angle θ using the equation above. In response to the user input to fire, the control system also determines 810 a distance of the cutting element from its start position. For example, the determination 810 can be calculating the distance Δ traveled by the cutting element using the equation above. If the position of the cutting element is determined 812 to be acceptably close to the cutting element's start position, and is a generator operatively coupled to the tool 600 is determined 814 to not be activated (e.g., energy is not currently being applied), then the cutting element is fired 816. Determining 812 whether the cutting element is acceptably close to the cutting element's start position can include determining whether the calculated distance Δ is substantially equal to zero or whether the calculated distance Δ is within a predetermined acceptable tolerance value from zero. If the position of the cutting element is determined 812 to be acceptably close to the cutting element's start position, and is a generator operatively coupled to the tool 600 is determined 814 to be activated (e.g., energy is currently being applied), then the cutting element is not fired 818 and an error notification is provided 820, such as by the control system providing an error message on a display screen, sounding an alarm, etc. If the position of the cutting element is determined 812 to not be acceptably close to the cutting element's start position, then the cutting element is not fired 818 and an error notification is provided 820.

In certain embodiments of methods, systems, and devices provided herein, a control system can be configured to control an electrosurgical tool such that an end effector of the tool compresses tissue engaged by the end effector with different compression forces based on whether or not the electrosurgical tool is applying energy. In an exemplary embodiment, the compressive force is higher during energy application than when energy is not being applied. In other words, when the end effector is grasping tissue, the control system can be configured to cause the end effector to clamp the tissue with a lower force when energy is not being applied than when energy is being applied. Varying the compressive force based on whether energy is being applied or not can allow the end effector to compress tissue more during energy application, which may more effectively seal the tissue than if the tissue was being compressed less during the energy application. For example, heat from RF energy may be more efficiently transferred to tissue clamped at a higher compressive force. For another example, ultrasonic energy may be more efficiently transmitted to tissue clamped at a higher compressive force.

Alternatively or in addition to the control system being configured to control an electrosurgical tool such that an end effector of the tool compresses tissue engaged by the end effector with different compression forces based on whether or not the electrosurgical tool is applying energy, the control system can be configured to compensate for over-closing of the end effector by automatically adjusting a gap between jaws of the end effector to be at a minimum predetermined gap. In other words, the control system can be configured to cause tissue-facing surfaces of the jaws to be a predetermined distance from one another. Adjusting the gap between the jaws may help prevent electrode(s) on the tissue-facing surface of one jaw from contacting electrode(s) on the tissue-facing surface of the other jaw, thereby avoiding a short when energy is being applied using the electrodes on the tissue-facing surface. Adjusting the gap between the jaws allows the electrosurgical tool to not have conductive or non-conductive gap setting features such as protrusions or bumps on facing surfaces of the end effector's jaws, which may simply manufacturing and/or reduce device cost.

Alternatively or in addition to the control system being configured to control an electrosurgical tool such that an end effector of the tool compresses tissue engaged by the end effector with different compression forces based on whether or not the electrosurgical tool is applying energy, and alternatively or in addition to the control system being configured to compensate for over-closing of the end effector by automatically adjusting a gap between jaws of the end effector to be at a minimum predetermined gap, the control system can be configured to control a velocity of end effector closure based on compressive force that the end effector is applying to tissue between the jaws of the end effector and based on a location of the cutting element relative to the end effector. Such control of closure velocity may help prevent over-compression of tissue and/or help prevent electrodes on facing surfaces of the jaws from contacting one another and creating a short.

Figure 25:
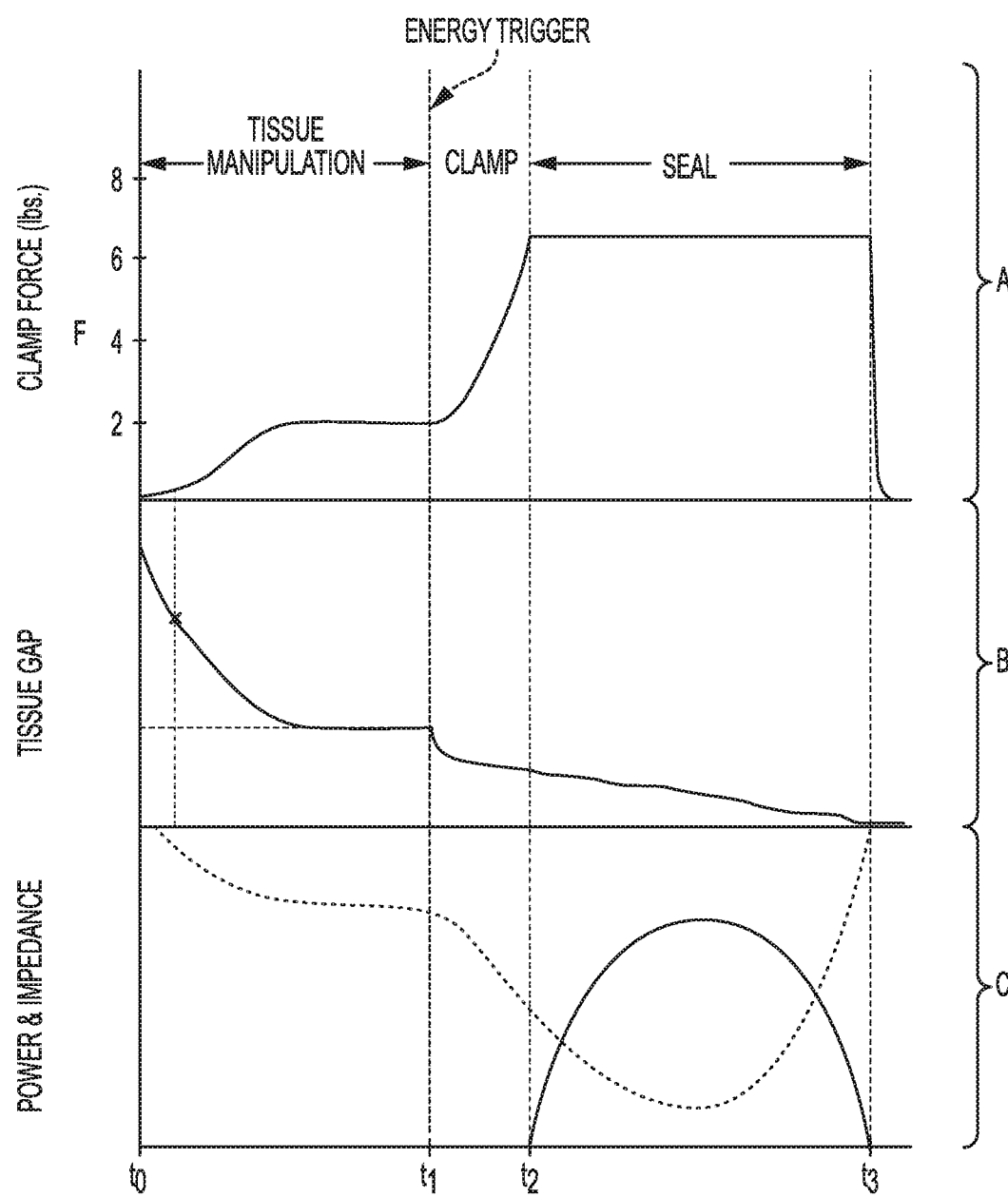
FIG. 25 is a graph illustrating clamp force, tissue gap, power, and impedance over time.

FIG. 25 illustrates one embodiment of operation of a control system configured to control an electrosurgical tool such that an end effector of the tool compresses tissue engaged by the end effector with different compression forces based on whether or not the electrosurgical tool is applying energy. The control system is operatively coupled to the electrosurgical tool, such as by the electrosurgical tool being removably and replaceably coupled to a tool driver that is operatively coupled to the control system. Section A of FIG. 25 illustrates end effector compressive or clamp force F over time, section B of FIG. 25 illustrates a gap $\delta$ between facing surfaces of end effector jaws over time, and section C of FIG. 25 illustrates impedance Z of tissue and motor power over time.

As shown in section A of FIG. 25, during a tissue manipulation stage of operation in which the control system is controlling closure of the end effector, e.g., is causing movement of the jaws from an open position to a closed position, the closure system is configured to prevent from clamp force F from exceeding a first predetermined maximum threshold. The first predetermined maximum threshold is 2.0 lbs. in this illustrated embodiment but can have other values based on, e.g., end effector size, maximum motor power, etc. Section B of FIG. 25 illustrates the closure of the end effector in the tissue manipulation stage of operation, with the gap $\delta$ decreasing over time as the end effector moves closes. Section C of FIG. 25 shows in the tissue manipulation stage of operation as the end effector closes that the impedance Z of the tissue clamped by the end effector is decreasing and that no power is being applied, e.g., no is being delivered to the tissue.

A clamping stage of operation follows the tissue manipulation stage of operation. As shown in section A of FIG. 25, in response to an energy trigger at time $t_1$, e.g., in response to the control system receiving an input that energy is to be applied to tissue, the control system causes the clamping force F to increase to a second predetermined maximum threshold. The first predetermined maximum threshold is 6.5 lbs. in this illustrated embodiment but can have other values based on, e.g., end effector size, maximum motor power, etc.

Section B of FIG. 25 shows that the gap $\delta$ decreases in the clamping stage as the end effector is forced further closed. Section C of FIG. 25 shows that in the clamping stage the impedance Z of the tissue clamped by the end effector is decreasing and that no power is being applied. Thus, following the energy trigger at time $t_1$, period of time, e.g., from time $t_1$ to time $t_2$, passes before energy begins to be applied at time $t_2$.

A sealing stage of operation follows the clamping stage of operation. In response to the clamping force F achieving the second predetermined maximum threshold, the control system causes energy to be applied, e.g., power to begin being delivered. As shown in section A of FIG. 25, the clamping force F is substantially constant during the energy application. As shown in section B of FIG. 25, the gap $\delta$ decreases during the energy application, despite the clamping force F being substantially constant, because the energy applied to the tissue changes the properties of the tissue. As shown in section C of FIG. 25, the impedance Z has an inverse relationship with the power. At time $t_3$ energy stops being applied.

FIG. 26 shows a table of electrosurgical tool functions and whether or not they are possible to be performed in the various stages of operation as illustrated in FIG. 25. In other words, the control system is configured to either prevent or allow certain functions from occurring during different stages of the electrosurgical tool's operation. Cutting element translation is not possible during the tissue manipulation, clamping, and sealing stages or when the energy is triggered, but cutting element translation is possible during a cutting stage of operation. The cutting stage of operation can follow the sealing stage of operation, as in the illustrated embodiment of FIG. 25. End effector articulation and elongate shaft rotation are each possible during the tissue manipulation stage of operation but are not permitted during the clamping, sealing, and cutting stages of operation or when the energy is triggered. Grasping of tissue (e.g., end effector opening/closing) is possible during the tissue manipulation stage of operation and when energy is triggered but is not permitted during the clamping, sealing, and cutting stages of operation. Sealing (energy delivery) is possible during the clamping, sealing, and cutting stages of operation and when the energy is triggered but is not permitted during the tissue manipulation stage of operation.

Figure 27:
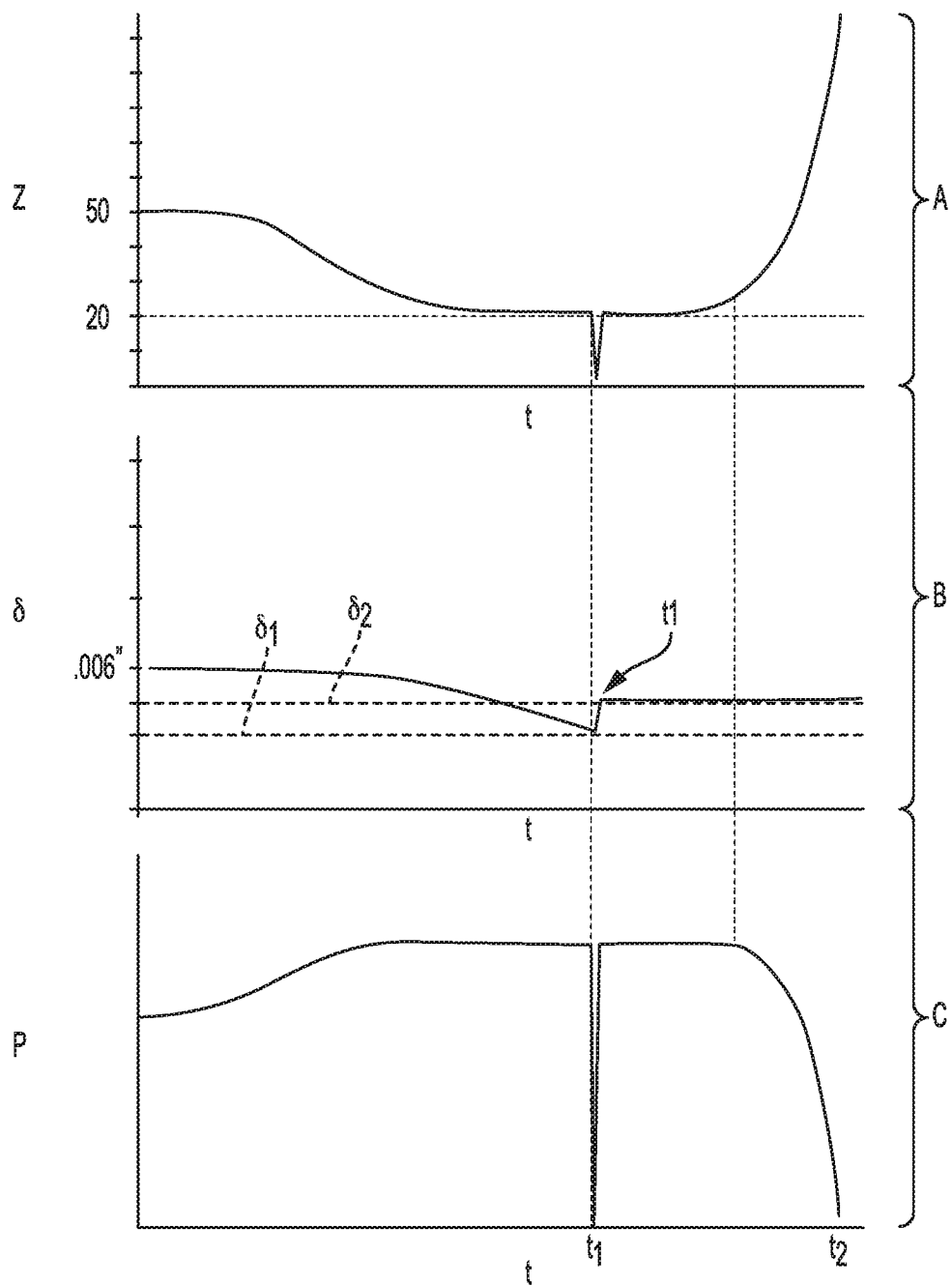
FIG. 27 is a graph illustrating impedance, tissue gap, and power over time.

FIG. 27 illustrates one embodiment of operation of a control system configured to control an electrosurgical tool to compensate for over-closing of the tool's end effector by automatically adjusting a gap between jaws of the end effector to be at a minimum predetermined gap. The control system is operatively coupled to the electrosurgical tool, such as by the electrosurgical tool being removably and replaceably coupled to a tool driver that is operatively coupled to the control system. Section A of FIG. 27 illustrates impedance Z of tissue over time, section B of FIG. 27 illustrates a gap $\delta$ between facing surfaces of end effector jaws over time, and section C of FIG. 27 illustrates motor power over time. The initial tissue gap $\delta$ at time $t_0$ is 0.006" and the initial tissue impedance Z is 50Ω in this illustrated embodiment but each can be other values.

As shown in FIG. 27, when a short (short circuit) occurs, the impedance Z drops to substantially zero, the gap $\delta$ drops to a predetermined minimum gap $\delta_1$, and the power drops to substantially zero. The control system can this be configured to determine when a short occurs by determining whether the impedance Z is substantially zero, the gap $\delta$ equals the predetermined minimum gap 61, and the power is substantially zero. In response to determining that a short has occurred, the control system is configured to cause the end effector to open such that the gap δ increases to a minimum closed loop gap $δ_2$ that is greater than the predetermined minimum gap $δ_1$. FIG. 27 illustrates a short occurring at time $t_1$ and the gap δ immediately thereafter being increased to be the minimum closed loop gap $δ_2$. The impedance Z and power thus normalize back to their pre-short levels, and energy application continues normally until time $t_2$.

In at least some embodiments, the control system can be configured to cause a short to occur. The short will trigger the control system to set the gap δ at the minimum closed loop gap $δ_2$. Thus, causing a short can reset the gap δ to be at a known value, which may allow the control system to wait to trigger the application of energy until the gap δ is reset in order to ensure that a short will not happen upon the start of energy delivery or soon thereafter because the jaws were too close together when energy was triggered.

Figure 28:
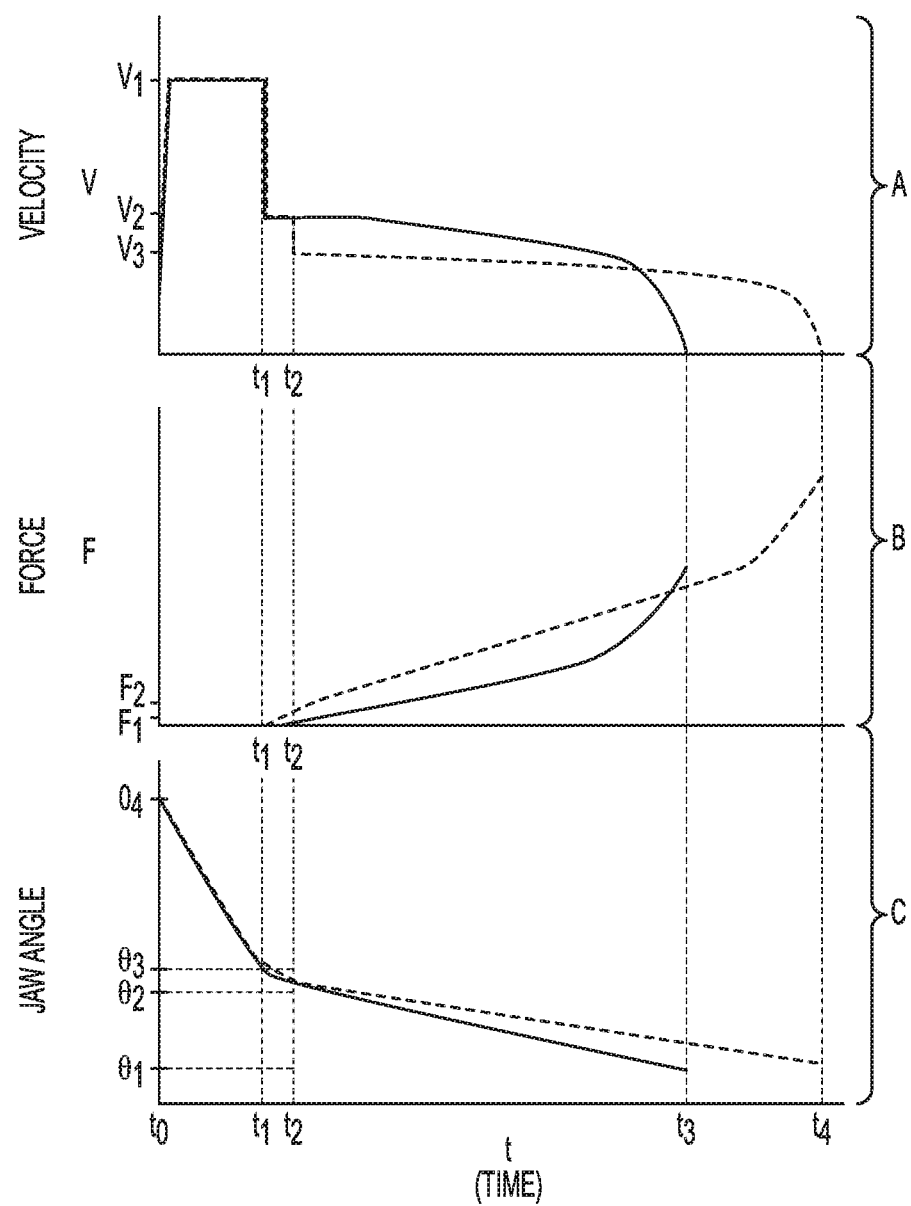
FIG. 28 is a graph illustrating velocity, force, and jaw angle over time.

FIG. 28 illustrates one embodiment of operation of a control system configured to control a velocity of end effector closure based on compressive force that the electrosurgical tool's end effector is applying to tissue between jaws of the end effector and based on a location of a cutting element relative to the end effector. The control system is operatively coupled to the electrosurgical tool, such as by the electrosurgical tool being removably and replaceably coupled to a tool driver that is operatively coupled to the control system. Section A of FIG. 28 illustrates velocity v between facing surfaces of end effector jaws over time (e.g., end effector closure speed over time), section B of FIG. 28 illustrates end effector compressive or clamp force F over time, and section C of FIG. 28 illustrates jaw closure angle θ over time. The solid lines in each of sections A, B, and C corresponds to baseline tissue, and the dotted lines in each of sections A, B, and C corresponds to stiffer tissue with a same geometry as the baseline tissue.

As shown in section A of FIG. 28, in response to an input to close the end effector at time $t_0$, the control system causes the end effector to begin closing at a first predetermined velocity $v_1$. The end effector closes at the first predetermined velocity $v_1$ until the end effector's tissue-facing surfaces contact tissue at time $t_1$. Section B of FIG. 28 reflects the tissue contact at time $t_1$ by the clamping force F being substantially zero until time $t_1$. Section C of FIG. 28 shows that the jaw angle θ decreases as the jaws move closer together between time $t_0$ and time $t_1$.

In response to the clamping force F increasing, the control system can be configured to cause the velocity v to decrease from the first velocity $v_1$ to a second predetermined velocity $v_2$ that is less than the first predetermined velocity $v_1$. In other words, the force F increasing from substantially zero indicates that the end effector has begun to clamp tissue such that the closure can slow down to, e.g., help avoid motor overexertion and/or help avoid overly traumatizing the tissue. Section C of FIG. 28 shows that the jaw angle θ decreases as the jaws move closer together between time $t_1$ and time $t_2$. Section C of FIG. 28 shows that the jaw angle θ decreases as the jaws move closer together between time $t_1$ and time $t_2$.

In response to the force F increasing to a predetermined threshold force $F_2$, which occurs at time $t_2$, the control system is configured to cause the velocity v to drop from the second predetermined velocity $v_2$. The velocity v can thus continue to decrease as the compressive force F increases between time $t_2$ and time $t_3$, at which time closure is complete for baseline tissue, or time $t_4$, at which time closure is complete for stiffer tissue. Section C of FIG. 28 shows that the jaw angle θ decreases as the jaws move closer together between time $t_2$ and time $t_3$ or $t_4$.

In certain embodiments of methods, systems, and devices provided herein, a control system can be configured to detect if a short (short circuit) has occurred between electrodes of an electrosurgical too. The control system can also be configured to allow energy to be delivered to the electrodes is no short is detected and configured to prevent energy from being delivered to the electrodes if a short is detected. The control system may thus improve safety by preventing the electrodes from being energized when there is no tissue contacting the electrodes, such as if the electrosurgical tool's end effector has closed but is unintentionally not grasping tissue, if previously grasped tissue was not grasped securely and has slipped out of the end effector, or if energy was unintentionally triggered for delivery when the end effector has not grasped any tissue. Conventional generators are unable through the monitoring of various parameters to tell the difference between an end effector of an electrosurgical tool engaging thin tissue, in which case energy can be safely delivered, and the electrosurgical tool experiencing a short, in which case energy should not be delivered in order to prevent damage to the tool and/or non-tissue matter engaged by the end effector. The control system being configured to determine whether or not a short has occurred may allow energy to be delivered to thin tissue from the generator when otherwise the generator would not allow energy to be delivered to the thin tissue due to the generator's inability to recognize that tissue is in fact engaged.

The control system can be configured to detect a short in a variety of ways. In an exemplary embodiment, the control system is configured to monitor an electrical parameter during end effector closure, e.g., as jaws of the end effector move from an open position to a closed position. In response to the electrical parameter dropping to a predetermined minimum parameter threshold, the control system can be configured to cause the end effector to open. The control system is also configured to monitor a gap between jaws of the end effector and only cause the end effector's jaws to open when the electrical parameter has dropped to the predetermined minimum parameter threshold (e.g., is equal to or below the predetermined minimum parameter threshold) and the gap has dropped to a predetermined minimum distance threshold (e.g., is equal to or below the predetermined minimum distance threshold). The control system may thus not prematurely cause opening of the end effector in response to the electrical parameter dropping to the predetermined minimum parameter threshold prior to the jaws being closed. The control system is configured to continue monitoring the electrical parameter during the end effector's opening and, based on the electrical parameter's value during the opening, determine if a short occurred or if tissue was clamped between the jaws in the closed position. In an exemplary embodiment, the electrical parameter is impedance, but other electrical parameters can be used, such as resistance, current, and power. Thinner tissue has lower impedance than thicker tissue such that a low impedance can incorrectly indicate to a generator that tissue is not engaged by an electrosurgical tool when in fact thin tissue is engaged by the tool. Monitored impedance staying substantially constant during the end effector opening is indicative of a short, and monitored impedance spiking upward, and remaining spiked, is also indicative of a short. Monitored impedance gradually increasing during the end effector opening is indicative of the end effector engaging tissue and that a short has not occurred.

Figure 29:
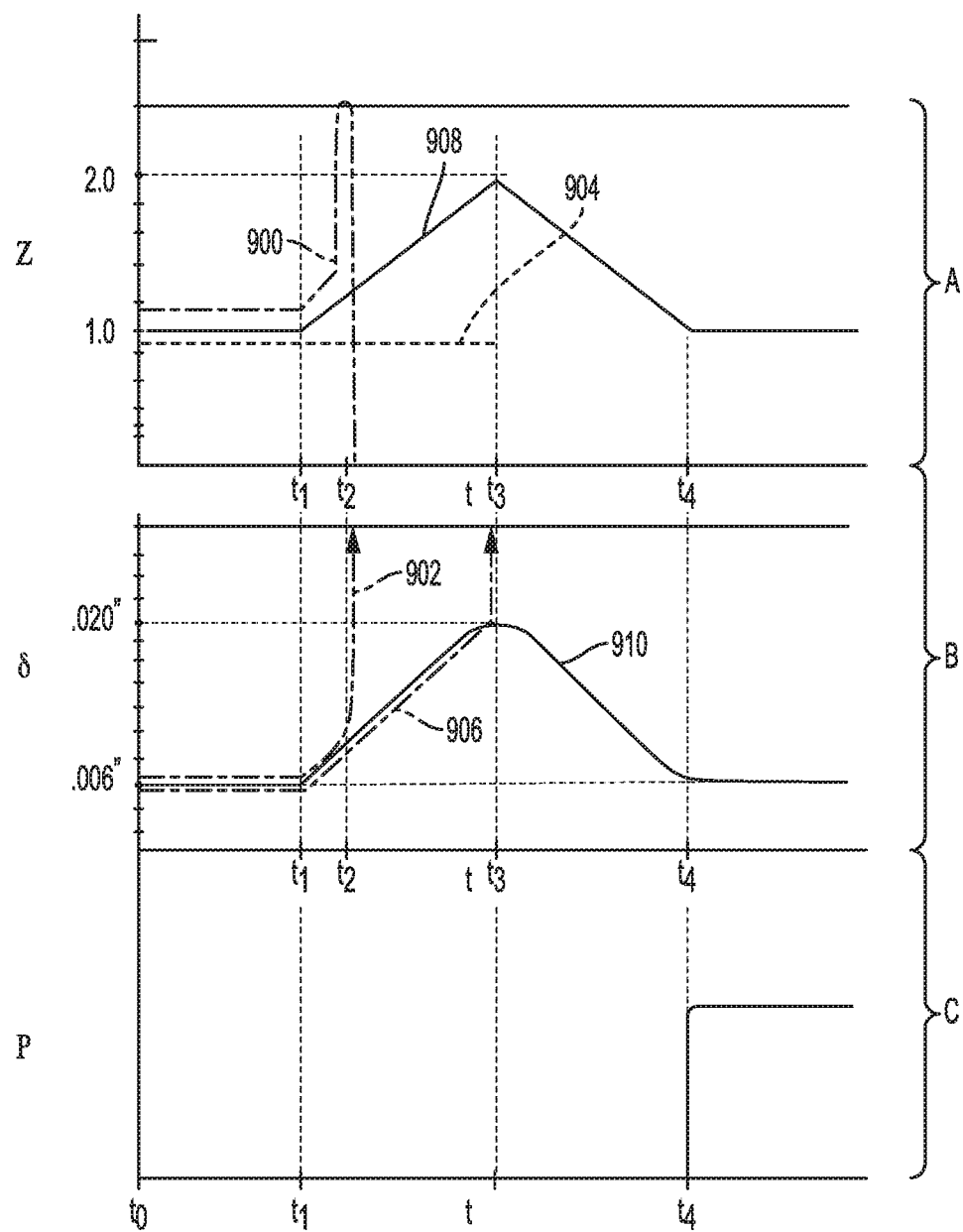
FIG. 29 is another graph illustrating impedance, tissue gap, and power over time.

FIG. 29 illustrates one embodiment of operation of a control system configured to monitor an electrical parameter during end effector closure to facilitate detection of a short. The control system is operatively coupled to the electrosurgical tool that includes the end effector, such as by the electrosurgical tool being removably and replaceably coupled to a tool driver that is operatively coupled to the control system. Section A of FIG. 29 illustrates impedance Z (in Ohms) of tissue over time, Section B of FIG. 29 illustrates a gap δ between facing surfaces of jaws of an end effector over time, and Section C of FIG. 29 illustrates generator power P over time. FIG. 29 illustrates an embodiment in which the electrical parameter monitoring by the control system to facilitate short detection is impedance, but as mentioned above, other electrical parameters may be used.

End effector closure begins at a time prior to time $t_0$ in FIG. 29. The control system is configured to start monitoring impedance, such as by gathering impedance data via one or more impedance sensors, in response to the start of end effector closure, e.g., in response to the control system receiving an input requesting end effector closure. The control system is also configured to start monitoring a gap between the end effector's jaws, such as by gathering position data via one or more position sensors, in response to the start of end effector closure, e.g., in response to the control system receiving an input requesting end effector closure. In response to the impedance being at or below a predetermined minimum impedance threshold for a predetermined amount of time and the gap being at or below a predetermined minimum distance threshold for the predetermined amount of time, the control system is configured to cause the end effector to open. The control system does not receive an outside input, e.g., an input instruction from a user, to open the end effector. Instead, the control system is configured to automatically cause the end effector opening as part of a short detection scheme. The predetermined minimum impedance threshold in this illustrated embodiment is about 1.1Ω, and the predetermined minimum distance threshold in this illustrated embodiment is about 0.0065", although other predetermined minimum impedance thresholds and predetermined minimum distance thresholds can be used. The predetermined amount of time in this illustrated embodiment is defined by the time between time $t_0$ and time $t_1$.

As shown in Section A of FIG. 29, the control system causes the end effector to open at time $t_1$, as indicated by the gap δ beginning to increase at time $t_1$. Sections A and B of FIG. 29 illustrate three scenarios that can result when the end effector opens. A first scenario is the impedance spiking during the end effector opening, as indicated by a first impedance line 900, which indicates a short condition. In response to the control system detecting that the impedance spikes above a predetermined impedance threshold prior to the gap δ reaching a predetermined gap threshold and/or detecting that the impedance spikes before a predetermined amount of time has elapsed after end effector opening (e.g., the predetermined amount of time being the time between time $t_1$ and time $t_2$), the control system causes the end effector to fully open since a short has been detected. The predetermined impedance threshold is about 2.0Ω in this illustrated embodiment but can be other values. The predetermined gap threshold is about 0.020" in this illustrated embodiment but can be other values. The end effector opening in the first scenario is indicated by a first gap line 902.

A second scenario is the impedance remaining substantially constant during the end effector opening, as indicated by a second impedance line 904, which indicates a short condition. In response to the control system detecting that the impedance remains substantially constant until the gap δ increases to a predetermined gap threshold and/or detecting that the impedance remains substantially constant for a predetermined amount of time after end effector opening begins (e.g., the predetermined amount of time being the time between time $t_1$ and time $t_3$), the control system causes the end effector to fully open since a short has been detected. The predetermined gap threshold is about 0.020" in this illustrated embodiment but can be other values. The end effector opening in the second scenario is indicated by a second gap line 906.

In response to detecting the short under either the first scenario or the second scenario, the control system prevents energy from being applied. The control system can also be configured to provide a notification of the detected short, such as by providing an audible sound, providing a message on a display, etc., so a user can, for example, take corrective action, such as repositioning the electrosurgical tool to attempt again to grasp tissue.

A third scenario is the impedance gradually increasing during the end effector opening, as indicated by a third impedance line 908, which indicates that the end effector is grasping tissue. In response to the control system detecting that the impedance is gradually increasing until the gap δ increases to a predetermined gap threshold and/or detecting that the impedance gradually increases for a predetermined amount of time after end effector opening begins (e.g., the predetermined amount of time being the time between time $t_1$ and time $t_3$, which is the same predetermined amount of time used in the second scenario), the control system causes the end effector to begin closing again since a short has not been detected. The predetermined gap threshold is about 0.020" in this illustrated embodiment, same as the predetermined gap threshold used in the second scenario, but can be other values. The end effector closing in the third scenario is indicated by a third gap line 910. When the end effector has returned to the closed position, at time $t_4$ in FIG. 29, the control system is configured to cause energy to be delivered to the tissue via the electrosurgical tool. The energy delivery is indicated by the power P beginning at time $t_4$.

In certain embodiments of methods, systems, and devices provided herein, a control system can be configured to control an end effector's compression force on tissue based on a type of energy being delivered to the tissue via the end effector. In other words, the control system can be configured to vary end effector pressure based on energy modality. In an exemplary embodiment, the control system can be configured to adjust the compression force based on whether only RF energy is being delivered to the tissue, only ultrasonic energy is being delivered to the tissue, or both RF energy and ultrasonic energy is being delivered to the tissue. Varying the pressure applied to tissue by the end effector during energy delivery may facilitate efficient coagulation of tissue, which is accomplished with RF energy, and efficient cutting of tissue, which is accomplished with ultrasonic energy. When both RF energy and ultrasonic energy are being simultaneously applied to tissue, the ultrasonic energy is being used to reinforce coagulation of tissue being causes by the RF energy. However, ultrasonic energy tends to cause tissue cutting. By reducing an amount of end effector pressure when both RF energy and ultrasonic energy are being applied to tissue, coagulation can occur without the tissue being cut, thereby allowing for tissue sealing prior to the tissue being cut, e.g., before ultrasonic energy is applied without RF energy simultaneously being applied, which may facilitate tissue healing and/or reduce bleeding.

In an exemplary embodiment, the control system is configured to monitor an overall intensity of energy being delivered to the tissue during application of energy to the tissue to determine an amount of compression force that should be applied to the tissue. Impedance of the tissue is indicative of overall intensity of energy being delivered to the tissue. Thus, the control system is configured to monitor impedance of the tissue grasped by the end effector during the application of energy to the tissue, such as by gathering impedance data via one or more impedance sensors. Based on the monitored impedance and based on the type of energy being applied, the control system is configured to vary the end effector compression force.

Figure 30:
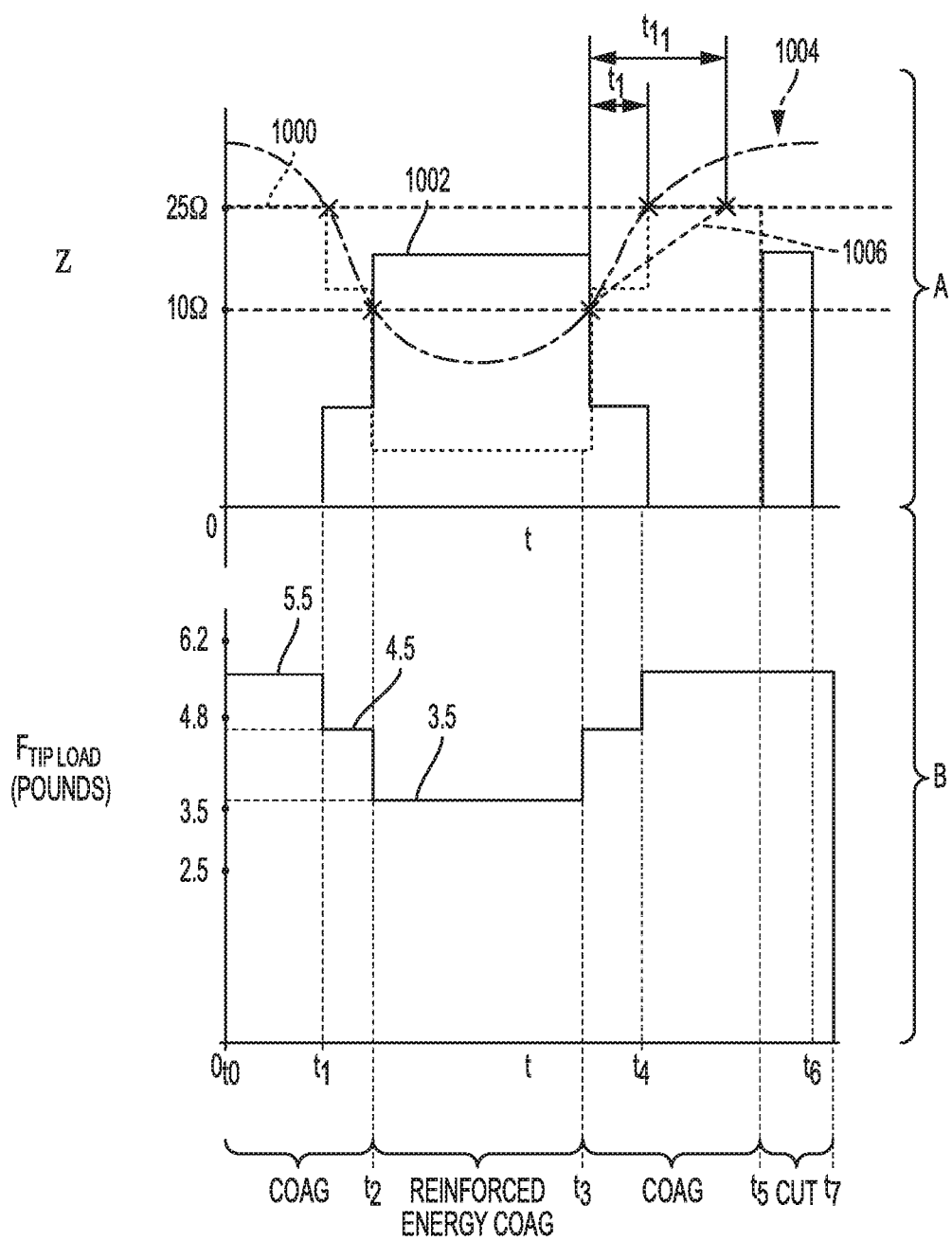
FIG. 30 is a graph illustrating impedance and force over time.

FIG. 30 illustrates one embodiment of operation of a control system configured to control an end effector's compression force on tissue based on a type of energy being delivered to the tissue via the end effector. The control system is operatively coupled to the electrosurgical tool that includes the end effector, such as by the electrosurgical tool being removably and replaceably coupled to a tool driver that is operatively coupled to the control system. Section A of FIG. 30 illustrates impedance Z (in Ohms) of tissue over time, and Section B of FIG. 30 illustrates end effector compression force (tip load) $F_{tip\ load}$ (in pounds) over time.

During a first stage of operation between time $t_0$ and time $t_2$, tissue coagulation occurs due to energy application to the tissue. As shown in FIG. 30, energy application to tissue begins at time $t_0$. The energy application begins with only RF energy being delivered, as reflected by an RF line 1000 in Section A of FIG. 30, which is shown as a dotted line. While only the RF energy is being delivered, in this illustrated embodiment, the tissue impedance is about 25Ω and the end effector compression force is about 5.5 pounds. RF energy is the only type of energy being applied to the tissue until time $t_1$, when ultrasonic energy begins being applied simultaneously with RF energy. The control system is configured to begin the ultrasonic energy automatically as part of achieving tissue coagulation. An ultrasonic line 1002 in Section A of FIG. 30, which is shown as a solid line, reflects the impedance of the tissue causes by the ultrasonic energy. Overall impedance is shown by an overall impedance line 1004. In some instances, overall impedance may be less than expected after time $t_3$, as shown by impedance line 1006, but the control system operates the same way. The tissue impedance drops at time $t_1$ due to two types of energy being applied to the tissue. In this illustrated embodiment, the tissue impedance drops from about 25Ω (time $t_0$ to time $t_1$) to about 17Ω (time $t_1$ to time $t_2$), which is the sum of the impedance (about 12Ω) due to RF energy and the impedance (about 5Ω) due to ultrasonic energy. In response to detecting the impedance drop and two modes of energy being applied, the control system causes the end effector compression force to decrease, in this illustrated embodiment from about 5.5 pounds to about 4.5 pounds.

At time $t_2$, the impedance decreases while two modes of energy are being applied to the tissue. As shown by the RF and ultrasonic lines 1000, 1002, the overall impedance decreases at time $t_2$ to about 10Ω. Enough RF energy cannot be delivered if impedance is under about 10Ω. This overall impedance is less than the overall impedance when only RF energy is being applied (between time $t_0$ and time $t_1$). The increase in ultrasonic energy and decrease in RF energy in this second stage of operation (between time $t_2$ to time $t_3$) is configured to be caused automatically by the control system as part of enhancing the tissue coagulation achieved in the first stage of operation. In response to the impedance decreasing and two modes of energy being applied to the tissue, the control system causes the end effector compression force to decrease, in this illustrated embodiment from about 4.5 pounds to about 3.5 pounds.

At time $t_3$, the balance of RF energy and ultrasonic energy returns to the same levels as between times $t_1$ and $t_2$. Thus, in this third stage of operation (between time $t_3$ and time $t_5$), coagulation occurs. As shown by the RF and ultrasonic lines 1000, 1002, the overall impedance begins to increase at time $t_3$. In response to detecting the impedance increase and two modes of energy being applied, the control system causes the end effector compression force to increase, in this illustrated embodiment from about 3.5 pounds to about 4.5 pounds. At time $t_4$, the overall impedance increases again in response to ultrasonic energy being stopped and only RF energy being applied, similar to the RF energy application between time $t_0$ and time $t_1$. In response to detecting the impedance increase and only one mode of energy being applied, the control system causes the end effector compression force to increase, in this illustrated embodiment from about 4.5 pounds to about 5.5 pounds.

At time $t_5$ a fourth stage of operation (time $t_5$ to time $t_7$) begins in which ultrasonic energy but not RF energy is applied such that the tissue is cut. Although overall impedance decrease at time $t_5$ in response to only ultrasonic energy being applied, the control system maintains the end effector compression force since only ultrasonic energy is being applied instead of only RF energy or both RF energy and ultrasonic energy.

In certain embodiments of methods, systems, and devices provided herein, a control system can be configured to monitor one or more parameters of an electrosurgical tool operatively coupled thereto, e.g., via a tool driver. The control system can be configured to monitor the parameter(s) while operatively coupled to a generator, also referred to herein as an ESU (electrosurgical unit). The control system can be configured to manipulate the monitored parameter data and to transmit the manipulated parameter data to the generator. The generator can thus make decisions based on the manipulated parameter data rather than on the unmanipulated data. In this way, the generator can be spoofed or fooled by the control system into making decisions that would not result if the generator made decisions based on the unmanipulated parameter data, e.g., because it would result in the generator operating outside of its predetermined normal operating conditions. In other words, the control system can be configured to force the generator to operate outside its predetermined normal operating conditions by feeding it manipulated data that is different than the unmanipulated data. For example, the control system can transmit manipulated tissue impedance data to the generator to cause the generator to deliver energy that it would not deliver based on the unmanipulated impedance data because it would violate the generator's predetermined normal operating conditions. Some generators, particularly older generators, lack the processing capability to consider certain parameters in determining energy to deliver and/or have predetermined normal operating conditions that outdate operating capabilities of more modern electrosurgical tools and control systems. Allowing the control system to override generators by providing manipulated data to the generators may allow these older generators to be used with more modern electrosurgical tools and control systems since the control system knows the capabilities of the generator, e.g., by being preprogrammed with the generator's operating capabilities.

Figure 31:
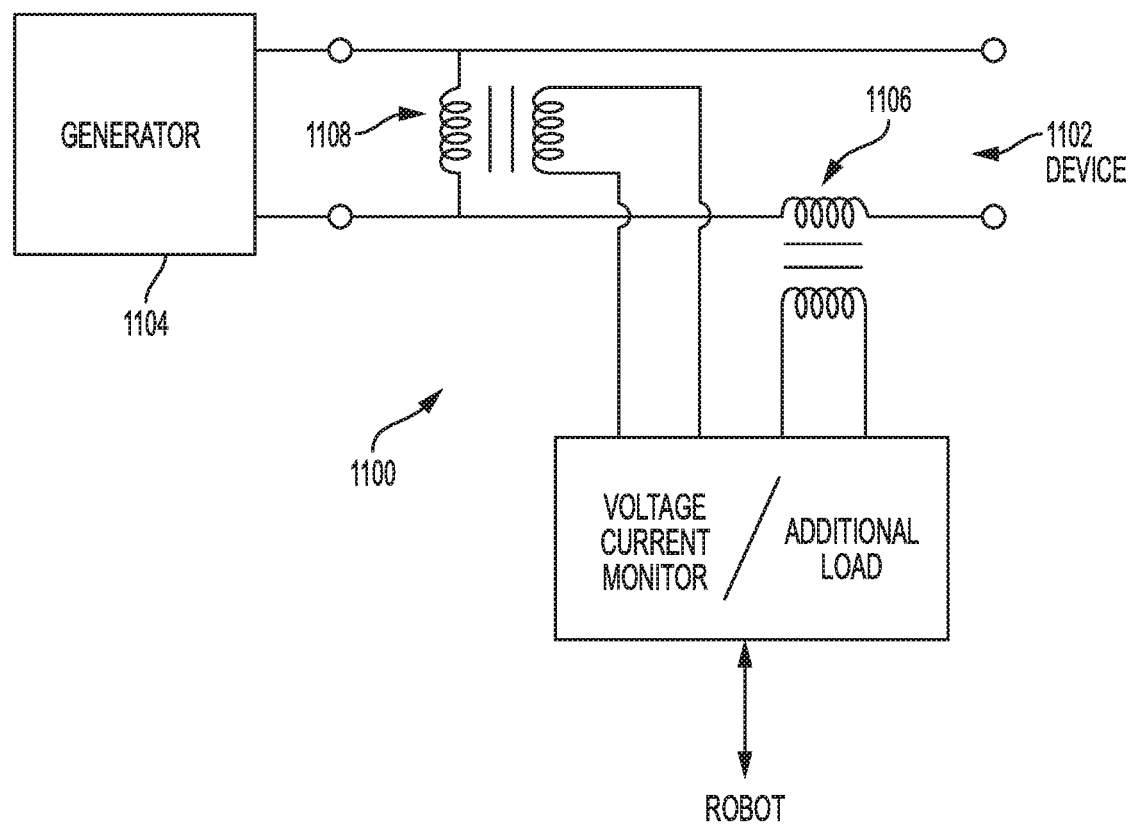
FIG. 31 is a schematic view of one embodiment of a control system operatively coupled to a generator and an electrosurgical tool.

FIG. 31 illustrates one embodiment of a control system 1100 configured to monitor one or more parameters of an electrosurgical tool 1102 operatively coupled thereto and to manipulate the parameter data before transmitting the manipulated data to a generator 1104. In this illustrated embodiment, the control system 1100 is configured to monitor voltage/current and load applied by the electrosurgical tool's end effector. The control system is 1100 is configured to manipulate the voltage/current data and the load data by processing the voltage/current data and the load data through transformers 1106, 1108 in parallel. The transformed voltage/current data and the transformed load data can then be used by the generator 1104 to make decisions, e.g., how much energy to deliver to the electrosurgical tool 1102 for application to tissue by the tool's end effector.

Figure 32:
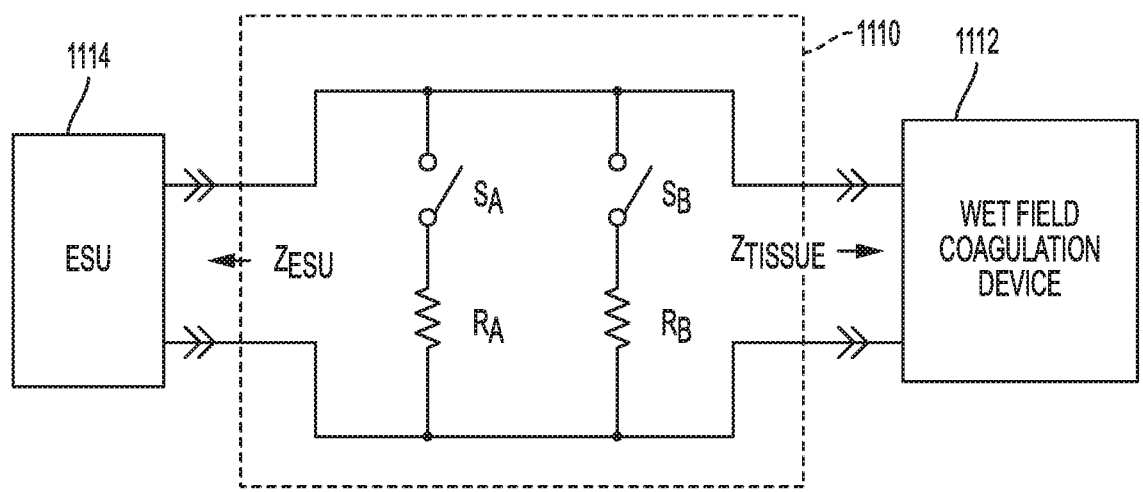
FIG. 32 is a schematic view of another embodiment of a control system operatively coupled to a generator and an electrosurgical tool.

FIG. 32 illustrates another embodiment of a control system 1110 configured to monitor one or more parameters of an electrosurgical tool 1112 operatively coupled thereto and to manipulate the parameter data before transmitting the manipulated data to a generator 1114. The electrosurgical tool 1112 in this illustrated embodiment is a wet field coagulation device, but other electrosurgical tools can be used. In this illustrated embodiment, the control system 1110 is configured to monitor impedance of tissue engaged by the electrosurgical tool 1112, manipulate the impedance data, and transmit the manipulated impedance data to the generator 1114, which is configured to use the manipulated impedance data in determining energy to deliver to the tool 1112 via the control system 1110. The control system 1110 is configured to manipulate the impedance data using first and second switches $S_A$ and $S_B$ and first and second resistors $R_1$ and $R_2$.

Figures 33, 34:
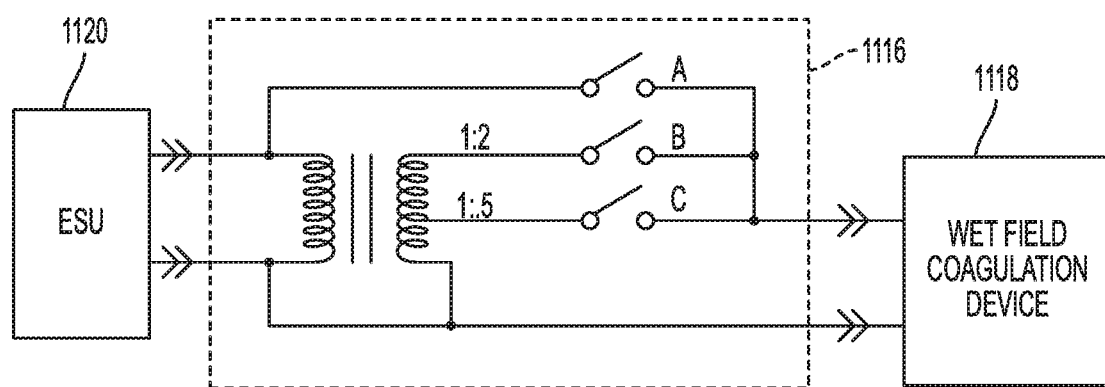
FIG. 33 is a table illustrating modes of processing of the control system of FIG. 32.
FIG. 34 is a schematic view of a surgical system including a control system operatively coupled to a generator and an electrosurgical tool.

FIG. 33 shows a table illustrating four modes of impedance data processing by the control system 1110. Based on the measured impedance, the control system 1110 is configured to determine that the generator should run at a higher power level than the generator is configured to run under normal operating conditions, e.g., should provide more power than the generator is configured to provide under normal operating conditions. Depending on how high a power level the control system 1110 determines is needed based on the measured impedance, the control system 1110 can close selected one or more of the switches $S_A$, $S_B$, and $S_C$. The control system 1110 can be pre-programmed with impedance levels corresponding to different power levels. In a first mode the first and second switches $S_A$ and $S_B$ are open, and the impedance data bypasses the first and second resistors $R_1$ and $R_2$ and is transmitted to the generator 1114 without modification. The generator 1114 is thus making decisions based on "real" data that has not been manipulated by the control system 1110 to fool or spoof the generator 1114. In a second mode the first switch $S_A$ is closed and the second switch $S_B$ is open, and the impedance data is manipulated by passing through the first resistor $R_A$ before being received by the generator 1114. The generator 114 is thus being spoofed or fooled by the control system 1110 in the second mode. In a third mode the first switch $S_A$ is open and the second switch $S_B$ is closed, and the impedance data is manipulated by passing through the second resistor $R_B$ before being received by the generator 1114. The generator 114 is thus being spoofed or fooled by the control system 1110 in the third mode. In a fourth mode the first and second switches $S_A$ and $S_B$ are closed, and the impedance data is manipulated by passing through the first and second resistors $R_1$ and $R_2$ before being received by the generator 1114. The generator 114 is thus being spoofed or fooled by the control system 1110 in the fourth mode.

FIG. 34 illustrates another embodiment of a control system 1116 configured to monitor one or more parameters of an electrosurgical tool 1118 operatively coupled thereto and to manipulate the parameter data before transmitting the manipulated data to a generator 1120. The electrosurgical tool 1118 in this illustrated embodiment is a wet field coagulation device, but other electrosurgical tools can be used. In this illustrated embodiment, the control system 1116 is configured to monitor parameter(s) from the electrosurgical tool 1118, manipulate the data, and transmit the manipulated data to the generator 1120, which is configured to use the manipulated data in determining energy to deliver to the tool 1118 via the control system 1116. The control system 1116 is configured to manipulate the parameter data using first, second, and third switches A, B, C and a transformer. In general, the control system 1116 is configured to force the generator 1120 to deliver energy as if tissue engaged by the tool 1118 is thick when the tissue is in reality thin, as indicated by the sensed parameter(s).

Figure 35:
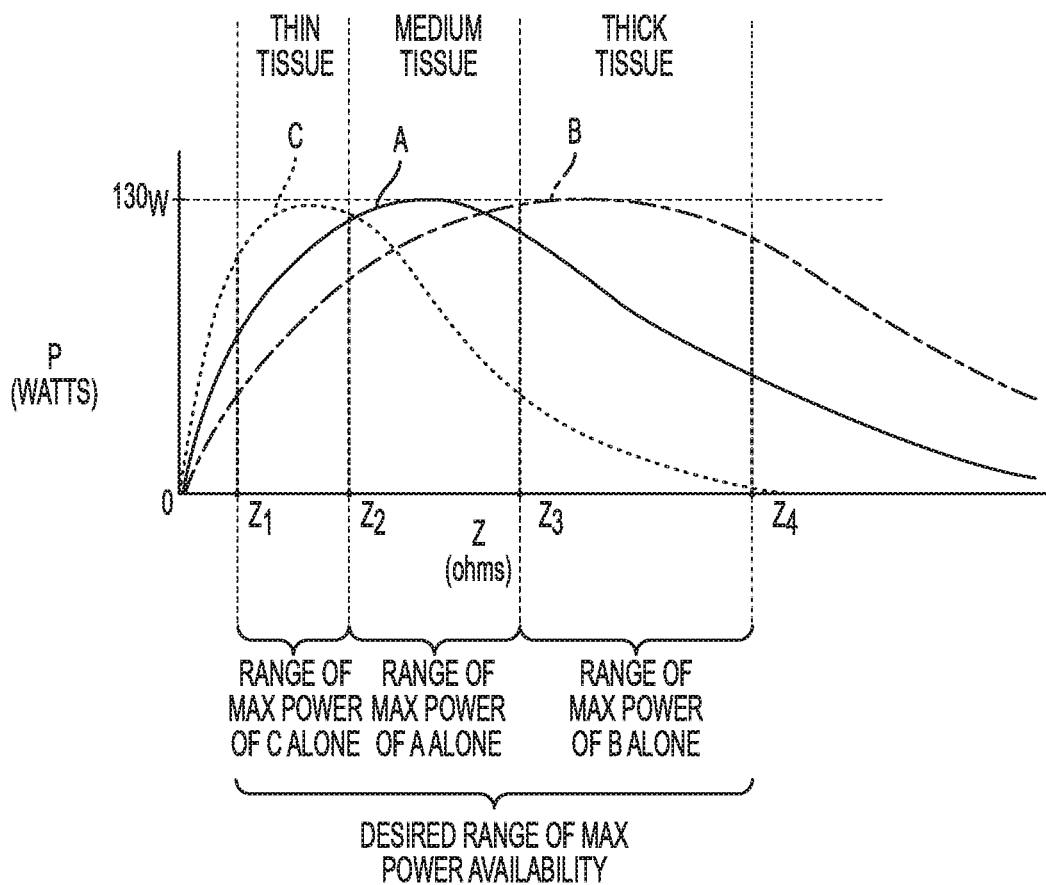
FIG. 35 is a graph illustrating power versus impedance for the surgical system of FIG. 34.

FIG. 35 illustrates operability of the control system 1116 when various ones of the first, second, and third switches A, B, C are closed and when the monitored parameter is impedance. Maximum power P from the generator 1120 is shown as 130 W in this illustrated embodiment, but other maximum powers are possible. In a first mode the first switch A is closed and the second and third switches B, C are open, as represented by curve A in FIG. 35. For a sensed impedance between $Z_2$ and $Z_3$, the control system 1116 is configured to operate in the first mode to achieve maximum power. The first mode corresponds to medium thickness tissue being engaged by the tool 1118. In a second mode the second switch B is closed and the first and third switches A, C are open, as represented by curve B in FIG. 35. For a sensed impedance between $Z_3$ and $Z_4$, the control system 1116 is configured to operate in the second mode to achieve maximum power. The second mode corresponds to thick tissue being engaged by the tool 1118. In a third mode the third switch C is closed and the first and second switches A, B are open, as represented by curve C in FIG. 35. For a sensed impedance between $Z_1$ and $Z_2$, the control system 1116 is configured to operate in the third mode to achieve maximum power. The third mode corresponds to thin tissue being engaged by the tool 1118. In this illustrated embodiment the manipulated impedance in the second mode has a 1:2 ratio with the sensed impedance, which is the impedance in the first mode. In this illustrated embodiment the manipulated impedance in the third mode has a 1:5 ratio with the sensed impedance.

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

Figure 36:
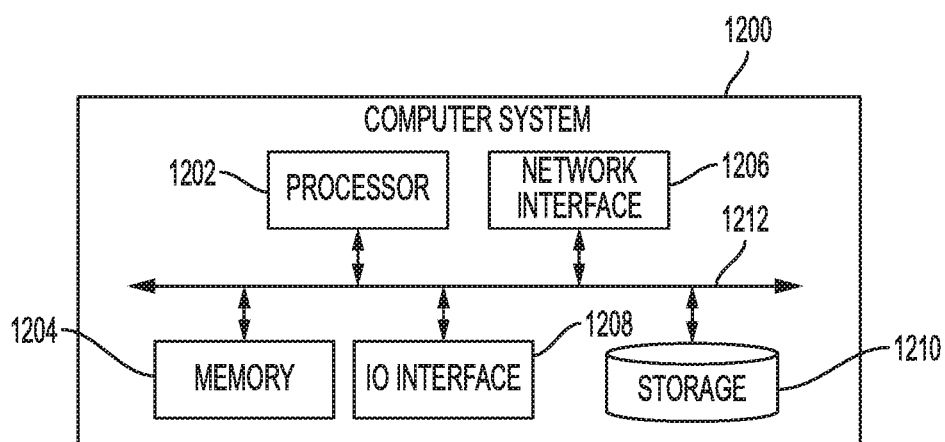
FIG. 36 illustrates one exemplary embodiment of a computer system that can be used to implement a control system of the present disclosure.

FIG. 36 illustrates one exemplary embodiment of a computer system 1200. As shown, the computer system 1200 includes one or more processors 1202 which can control the operation of the computer system 1200. "Processors" are also referred to herein as "controllers." The processor(s) 1202 can include any type of microprocessor or central processing unit (CPU), including programmable general-purpose or special-purpose microprocessors and/or any one of a variety of proprietary or commercially available single or multi-processor systems. The computer system 1200 can also include one or more memories 1204, which can provide temporary storage for code to be executed by the processor(s) 1202 or for data acquired from one or more users, storage devices, and/or databases. The memory 1204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1200 can be coupled to a bus system 1212 The illustrated bus system 1212 is an abstraction that represents any one or more separate physical busses, communication lines/interfaces, and/or multi-drop or point-to-point connections, connected by appropriate bridges, adapters, and/or controllers. The computer system 1200 can also include one or more network interface(s) 1206 that enable the computer system 1200 to communicate with remote devices, e.g., motor(s) coupled to the drive system that is located within the surgical device or a robotic surgical system, one or more input/output (IO) interface(s) 1208 that can include one or more interface components to connect the computer system 1200 with other electronic equipment, such as sensors located on the motor (s), and one or more storage device(s) 1210. The storage device(s) 1210 can include any conventional medium for storing data in a non-volatile and/or non-transient manner. The storage device(s) 1210 can thus hold data and/or instructions in a persistent state, i.e., the value(s) are retained despite interruption of power to the computer system 1200.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   a surgical tool including an elongate shaft, an end effector at a distal end of the elongate shaft, and a housing at a proximal end of the elongate shaft, the end effector being configured to selectively deliver radiofrequency energy and ultrasound energy to tissue engaged by the end effector; and
   a control system configured to:
      cause the end effector to selectively deliver the radiofrequency energy and the ultrasound energy to the tissue, and
      vary a force applied by the end effector to the tissue engaged by the end effector based on whether the surgical tool is operating in a first mode in which radiofrequency energy but not ultrasound energy is being delivered to the tissue, is operating in a second mode in which both radiofrequency energy and ultrasound energy are being applied to the tissue, and is operating in a third mode in which ultrasound energy but not radiofrequency energy is being applied to the tissue;
   wherein the force applied by the end effector to the tissue is greater in the first and third modes than in the second mode.

2. The surgical system of claim 1, further comprising a sensor configured to sense impedance of the tissue engaged by the end effector;
   wherein the control system is configured to vary the force also based on the sensed impedance.

3. The surgical system of claim 2, wherein, when the surgical tool is operating in the first mode, the control system is configured to reduce the force in response to the sensed impedance decreasing and to increase the force in response to the sensed impedance increasing.

4. The surgical system of claim 1, wherein the end effector is configured to clamp tissue, and the force is a compressive force on the clamped tissue.

5. The surgical system of claim 4, wherein the surgical tool includes a closure assembly disposed at least partially in the housing and configured to be actuated to move the end effector between an open position and a closed position; and
   the control system is configured to vary the force by opening or closing the end effector.

6. The surgical system of claim 1, wherein the surgical tool operating in the first mode causes coagulation of the tissue engaged by the end effector, the surgical tool operating in the second mode enhances the coagulation, and the surgical tool operating in the third mode causes cutting of the tissue engaged by the end effector.

7. The surgical system of claim 1, further comprising a tool driver of a robotic surgical system configured to operatively connect to the housing, the control system being a component of the robotic surgical system.

8. The surgical system of claim 7, wherein the tool driver includes at least one motor configured to drive the delivery of the radiofrequency energy, configured to drive the delivery of the ultrasound energy, and configured to vary the force applied by the end effector.

9. A surgical system, comprising:
a surgical tool including an elongate shaft, an end effector at a distal end of the elongate shaft, and a housing at a proximal end of the elongate shaft, the end effector being configured to selectively deliver radiofrequency energy and ultrasound energy to tissue engaged by the end effector; and
a control system configured to:
cause the end effector to selectively deliver the radiofrequency energy and the ultrasound energy to the tissue, and
vary a force applied by the end effector to the tissue engaged by the end effector based on whether the surgical tool is operating in a first mode in which radiofrequency energy but not ultrasound energy is being delivered to the tissue, is operating in a second mode in which both radiofrequency energy and ultrasound energy are being applied to the tissue, and is operating in a third mode in which ultrasound energy but not radiofrequency energy is being applied to the tissue;
wherein in the second mode more ultrasound energy than radiofrequency energy is being applied to the tissue, the surgical tool is configured to operate in a fourth mode in which both radiofrequency energy and ultrasound energy are being applied to the tissue and more radiofrequency energy than ultrasound energy is being applied to the tissue, and the control system is configured to vary the force also based on whether the surgical tool is operating in the fourth mode.

10. The surgical system of claim 9,
wherein the force applied by the end effector to the tissue is greater in the first and third modes than in the second mode.

11. The surgical system of claim 9, further comprising a sensor configured to sense impedance of the tissue engaged by the end effector;
wherein the control system is configured to vary the force also based on the sensed impedance; and
wherein, when the surgical tool is operating in the first mode, the control system is configured to reduce the force in response to the sensed impedance decreasing and to increase the force in response to the sensed impedance increasing.

12. A surgical system, comprising:
a surgical tool including an elongate shaft, an end effector at a distal end of the elongate shaft, a housing at a proximal end of the elongate shaft, and a closure assembly disposed at least partially in the housing and configured to be actuated to move the end effector between an open position and a closed position, the end effector being configured to selectively deliver radiofrequency energy and ultrasound energy to tissue clamped by the end effector;
a sensor configured to sense impedance of the tissue engaged by the end effector;
a motor configured to drive the closure assembly; and
a control system configured to control the motor to drive the actuation of the closure assembly such that the end effector applies a variable compressive force to the tissue clamped thereby based on the sensed impedance and based on whether both radiofrequency energy and ultrasound energy are currently being applied to the tissue clamped by the end effector or only one of radiofrequency energy and ultrasound energy is currently being applied to the tissue clamped by the end effector;
wherein, when only one of radiofrequency energy and ultrasound energy is currently being applied, the control system is configured to reduce the compressive force in response to the sensed impedance decreasing and is configured to increase the compressive force in response to the sensed impedance increasing.

13. The surgical system of claim 12, wherein the compressive force is less when both radiofrequency energy and ultrasound energy are currently being applied than when only one of radiofrequency energy and ultrasound energy is currently being applied.

14. The surgical system of claim 13, wherein, when both radiofrequency energy and ultrasound energy are currently being applied, the compressive force is less when more ultrasound energy than radiofrequency energy is currently being applied than when more radiofrequency energy than ultrasound energy is currently being applied.

15. The surgical system of claim 12, wherein the sensed impedance is indicative of whether both radiofrequency energy and ultrasound energy are currently being applied or only one of radiofrequency energy and ultrasound energy is currently being applied.

16. The surgical system of claim 12, further comprising a tool driver assembly configured to be operatively connected to the housing, the tool driver assembly including the motor, and the tool driver assembly and the control system being components of a robotic surgical system.

17. The surgical system of claim 12, wherein the surgical tool includes at least two electrodes configured to apply the radiofrequency energy to the tissue.

18. A surgical system, comprising:
a surgical tool including an elongate shaft, an end effector at a distal end of the elongate shaft, a housing at a proximal end of the elongate shaft, and a closure assembly disposed at least partially in the housing and configured to be actuated to move the end effector between an open position and a closed position, the end effector being configured to selectively deliver radiofrequency energy and ultrasound energy to tissue clamped by the end effector;
a sensor configured to sense impedance of the tissue engaged by the end effector;
a motor configured to drive the closure assembly; and
a control system configured to control the motor to drive the actuation of the closure assembly such that the end effector applies a variable compressive force to the tissue clamped thereby based on the sensed impedance and based on whether both radiofrequency energy and ultrasound energy are currently being applied to the tissue clamped by the end effector or only one of radiofrequency energy and ultrasound energy is currently being applied to the tissue clamped by the end effector;
wherein the compressive force is less when both radiofrequency energy and ultrasound energy are currently being applied than when only one of radiofrequency energy and ultrasound energy is currently being applied.

19. The surgical system of claim 18, wherein, when only one of radiofrequency energy and ultrasound energy is currently being applied, the control system is configured to reduce the compressive force in response to the sensed impedance decreasing and is configured to increase the compressive force in response to the sensed impedance increasing.

20. The surgical system of claim 18, wherein, when both radiofrequency energy and ultrasound energy are currently being applied, the compressive force is less when more ultrasound energy than radiofrequency energy is currently being applied than when more radiofrequency energy than ultrasound energy is currently being applied.

* * * * *